United States Patent [19]
Goodman et al.

[11] Patent Number: 5,807,826
[45] Date of Patent: Sep. 15, 1998

[54] SEMAPHORIN GENE FAMILY

[75] Inventors: Corey S. Goodman; Alex L. Kolodkin; David Matthes; David R. Bentley; Timothy O'Connor, all of Berkeley, Calif.

[73] Assignee: The Regents of the University of California, Oakland, Calif.

[21] Appl. No.: 835,268

[22] Filed: Apr. 8, 1997

Related U.S. Application Data

[62] Division of Ser. No. 121,713, Sep. 13, 1993, Pat. No. 5,639,856.

[51] Int. Cl.$^6$ .......................... A61K 38/04; A61K 38/16
[52] U.S. Cl. ............................. 514/12; 514/14; 514/15; 514/16; 514/17; 514/21
[58] Field of Search ...................... 530/326, 327, 530/328, 329, 330, 350; 514/12, 14, 15, 16, 17, 21

[56] References Cited

U.S. PATENT DOCUMENTS 5,639,856   6/1997   Goodman et al. ...................... 530/326

*Primary Examiner*—Jeffrey E. Russel
*Attorney, Agent, or Firm*—Richard Aron Osman

[57] ABSTRACT

A novel class of proteins, semaphorins, nucleic acids encoding semaphorins, semaphorin peptides, and methods of using semaphorins and semaphorin-encoding nucleic acids are disclosed. Semaphorin peptides and receptor agonists and antagonists provide potent modulators of nerve cell growth and regeneration. The invention provides pharmaceutical compositions, methods for screening chemical libraries for regulators of cell growth/differentiation; semaphorin gene-derived nucleic acids for use in genetic mapping, as probes for related genes, and as diagnostic reagents for genetic neurological disease; specific cellular and animal systems for the development of neurological disease therapy.

23 Claims, No Drawings

SEQUENCE LISTING ( 1 ) GENERAL INFORMATION:

( i i i ) NUMBER OF SEQUENCES: 100

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=SEQ01
            / note= "Xaa denotes D or E at residue #1; Q,K,R,A
            or N at residue #3; and Y,F or V at residue #5"

( x i ) SEQUENCE DESCRIPTION: SEQ ID NO:1:

Xaa Cys Xaa Asn Xaa Ile
1                   5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=SEQ02
            / note= "Xaa denotes Q,K,R,A or N at residue #2;
            Y,F or V at residue #4; and R,K,Q or T at residue
            # 6"

( x i ) SEQUENCE DESCRIPTION: SEQ ID NO:2:

Cys Xaa Asn Xaa Ile Xaa
1                   5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ03
            / note= "Xaa denotes N or G at residue #4; A,S or N
            at residue #5; Y,F,H or G at residue #6; and
            K,R,H,N or Q at residue #7"

( x i ) SEQUENCE DESCRIPTION: SEQ ID NO:3:

Cys Gly Thr Xaa Xaa Xaa Xaa
1                   5

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ04
            / note= "Xaa denotes N or G at residue #4; and A,S
            or N at residue #5"

( x i ) SEQUENCE DESCRIPTION: SEQ ID NO:4:

Cys Gly Thr Xaa Xaa Xaa Xaa Pro
1                   5

( 2 ) INFORMATION FOR SEQ ID NO:5:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..10
  ( D ) OTHER INFORMATION: /label=SEQ05
    / note= "Xaa denotes N or G at residue #4; and C or
    D at residue #10"

( x i ) SEQUENCE DESCRIPTION: SEQ ID NO:5:

Cys Gly Thr Xaa Xaa Xaa Xaa Pro Xaa Xaa
1      5          1 0

( 2 ) INFORMATION FOR SEQ ID NO:6:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..13
  ( D ) OTHER INFORMATION: /label=SEQ06
    / note= "Xaa denotes C or D at residue #10; and Y
    or I at residue #13"

( x i ) SEQUENCE DESCRIPTION: SEQ ID NO:6:

Cys Gly Thr Xaa Xaa Xaa Xaa Pro Xaa Xaa Xaa Xaa Xaa
1      5          1 0

( 2 ) INFORMATION FOR SEQ ID NO:7:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..7
  ( D ) OTHER INFORMATION: /label=SEQ07
    / note= "Xaa denotes R,I,Q or V at residue #1; G or
    A at residue #2; L,V or K at residue #3; C or S at
    residue #4; F or Y at residue #6; and D or N at
    residue #7"

( x i ) SEQUENCE DESCRIPTION: SEQ ID NO:7:

Xaa Xaa Xaa Xaa Pro Xaa Xaa
1      5

( 2 ) INFORMATION FOR SEQ ID NO:8:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i x ) FEATURE:

(A) NAME/KEY: Peptide
(B) LOCATION: 1..7
(D) OTHER INFORMATION: /label=SEQ08
/ note= "Xaa denotes C or S at residue #1; F or Y at residue #3; D or N at residue #4; D,E,R or K at residue #6; and H,L or D at residue #7"

(xi) SEQUENCE DESCRIPTION: SEQ ID NO:8:

Xaa Pro Xaa Xaa Pro Xaa Xaa
1                   5

(2) INFORMATION FOR SEQ ID NO:9:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..9
(D) OTHER INFORMATION: /label=SEQ09
/ note= "Xaa denotes G or A at residue #3; C or S at residue #5; and D or N at residue #8"

(xi) SEQUENCE DESCRIPTION: SEQ ID NO:9:

Gly Xaa Xaa Xaa Xaa Pro Tyr Xaa Pro
1                   5

(2) INFORMATION FOR SEQ ID NO:10:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..7
(D) OTHER INFORMATION: /label=SEQ10
/ note= "Xaa denotes F or Y at residue #2; G or A at residue #4; and V,N or A at residue #6"

(xi) SEQUENCE DESCRIPTION: SEQ ID NO:10:

Leu Xaa Ser Xaa Thr Xaa Ala
1                   5

(2) INFORMATION FOR SEQ ID NO:11:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..9
(D) OTHER INFORMATION: /label=SEQ11
/ note= "Xaa denotes F or Y at residue #2; D or E at residue #8; and F or Y at residue #9"

(xi) SEQUENCE DESCRIPTION: SEQ ID NO:11:

Leu Xaa Ser Xaa Thr Xaa Ala Xaa Xaa
1                   5

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ12
            / note= "Xaa denotes F or Y at residue #1; G or A
            at residue #3; V,N or A at residue #5; D or E at
            residue #7; and F or Y at residue #8"

( x i ) SEQUENCE DESCRIPTION: SEQ ID NO:12:

Xaa Ser Xaa Thr Xaa Ala Xaa Xaa
1                      5

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ13
            / note= "Xaa denotes N or D at residue #2; and A or
            K at residue #3"

( x i ) SEQUENCE DESCRIPTION: SEQ ID NO:13:

Leu Xaa Xaa Pro Asn Phe Val
1                  5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Phe Phe Phe Arg Glu
1              5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=SEQ15
            / note= "Xaa denotes F or Y at residue #3; and T or N at residue #6"

( x i ) SEQUENCE DESCRIPTION: SEQ ID NO:15:

Phe Phe Xaa Arg Glu Xaa
1               5

( 2 ) INFORMATION FOR SEQ ID NO:16:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..6
  ( D ) OTHER INFORMATION: /label=SEQ16
        / note= "Xaa denotes T or N at residue #5"

( x i ) SEQUENCE DESCRIPTION: SEQ ID NO:16:

Phe Phe Arg Glu Xaa Ala
1               5

( 2 ) INFORMATION FOR SEQ ID NO:17:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..6
  ( D ) OTHER INFORMATION: /label=SEQ17
        / note= "Xaa denotes F or Y at residue #2; and T or
        N at residue #5"

( x i ) SEQUENCE DESCRIPTION: SEQ ID NO:17:

Phe Xaa Arg Glu Xaa Ala
1               5

( 2 ) INFORMATION FOR SEQ ID NO:18:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..6
  ( D ) OTHER INFORMATION: /label=SEQ18
        / note= "Xaa denotes F or Y at residue #4"

( x i ) SEQUENCE DESCRIPTION: SEQ ID NO:18:

Tyr Phe Phe Xaa Arg Glu
1               5

( 2 ) INFORMATION FOR SEQ ID NO:19:

( i ) SEQUENCE CHARACTERISTICS:
  ( A ) LENGTH: 6 amino acids
  ( B ) TYPE: amino acid ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..6
                ( D ) OTHER INFORMATION: /label=SEQ19
                        / note= "Xaa denotes F or Y at residue #1; and F or
                        Y at residue #4"

( x i ) SEQUENCE DESCRIPTION: SEQ ID NO:19:

Xaa  Phe  Phe  Xaa  Arg  Glu
    1                  5

( 2 ) INFORMATION FOR SEQ ID NO:20:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..7
                ( D ) OTHER INFORMATION: /label=SEQ20
                        / note= "Xaa denotes F or Y at residue #1; F or Y
                        at residue #2; F or Y at residue #3; and T or N at
                        residue #6"

( x i ) SEQUENCE DESCRIPTION: SEQ ID NO:20:

Xaa  Xaa  Xaa  Arg  Glu  Xaa  Ala
    1                  5

( 2 ) INFORMATION FOR SEQ ID NO:21:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..7
                ( D ) OTHER INFORMATION: /label=SEQ21
                        / note= "Xaa denotes I or V at residue #1; F or Y
                        at residue #2; F or Y at residue #4; and F or Y at
                        residue #5"

( x i ) SEQUENCE DESCRIPTION: SEQ ID NO:21:

Xaa  Xaa  Phe  Xaa  Xaa  Arg  Glu
    1                  5

( 2 ) INFORMATION FOR SEQ ID NO:22:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..7
                ( D ) OTHER INFORMATION: /label=SEQ22

/ note= "Xaa denotes K,F or Y at residue #2; F or Y
at residue #4; F,Y,I or L at residue #5; F,Y,I or
L at residue #6; and F or Y at residue #7"

( x i ) SEQUENCE DESCRIPTION: SEQ ID NO:22:

Asp Xaa Val Xaa Xaa Xaa Xaa
1               5

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ23
            / note= "Xaa denotes V or I at residue #1; F or Y
            at residue #2; F,Y,I or L at residue #3; F,Y,I or
            L at residue #4; R or T at residue #6; and T or N
            at residue #8"

( x i ) SEQUENCE DESCRIPTION: SEQ ID NO:23:

Xaa Xaa Xaa Xaa Phe Xaa Xaa Xaa
1               5

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ24
            / note= "Xaa denotes V or I at residue #1; F or Y
            at residue #2; F,Y,I or L at residue #3; F,Y,I or
            L at residue #4; F or Y at residue #5; R or T at
            residue #6; E,D or V at residue #7; and T or N at
            residue #8"

( x i ) SEQUENCE DESCRIPTION: SEQ ID NO:24:

Xaa Xaa Xaa Xaa Xaa Xaa Xaa Xaa
1               5

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=SEQ25
            / note= "Xaa denotes F or Y at residue #2; and C or
            S at residue #5"

( x i ) SEQUENCE DESCRIPTION: SEQ ID NO:25:

```
Glu  Xaa  Ile  Asn  Xaa  Gly  Lys
1                 5
```

(2) INFORMATION FOR SEQ ID NO:26:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label=SEQ26
            / note= "Xaa denotes F or Y at residue #1; and A,V
            or I at residue #7"

(xi) SEQUENCE DESCRIPTION: SEQ ID NO:26:

```
Xaa  Ile  Asn  Cys  Gly  Lys  Xaa
1                 5
```

(2) INFORMATION FOR SEQ ID NO:27:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label=SEQ27
            / note= "Xaa denotes V or I at residue #2; A or G
            at residue #3; R or Q at residue #4; and V or I at
            residue #5"

(xi) SEQUENCE DESCRIPTION: SEQ ID NO:27:

```
Arg  Xaa  Xaa  Xaa  Xaa  Cys  Lys
1                 5
```

(2) INFORMATION FOR SEQ ID NO:28:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label=SEQ28
            / note= "Xaa denotes V or I at residue #2; R or Q
            at residue #4; and V or I at residue #5"

(xi) SEQUENCE DESCRIPTION: SEQ ID NO:28:

```
Arg  Xaa  Xaa  Xaa  Xaa  Cys  Xaa  Xaa  Asp
1                 5
```

(2) INFORMATION FOR SEQ ID NO:29:

(i) SEQUENCE CHARACTERISTICS:
        (A) LENGTH: 13 amino acids
        (B) TYPE: amino acid
        (C) STRANDEDNESS: single (D) TOPOLOGY: linear (i i) MOLECULE TYPE: peptide (i x) FEATURE:
    (A) NAME/KEY: Peptide
    (B) LOCATION: 1..13
    (D) OTHER INFORMATION: /label=SEQ29
        / note= "Xaa denotes V,A or I at residue #3; and
        V,A or I at residue #8"

(x i) SEQUENCE DESCRIPTION: SEQ ID NO:29:

Gly Lys Xaa Xaa Xaa Xaa Arg Xaa Xaa Xaa Xaa Cys Lys
1               5                       10

(2) INFORMATION FOR SEQ ID NO:30:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (i x) FEATURE:
    (A) NAME/KEY: Peptide
    (B) LOCATION: 1..7
    (D) OTHER INFORMATION: /label=SEQ30
        / note= "Xaa denotes R,K or N at residue #1; T,A or
        S at residue #3; T,A or S at residue #4; F,Y or L
        at residue #5; and K or R at residue #7"

(x i) SEQUENCE DESCRIPTION: SEQ ID NO:30:

Xaa Trp Xaa Xaa Xaa Leu Xaa
1               5

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i x) FEATURE:
    (A) NAME/KEY: Peptide
    (B) LOCATION: 1..8
    (D) OTHER INFORMATION: /label=SEQ31
        / note= "Xaa denotes F or Y at residue #1; K or R
        at residue #3; A or S at residue #4; and N or I at
        residue #7"

(x i) SEQUENCE DESCRIPTION: SEQ ID NO:31:

Xaa Leu Xaa Xaa Arg Leu Xaa Cys
1               5

(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i x) FEATURE:
    (A) NAME/KEY: Peptide
    (B) LOCATION: 1..6
    (D) OTHER INFORMATION: /label=SEQ32
        / note= "Xaa denotes N or I at residue #1; I or V at residue #4; and P or S at residue #5"

(xi) SEQUENCE DESCRIPTION: SEQ ID NO:32:

Xaa Cys Ser Xaa Xaa Gly
1               5

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label=SEQ33
            / note= "Xaa denotes T,A or S at residue #2; T,A or
            S at residue #3; F,Y or L at residue #4; and
            A,S,V,I or L at residue #7"

(xi) SEQUENCE DESCRIPTION: SEQ ID NO:33:

Trp Xaa Xaa Xaa Leu Lys Xaa Xaa Leu
1               5

(2) INFORMATION FOR SEQ ID NO:34:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..11
        (D) OTHER INFORMATION: /label=SEQ34
            / note= "Xaa denotes T,A or S at residue #2; and
            T,A or S at residue #3"

(xi) SEQUENCE DESCRIPTION: SEQ ID NO:34:

Trp Xaa Xaa Xaa Leu Lys Xaa Xaa Leu Xaa Cys
1               5                   10

(2) INFORMATION FOR SEQ ID NO:35:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..11
        (D) OTHER INFORMATION: /label=SEQ35
            / note= "Xaa denotes T or S at residue #3"

(xi) SEQUENCE DESCRIPTION: SEQ ID NO:35:

Trp Xaa Xaa Xaa Leu Lys Xaa Xaa Leu Xaa Cys
1               5                   10

(2) INFORMATION FOR SEQ ID NO:36:

(i) SEQUENCE CHARACTERISTICS:

( A ) LENGTH: 7 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..7
( D ) OTHER INFORMATION: /label=SEQ36
/ note= "Xaa denotes F or Y at residue #1; F or Y
at residue #2; and N or D at residue #3"

( x i ) SEQUENCE DESCRIPTION: SEQ ID NO:36:

Xaa  Xaa  Xaa  Glu  Ile  Gln  Ser
1                  5

( 2 ) INFORMATION FOR SEQ ID NO:37:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..7
( D ) OTHER INFORMATION: /label=SEQ37
/ note= "Xaa denotes F or Y at residue #1; F or Y
at residue #3; F or Y at residue #4; F or Y at
residue #5; and N or D at residue #6"

( x i ) SEQUENCE DESCRIPTION: SEQ ID NO:37:

Xaa  Pro  Xaa  Xaa  Xaa  Xaa  Glu
1                  5

( 2 ) INFORMATION FOR SEQ ID NO:38:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..7
( D ) OTHER INFORMATION: /label=SEQ38
/ note= "Xaa denotes V,I or L at residue #4; and F
or Y at residue #7"

( x i ) SEQUENCE DESCRIPTION: SEQ ID NO:38:

Gly  Ser  Ala  Xaa  Cys  Xaa  Xaa
1                  5

( 2 ) INFORMATION FOR SEQ ID NO:39:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..8

( D ) OTHER INFORMATION: /label=SEQ39
/ note= "Xaa denotes V,I or L at residue #3; and F
or Y at residue #6"

( x i ) SEQUENCE DESCRIPTION: SEQ ID NO:39:

Ser Ala Xaa Cys Xaa Xaa Xaa Met
1               5

( 2 ) INFORMATION FOR SEQ ID NO:40:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..7
      ( D ) OTHER INFORMATION: /label=SEQ40
        / note= "Xaa denotes N or A at residue #3; and P or
        A at residue #6"

( x i ) SEQUENCE DESCRIPTION: SEQ ID NO:40:

Asn Ser Xaa Trp Leu Xaa Val
1               5

( 2 ) INFORMATION FOR SEQ ID NO:41:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..7
      ( D ) OTHER INFORMATION: /label=SEQ41
        / note= "Xaa denotes V,L or I at residue #1; and
        E,D,Y,S or F at residue #3"

( x i ) SEQUENCE DESCRIPTION: SEQ ID NO:41:

Xaa Pro Xaa Pro Arg Pro Gly
1               5

( 2 ) INFORMATION FOR SEQ ID NO:42:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..9
      ( D ) OTHER INFORMATION: /label=SEQ42
        / note= "Xaa denotes V,L or I at residue #1; and R
        or A at residue #5"

( x i ) SEQUENCE DESCRIPTION: SEQ ID NO:42:

Xaa Pro Xaa Pro Xaa Pro Gly Xaa Cys
1               5

( 2 ) INFORMATION FOR SEQ ID NO:43:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /label=SEQ43
        / note= "Xaa denotes E,D,Y,S or F at residue #2;
        and T,Q or S at residue #7"

( x i ) SEQUENCE DESCRIPTION: SEQ ID NO:43:

Pro  Xaa  Pro  Arg  Pro  Gly  Xaa  Cys
1                        5

( 2 ) INFORMATION FOR SEQ ID NO:44:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=SEQ44
        / note= "Xaa denotes H,F or Y at residue #3; and A
        or G at residue #5"

( x i ) SEQUENCE DESCRIPTION: SEQ ID NO:44:

Asp  Pro  Xaa  Cys  Xaa  Trp
1                        5

( 2 ) INFORMATION FOR SEQ ID NO:45:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=SEQ45
        / note= "Xaa denotes H,F or Y at residue #2; and A
        or G at residue #4"

( x i ) SEQUENCE DESCRIPTION: SEQ ID NO:45:

Pro  Xaa  Cys  Xaa  Trp  Asp
1                        5

( 2 ) INFORMATION FOR SEQ ID NO:46:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide (B) LOCATION: 1..7
(D) OTHER INFORMATION: /label=SEQ46
/ note= "Xaa denotes A or G at residue #5"

(xi) SEQUENCE DESCRIPTION: SEQ ID NO:46:

Asp Pro Xaa Cys Xaa Trp Asp
1               5

(2) INFORMATION FOR SEQ ID NO:47:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:47:

Cys Xaa Xaa Xaa Xaa Asp Pro Xaa Cys Xaa Trp Asp
1               5                   10

(2) INFORMATION FOR SEQ ID NO:48:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:48:

Cys Xaa Xaa Xaa Asp Pro Xaa Cys Xaa Trp Asp
1               5                   10

(2) INFORMATION FOR SEQ ID NO:49:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:49:

Cys Xaa Xaa Asp Pro Xaa Cys Xaa Trp Asp
1               5                   10

(2) INFORMATION FOR SEQ ID NO:50:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:50:

Cys Xaa Xaa Cys Xaa Xaa Xaa Xaa Asp Xaa Xaa Cys Xaa Trp Asp
1               5                   10                  15

(2) INFORMATION FOR SEQ ID NO:51:

(i) SEQUENCE CHARACTERISTICS:
(A) LENGTH: 14 amino acids
(B) TYPE: amino acid
(C) STRANDEDNESS: single (D) TOPOLOGY: linear (ii) MOLECULE TYPE: peptide (xi) SEQUENCE DESCRIPTION: SEQ ID NO:51:

```
Cys Xaa Xaa Cys Xaa Xaa Xaa Asp Xaa Xaa Cys Xaa Trp Asp
 1               5                   10
```

(2) INFORMATION FOR SEQ ID NO:52:

(i) SEQUENCE CHARACTERISTICS:
  (A) LENGTH: 13 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:52:

```
Cys Xaa Xaa Cys Xaa Xaa Asp Xaa Xaa Cys Xaa Trp Asp
 1               5                10
```

(2) INFORMATION FOR SEQ ID NO:53:

(i) SEQUENCE CHARACTERISTICS:
  (A) LENGTH: 2601 base pairs
  (B) TYPE: nucleic acid
  (C) STRANDEDNESS: double
  (D) TOPOLOGY: linear (ii) MOLECULE TYPE: cDNA (ix) FEATURE:
  (A) NAME/KEY: CDS
  (B) LOCATION: 16..2331

(xi) SEQUENCE DESCRIPTION: SEQ ID NO:53:

```
GGAATTCCCT GCAGC ATG GGC TGG TTA ACT AGG ATT GTC TGT CTT TTC TGG        51
              Met Gly Trp Leu Thr Arg Ile Val Cys Leu Phe Trp
               1               5                  10

GGA GTA TTA CTT ACA GCA AGA GCA AAC TAT CAG AAT GGG AAG AAC AAT        99
Gly Val Leu Leu Thr Ala Arg Ala Asn Tyr Gln Asn Gly Lys Asn Asn
         15                  20                  25

GTG CCA AGG CTG AAA TTA TCC TAC AAA GAA ATG TTG GAA TCC AAC AAT       147
Val Pro Arg Leu Lys Leu Ser Tyr Lys Glu Met Leu Glu Ser Asn Asn
     30                  35                  40

GTG ATC ACT TTC AAT GGC TTG GCC AAC AGC TCC AGT TAT CAT ACC TTC       195
Val Ile Thr Phe Asn Gly Leu Ala Asn Ser Ser Ser Tyr His Thr Phe
 45                  50                  55                  60

CTT TTG GAT GAG GAA CGG AGT AGG CTG TAT GTT GGA GCA AAG GAT CAC       243
Leu Leu Asp Glu Glu Arg Ser Arg Leu Tyr Val Gly Ala Lys Asp His
                 65                  70                  75

ATA TTT TCA TTC GAC CTG GTT AAT ATC AAG GAT TTT CAA AAG ATT GTG       291
Ile Phe Ser Phe Asp Leu Val Asn Ile Lys Asp Phe Gln Lys Ile Val
                 80                  85                  90

TGG CCA GTA TCT TAC ACC AGA AGA GAT GAA TGC AAG TGG GCT GGA AAA       339
Trp Pro Val Ser Tyr Thr Arg Arg Asp Glu Cys Lys Trp Ala Gly Lys
             95                 100                 105

GAC ATC CTG AAA GAA TGT GCT AAT TTC ATC AAG GTA CTT AAG GCA TAT       387
Asp Ile Leu Lys Glu Cys Ala Asn Phe Ile Lys Val Leu Lys Ala Tyr
         110                 115                 120

AAT CAG ACT CAC TTG TAC GCC TGT GGA ACG GGG GCT TTT CAT CCA ATT       435
Asn Gln Thr His Leu Tyr Ala Cys Gly Thr Gly Ala Phe His Pro Ile
 125                 130                 135                 140

TGC ACC TAC ATT GAA ATT GGA CAT CAT CCT GAG GAC AAT ATT TTT AAG       483
Cys Thr Tyr Ile Glu Ile Gly His His Pro Glu Asp Asn Ile Phe Lys
```

-continued

```
                        145                              150                              155
CTG  GAG  AAC  TCA  CAT  TTT  GAA  AAC  GGC  CGT  GGG  AAG  AGT  CCA  TAT  GAC         531
Leu  Glu  Asn  Ser  His  Phe  Glu  Asn  Gly  Arg  Gly  Lys  Ser  Pro  Tyr  Asp
               160                      165                     170

CCT  AAG  CTG  CTG  ACA  GCA  TCC  CTT  TTA  ATA  GAT  GGA  GAA  TTA  TAC  TCT         579
Pro  Lys  Leu  Leu  Thr  Ala  Ser  Leu  Leu  Ile  Asp  Gly  Glu  Leu  Tyr  Ser
          175                      180                     185

GGA  ACT  GCA  GCT  GAT  TTT  ATG  GGG  CGA  GAC  TTT  GCT  ATC  TTC  CGA  ACT         627
Gly  Thr  Ala  Ala  Asp  Phe  Met  Gly  Arg  Asp  Phe  Ala  Ile  Phe  Arg  Thr
     190                      195                     200

CTT  GGG  CAC  CAC  CAC  CCA  ATC  AGG  ACA  GAG  CAG  CAT  GAT  TCC  AGG  TGG         675
Leu  Gly  His  His  His  Pro  Ile  Arg  Thr  Glu  Gln  His  Asp  Ser  Arg  Trp
205                      210                     215                     220

CTC  AAT  GAT  CCA  AAG  TTC  ATT  AGT  GCC  CAC  CTC  ATC  TCA  GAG  AGT  GAC         723
Leu  Asn  Asp  Pro  Lys  Phe  Ile  Ser  Ala  His  Leu  Ile  Ser  Glu  Ser  Asp
                    225                      230                     235

AAT  CCT  GAA  GAT  GAC  AAA  GTA  TAC  TTT  TTC  TTC  CGT  GAA  AAT  GCA  ATA         771
Asn  Pro  Glu  Asp  Asp  Lys  Val  Tyr  Phe  Phe  Phe  Arg  Glu  Asn  Ala  Ile
               240                      245                     250

GAT  GGA  GAA  CAC  TCT  GGA  AAA  GCT  ACT  CAC  GCT  AGA  ATA  GGT  CAG  ATA         819
Asp  Gly  Glu  His  Ser  Gly  Lys  Ala  Thr  His  Ala  Arg  Ile  Gly  Gln  Ile
          255                      260                     265

TGC  AAG  AAT  GAC  TTT  GGA  GGG  CAC  AGA  AGT  CTG  GTG  AAT  AAA  TGG  ACA         867
Cys  Lys  Asn  Asp  Phe  Gly  Gly  His  Arg  Ser  Leu  Val  Asn  Lys  Trp  Thr
     270                      275                     280

ACA  TTC  CTC  AAA  GCT  CGT  CTG  ATT  TGC  TCA  GTG  CCA  GGT  CCA  AAT  GGC         915
Thr  Phe  Leu  Lys  Ala  Arg  Leu  Ile  Cys  Ser  Val  Pro  Gly  Pro  Asn  Gly
285                      290                     295                     300

ATT  GAC  ACT  CAT  TTT  GAT  GAA  CTG  CAG  GAT  GTA  TTC  CTA  ATG  AAC  TTT         963
Ile  Asp  Thr  His  Phe  Asp  Glu  Leu  Gln  Asp  Val  Phe  Leu  Met  Asn  Phe
                    305                      310                     315

AAA  GAT  CCT  AAA  AAT  CCA  GTT  GTA  TAT  GGA  GTG  TTT  ACG  ACT  TCC  AGT        1011
Lys  Asp  Pro  Lys  Asn  Pro  Val  Val  Tyr  Gly  Val  Phe  Thr  Thr  Ser  Ser
               320                      325                     330

AAC  ATT  TTC  AAG  GGA  TCA  GCC  GTG  TGT  ATG  TAT  AGC  ATG  AGT  GAT  GTG        1059
Asn  Ile  Phe  Lys  Gly  Ser  Ala  Val  Cys  Met  Tyr  Ser  Met  Ser  Asp  Val
          335                      340                     345

AGA  AGG  GTG  TTC  CTT  GGT  CCA  TAT  GCC  CAC  AGG  GAT  GGA  CCC  AAC  TAT        1107
Arg  Arg  Val  Phe  Leu  Gly  Pro  Tyr  Ala  His  Arg  Asp  Gly  Pro  Asn  Tyr
     350                      355                     360

CAA  TGG  GTG  CCT  TAT  CAA  GGA  AGA  GTC  CCC  TAT  CCA  CGG  CCA  GGA  ACT        1155
Gln  Trp  Val  Pro  Tyr  Gln  Gly  Arg  Val  Pro  Tyr  Pro  Arg  Pro  Gly  Thr
365                      370                     375                     380

TGT  CCC  AGC  AAA  ACA  TTT  GGT  GGT  TTT  GAC  TCT  ACA  AAG  GAC  CTT  CCT        1203
Cys  Pro  Ser  Lys  Thr  Phe  Gly  Gly  Phe  Asp  Ser  Thr  Lys  Asp  Leu  Pro
                    385                      390                     395

GAT  GAT  GTT  ATA  ACC  TTT  GCA  AGA  AGT  CAT  CCA  GCC  ATG  TAC  AAT  CCA        1251
Asp  Asp  Val  Ile  Thr  Phe  Ala  Arg  Ser  His  Pro  Ala  Met  Tyr  Asn  Pro
               400                      405                     410

GTG  TTT  CCT  ATG  AAC  AAT  CGC  CCA  ATA  GTG  ATC  AAA  ACG  GAT  GTA  AAT        1299
Val  Phe  Pro  Met  Asn  Asn  Arg  Pro  Ile  Val  Ile  Lys  Thr  Asp  Val  Asn
          415                      420                     425

TAT  CAA  TTT  ACA  CAA  ATT  GTC  GTA  GAC  CGA  GTG  GAT  GCA  GAA  GAT  GGA        1347
Tyr  Gln  Phe  Thr  Gln  Ile  Val  Val  Asp  Arg  Val  Asp  Ala  Glu  Asp  Gly
     430                      435                     440

CAG  TAT  GAT  GTT  ATG  TTT  ATC  GGA  ACA  GAT  GTT  GGG  ACC  GTT  CTT  AAA        1395
Gln  Tyr  Asp  Val  Met  Phe  Ile  Gly  Thr  Asp  Val  Gly  Thr  Val  Leu  Lys
445                      450                     455                     460

GTA  GTT  TCA  ATT  CCT  AAG  GAG  ACT  TGG  TAT  GAT  TTA  GAA  GAG  GTT  CTG        1443
Val  Val  Ser  Ile  Pro  Lys  Glu  Thr  Trp  Tyr  Asp  Leu  Glu  Glu  Val  Leu
```

```
                                465                              470                              475
CTG  GAA  GAA  ATG  ACA  GTT  TTT  CGG  GAA  CCG  ACT  GCT  ATT  TCA  GCA  ATG     1491
Leu  Glu  Glu  Met  Thr  Val  Phe  Arg  Glu  Pro  Thr  Ala  Ile  Ser  Ala  Met
               480                         485                         490

GAG  CTT  TCC  ACT  AAG  CAG  CAA  CAA  CTA  TAT  ATT  GGT  TCA  ACG  GCT  GGG     1539
Glu  Leu  Ser  Thr  Lys  Gln  Gln  Gln  Leu  Tyr  Ile  Gly  Ser  Thr  Ala  Gly
               495                         500                         505

GTT  GCC  CAG  CTC  CCT  TTA  CAC  CGG  TGT  GAT  ATT  TAC  GGG  AAA  GCG  TGT     1587
Val  Ala  Gln  Leu  Pro  Leu  His  Arg  Cys  Asp  Ile  Tyr  Gly  Lys  Ala  Cys
     510                         515                         520

GCT  GAG  TGT  TGC  CTC  GCC  CGA  GAC  CCT  TAC  TGT  GCT  TGG  GAT  GGT  TCT     1635
Ala  Glu  Cys  Cys  Leu  Ala  Arg  Asp  Pro  Tyr  Cys  Ala  Trp  Asp  Gly  Ser
525                      530                         535                         540

GCA  TGT  TCT  CGC  TAT  TTT  CCC  ACT  GCA  AAG  AGA  CGC  ACA  AGA  CGA  CAA     1683
Ala  Cys  Ser  Arg  Tyr  Phe  Pro  Thr  Ala  Lys  Arg  Arg  Thr  Arg  Arg  Gln
               545                         550                         555

GAT  ATA  AGA  AAT  GGA  GAC  CCA  CTG  ACT  CAC  TGT  TCA  GAC  TTA  CAC  CAT     1731
Asp  Ile  Arg  Asn  Gly  Asp  Pro  Leu  Thr  His  Cys  Ser  Asp  Leu  His  His
          560                         565                         570

GAT  AAT  CAC  CAT  GGC  CAC  AGC  CCT  GAA  GAG  AGA  ATC  ATC  TAT  GGT  GTA     1779
Asp  Asn  His  His  Gly  His  Ser  Pro  Glu  Glu  Arg  Ile  Ile  Tyr  Gly  Val
          575                         580                         585

GAG  AAT  AGT  AGC  ACA  TTT  TTG  GAA  TGC  AGT  CCG  AAG  TCG  CAG  AGA  GCG     1827
Glu  Asn  Ser  Ser  Thr  Phe  Leu  Glu  Cys  Ser  Pro  Lys  Ser  Gln  Arg  Ala
     590                         595                         600

CTG  GTC  TAT  TGG  CAA  TTC  CAG  AGG  CGA  AAT  GAA  GAG  CGA  AAA  GAA  GAG     1875
Leu  Val  Tyr  Trp  Gln  Phe  Gln  Arg  Arg  Asn  Glu  Glu  Arg  Lys  Glu  Glu
605                      610                         615                         620

ATC  AGA  GTG  GAT  GAT  CAT  ATC  ATC  AGG  ACA  GAT  CAA  GGC  CTT  CTG  CTA     1923
Ile  Arg  Val  Asp  Asp  His  Ile  Ile  Arg  Thr  Asp  Gln  Gly  Leu  Leu  Leu
                    625                         630                         635

CGT  AGT  CTA  CAA  CAG  AAG  GAT  TCA  GGC  AAT  TAC  CTC  TGC  CAT  GCG  GTG     1971
Arg  Ser  Leu  Gln  Gln  Lys  Asp  Ser  Gly  Asn  Tyr  Leu  Cys  His  Ala  Val
               640                         645                         650

GAA  CAT  GGG  TTC  ATA  CAA  ACT  CTT  CTT  AAG  GTA  ACC  CTG  GAA  GTC  ATT     2019
Glu  His  Gly  Phe  Ile  Gln  Thr  Leu  Leu  Lys  Val  Thr  Leu  Glu  Val  Ile
          655                         660                         665

GAC  ACA  GAG  CAT  TTG  GAA  GAA  CTT  CTT  CAT  AAA  GAT  GAT  GAT  GGA  GAT     2067
Asp  Thr  Glu  His  Leu  Glu  Glu  Leu  Leu  His  Lys  Asp  Asp  Asp  Gly  Asp
     670                         675                         680

GGC  TCT  AAG  ACC  AAA  GAA  ATG  TCC  AAT  AGC  ATG  ACA  CCT  AGC  CAG  AAG     2115
Gly  Ser  Lys  Thr  Lys  Glu  Met  Ser  Asn  Ser  Met  Thr  Pro  Ser  Gln  Lys
685                      690                         695                         700

GTC  TGG  TAC  AGA  GAC  TTC  ATG  CAG  CTC  ATC  AAC  CAC  CCC  AAT  CTC  AAC     2163
Val  Trp  Tyr  Arg  Asp  Phe  Met  Gln  Leu  Ile  Asn  His  Pro  Asn  Leu  Asn
                    705                         710                         715

ACG  ATG  GAT  GAG  TTC  TGT  GAA  CAA  GTT  TGG  AAA  AGG  GAC  CGA  AAA  CAA     2211
Thr  Met  Asp  Glu  Phe  Cys  Glu  Gln  Val  Trp  Lys  Arg  Asp  Arg  Lys  Gln
               720                         725                         730

CGT  CGG  CAA  AGG  CCA  GGA  CAT  ACC  CCA  GGG  AAC  AGT  AAC  AAA  TGG  AAG     2259
Arg  Arg  Gln  Arg  Pro  Gly  His  Thr  Pro  Gly  Asn  Ser  Asn  Lys  Trp  Lys
               735                         740                         745

CAC  TTA  CAA  GAA  AAT  AAG  AAA  GGT  AGA  AAC  AGG  AGG  ACC  CAC  GAA  TTT     2307
His  Leu  Gln  Glu  Asn  Lys  Lys  Gly  Arg  Asn  Arg  Arg  Thr  His  Glu  Phe
          750                         755                         760

GAG  AGG  GCA  CCC  AGG  AGT  GTC  TGAGCTGCAT TACCTCTAGA AACCTCAAAC               2358
Glu  Arg  Ala  Pro  Arg  Ser  Val
765                      770

AAGTAGAAAC TTGCCTAGAC AATAACTGGA AAAACAAATG CAATATACAT GAACTTTTTT                 2418
```

```
CATGGCATTA  TGTGGATGTT  TACAATGGTG  GGAAATTCAG  CTGAGTTCCA  CCAATTATAA    2478

ATTAAATCCA  TGAGTAACTT  TCCTAATAGG  CTTTTTTTC   CTAATACCAC  CGGGTTAAAA    2538

GTAAGAGACA  GCTGAACCCT  CGTGGAGCCA  TTCATACAGG  TCCCTATTTA  AGGAACGGAA    2598

TTC                                                                      2601
```

( 2 ) INFORMATION FOR SEQ ID NO:54:

( i ) SEQUENCE CHARACTERISTICS:
      ( A ) LENGTH: 771 amino acids
      ( B ) TYPE: amino acid
      ( D ) TOPOLOGY: linear ( i i ) MOLECULE TYPE: protein ( x i ) SEQUENCE DESCRIPTION: SEQ ID NO:54:

```
Met  Gly  Trp  Leu  Thr  Arg  Ile  Val  Cys  Leu  Phe  Trp  Gly  Val  Leu  Leu
 1              5                        10                       15

Thr  Ala  Arg  Ala  Asn  Tyr  Gln  Asn  Gly  Lys  Asn  Asn  Val  Pro  Arg  Leu
              20                       25                       30

Lys  Leu  Ser  Tyr  Lys  Glu  Met  Leu  Glu  Ser  Asn  Asn  Val  Ile  Thr  Phe
         35                       40                       45

Asn  Gly  Leu  Ala  Asn  Ser  Ser  Tyr  His  Thr  Phe  Leu  Leu  Asp  Glu
     50                       55                       60

Glu  Arg  Ser  Arg  Leu  Tyr  Val  Gly  Ala  Lys  Asp  His  Ile  Phe  Ser  Phe
 65                       70                       75                       80

Asp  Leu  Val  Asn  Ile  Lys  Asp  Phe  Gln  Lys  Ile  Val  Trp  Pro  Val  Ser
                   85                       90                       95

Tyr  Thr  Arg  Arg  Asp  Glu  Cys  Lys  Trp  Ala  Gly  Lys  Asp  Ile  Leu  Lys
              100                      105                      110

Glu  Cys  Ala  Asn  Phe  Ile  Lys  Val  Leu  Lys  Ala  Tyr  Asn  Gln  Thr  His
              115                      120                      125

Leu  Tyr  Ala  Cys  Gly  Thr  Gly  Ala  Phe  His  Pro  Ile  Cys  Thr  Tyr  Ile
         130                      135                      140

Glu  Ile  Gly  His  His  Pro  Glu  Asp  Asn  Ile  Phe  Lys  Leu  Glu  Asn  Ser
145                      150                      155                      160

His  Phe  Glu  Asn  Gly  Arg  Gly  Lys  Ser  Pro  Tyr  Asp  Pro  Lys  Leu  Leu
                   165                      170                      175

Thr  Ala  Ser  Leu  Leu  Ile  Asp  Gly  Glu  Leu  Tyr  Ser  Gly  Thr  Ala  Ala
              180                      185                      190

Asp  Phe  Met  Gly  Arg  Asp  Phe  Ala  Ile  Phe  Arg  Thr  Leu  Gly  His  His
              195                      200                      205

His  Pro  Ile  Arg  Thr  Glu  Gln  His  Asp  Ser  Arg  Trp  Leu  Asn  Asp  Pro
         210                      215                      220

Lys  Phe  Ile  Ser  Ala  His  Leu  Ile  Ser  Glu  Ser  Asp  Asn  Pro  Glu  Asp
225                      230                      235                      240

Asp  Lys  Val  Tyr  Phe  Phe  Phe  Arg  Glu  Asn  Ala  Ile  Asp  Gly  Glu  His
                   245                      250                      255

Ser  Gly  Lys  Ala  Thr  His  Ala  Arg  Ile  Gly  Gln  Ile  Cys  Lys  Asn  Asp
              260                      265                      270

Phe  Gly  Gly  His  Arg  Ser  Leu  Val  Asn  Lys  Trp  Thr  Thr  Phe  Leu  Lys
              275                      280                      285

Ala  Arg  Leu  Ile  Cys  Ser  Val  Pro  Gly  Pro  Asn  Gly  Ile  Asp  Thr  His
         290                      295                      300

Phe  Asp  Glu  Leu  Gln  Asp  Val  Phe  Leu  Met  Asn  Phe  Lys  Asp  Pro  Lys
305                      310                      315                      320
```

```
Asn Pro Val Val Tyr Gly Val Phe Thr Thr Ser Ser Asn Ile Phe Lys
            325             330             335

Gly Ser Ala Val Cys Met Tyr Ser Met Ser Asp Val Arg Arg Val Phe
            340             345             350

Leu Gly Pro Tyr Ala His Arg Asp Gly Pro Asn Tyr Gln Trp Val Pro
            355             360             365

Tyr Gln Gly Arg Val Pro Tyr Pro Arg Pro Gly Thr Cys Pro Ser Lys
    370             375             380

Thr Phe Gly Gly Phe Asp Ser Thr Lys Asp Leu Pro Asp Asp Val Ile
385             390             395             400

Thr Phe Ala Arg Ser His Pro Ala Met Tyr Asn Pro Val Phe Pro Met
            405             410             415

Asn Asn Arg Pro Ile Val Ile Lys Thr Asp Val Asn Tyr Gln Phe Thr
            420             425             430

Gln Ile Val Val Asp Arg Val Asp Ala Glu Asp Gly Gln Tyr Asp Val
            435             440             445

Met Phe Ile Gly Thr Asp Val Gly Thr Val Leu Lys Val Val Ser Ile
            450             455             460

Pro Lys Glu Thr Trp Tyr Asp Leu Glu Glu Val Leu Leu Glu Glu Met
465             470             475             480

Thr Val Phe Arg Glu Pro Thr Ala Ile Ser Ala Met Glu Leu Ser Thr
            485             490             495

Lys Gln Gln Gln Leu Tyr Ile Gly Ser Thr Ala Gly Val Ala Gln Leu
            500             505             510

Pro Leu His Arg Cys Asp Ile Tyr Gly Lys Ala Cys Ala Glu Cys Cys
            515             520             525

Leu Ala Arg Asp Pro Tyr Cys Ala Trp Asp Gly Ser Ala Cys Ser Arg
    530             535             540

Tyr Phe Pro Thr Ala Lys Arg Arg Thr Arg Arg Gln Asp Ile Arg Asn
545             550             555             560

Gly Asp Pro Leu Thr His Cys Ser Asp Leu His His Asp Asn His His
            565             570             575

Gly His Ser Pro Glu Glu Arg Ile Ile Tyr Gly Val Glu Asn Ser Ser
            580             585             590

Thr Phe Leu Glu Cys Ser Pro Lys Ser Gln Arg Ala Leu Val Tyr Trp
    595             600             605

Gln Phe Gln Arg Arg Asn Glu Glu Arg Lys Glu Glu Ile Arg Val Asp
    610             615             620

Asp His Ile Ile Arg Thr Asp Gln Gly Leu Leu Leu Arg Ser Leu Gln
625             630             635             640

Gln Lys Asp Ser Gly Asn Tyr Leu Cys His Ala Val Glu His Gly Phe
            645             650             655

Ile Gln Thr Leu Leu Lys Val Thr Leu Glu Val Ile Asp Thr Glu His
            660             665             670

Leu Glu Glu Leu Leu His Lys Asp Asp Gly Asp Gly Ser Lys Thr
    675             680             685

Lys Glu Met Ser Asn Ser Met Thr Pro Ser Gln Lys Val Trp Tyr Arg
    690             695             700

Asp Phe Met Gln Leu Ile Asn His Pro Asn Leu Asn Thr Met Asp Glu
705             710             715             720

Phe Cys Glu Gln Val Trp Lys Arg Asp Arg Lys Gln Arg Arg Gln Arg
            725             730             735

Pro Gly His Thr Pro Gly Asn Ser Asn Lys Trp Lys His Leu Gln Glu
            740             745             750
```

Asn Lys Lys Gly Arg Asn Arg Arg Thr His Glu Phe Glu Arg Ala Pro
         755                 760                 765

Arg Ser Val
    770

( 2 ) INFORMATION FOR SEQ ID NO:55:

( i ) SEQUENCE CHARACTERISTICS:
        ( A ) LENGTH: 1332 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 7..1329

( x i ) SEQUENCE DESCRIPTION: SEQ ID NO:55:

```
GGAATA ATG ATG GTA TTA TTA CAT GCT GTA TAC TCT ATA GTC TTT GTA          48
       Met Met Val Leu Leu His Ala Val Tyr Ser Ile Val Phe Val
         1           5                      10

GAT GTT ATA ATC ATA AAA GTA CAG AGG TAT ATC AAC GAT ATT CTA ACT          96
Asp Val Ile Ile Ile Lys Val Gln Arg Tyr Ile Asn Asp Ile Leu Thr
 15              20                  25                      30

CTT GAC ATT TTT TAT TTA TTT AAA ATG ATA CCT TTG TTA TTT ATT TTA         144
Leu Asp Ile Phe Tyr Leu Phe Lys Met Ile Pro Leu Leu Phe Ile Leu
                 35                  40                  45

TTC TAT TTT GCT AAC GGT ATC GAA TGG CAT AAG TTT GAA ACG AGT GAA         192
Phe Tyr Phe Ala Asn Gly Ile Glu Trp His Lys Phe Glu Thr Ser Glu
             50                  55                  60

GAA ATA ATT TCT ACT TAC TTA TTA GAC GAC GTA TTA TAC ACG GGT GTT         240
Glu Ile Ile Ser Thr Tyr Leu Leu Asp Asp Val Leu Tyr Thr Gly Val
         65                  70                  75

AAT GGG GCG GTA TAC ACA TTT TCA AAT AAT AAA CTA AAC AAA ACT GGT         288
Asn Gly Ala Val Tyr Thr Phe Ser Asn Asn Lys Leu Asn Lys Thr Gly
     80                  85                  90

TTA ACT AAT AAT AAT TAT ATA ACA ACA TCT ATA AAA GTA GAG GAT GCG         336
Leu Thr Asn Asn Asn Tyr Ile Thr Thr Ser Ile Lys Val Glu Asp Ala
 95                 100                 105                 110

GAT AAG GAT ACA TTA GTA TGC GGA ACC AAT AAC GGA AAT CCC AAA TGT         384
Asp Lys Asp Thr Leu Val Cys Gly Thr Asn Asn Gly Asn Pro Lys Cys
                115                 120                 125

TGG AAA ATA GAC GGT TCA GAC GAC CCA AAA CAT AGA GGT AGA GGA TAC         432
Trp Lys Ile Asp Gly Ser Asp Asp Pro Lys His Arg Gly Arg Gly Tyr
            130                 135                 140

GCT CCT TAT CAA AAT AGC AAA GTA ACG ATA ATC AGT CAC AAC GGA TGT         480
Ala Pro Tyr Gln Asn Ser Lys Val Thr Ile Ile Ser His Asn Gly Cys
        145                 150                 155

GTA CTA TCT GAC ATA AAC ATA TCA AAA GAA GGA ATT AAA CGA TGG AGA         528
Val Leu Ser Asp Ile Asn Ile Ser Lys Glu Gly Ile Lys Arg Trp Arg
    160                 165                 170

AGA TTT GAC GGA CCA TGT GGT TAT GAT TTA TAC ACG GCG GAT AAC GTA         576
Arg Phe Asp Gly Pro Cys Gly Tyr Asp Leu Tyr Thr Ala Asp Asn Val
175                 180                 185                 190

ATT CCA AAA GAT GGT TTA CGA GGA GCA TTC GTC GAT AAA GAT GGT ACT         624
Ile Pro Lys Asp Gly Leu Arg Gly Ala Phe Val Asp Lys Asp Gly Thr
                195                 200                 205

TAT GAC AAA GTT TAC ATT CTT TTC ACT GAT ACT ATC GGC TCA AAG AGA         672
Tyr Asp Lys Val Tyr Ile Leu Phe Thr Asp Thr Ile Gly Ser Lys Arg
            210                 215                 220
```

```
ATT  GTC  AAA  ATT  CCG  TAT  ATA  GCA  CAA  ATG  TGC  CTA  AAC  GAC  GAA  GGT        720
Ile  Val  Lys  Ile  Pro  Tyr  Ile  Ala  Gln  Met  Cys  Leu  Asn  Asp  Glu  Gly
          225                      230                     235

GGT  CCA  TCA  TCA  TTG  TCT  AGT  CAT  AGA  TGG  TCG  ACG  TTT  CTC  AAA  GTC        768
Gly  Pro  Ser  Ser  Leu  Ser  Ser  His  Arg  Trp  Ser  Thr  Phe  Leu  Lys  Val
     240                      245                     250

GAA  TTA  GAA  TGT  GAT  ATC  GAC  GGA  AGA  AGT  TAT  AGA  CAA  ATT  ATT  CAT        816
Glu  Leu  Glu  Cys  Asp  Ile  Asp  Gly  Arg  Ser  Tyr  Arg  Gln  Ile  Ile  His
255                      260                     265                     270

TCT  AGA  ACT  ATA  AAA  ACA  GAT  AAT  GAT  ACG  ATA  CTA  TAT  GTA  TTC  TTC        864
Ser  Arg  Thr  Ile  Lys  Thr  Asp  Asn  Asp  Thr  Ile  Leu  Tyr  Val  Phe  Phe
                    275                     280                     285

GAT  AGT  CCT  TAT  TCC  AAG  TCC  GCA  TTA  TGT  ACC  TAT  TCT  ATG  AAT  ACC        912
Asp  Ser  Pro  Tyr  Ser  Lys  Ser  Ala  Leu  Cys  Thr  Tyr  Ser  Met  Asn  Thr
               290                     295                     300

ATT  AAA  CAA  TCT  TTT  TCT  ACG  TCA  AAA  TTG  GAA  GGA  TAT  ACA  AAG  CAA        960
Ile  Lys  Gln  Ser  Phe  Ser  Thr  Ser  Lys  Leu  Glu  Gly  Tyr  Thr  Lys  Gln
          305                     310                     315

TTG  CCG  TCG  CCA  GCC  TCT  GGT  ATA  TGT  CTA  CCA  GCT  GGA  AAA  GTT  GTT       1008
Leu  Pro  Ser  Pro  Ala  Ser  Gly  Ile  Cys  Leu  Pro  Ala  Gly  Lys  Val  Val
     320                      325                     330

CCA  CAT  ACC  ACG  TTT  GAA  GTC  ATA  GAA  AAA  TAT  AAT  GTA  CTA  GAT  GAT       1056
Pro  His  Thr  Thr  Phe  Glu  Val  Ile  Glu  Lys  Tyr  Asn  Val  Leu  Asp  Asp
335                      340                     345                     350

ATT  ATA  AAG  CCT  TTA  TCT  AAC  CAA  CCT  ATC  TTC  GAA  GGA  CCG  TCT  GGT       1104
Ile  Ile  Lys  Pro  Leu  Ser  Asn  Gln  Pro  Ile  Phe  Glu  Gly  Pro  Ser  Gly
                    355                     360                     365

GTT  AAA  TGG  TTC  GAT  ATA  AAG  GAG  AAG  GAA  AAT  GAA  CAT  CGG  GAA  TAT       1152
Val  Lys  Trp  Phe  Asp  Ile  Lys  Glu  Lys  Glu  Asn  Glu  His  Arg  Glu  Tyr
               370                     375                     380

AGA  ATA  TAC  TTC  ATA  AAA  GAA  AAT  TCT  ATA  TAT  TCG  TTC  GAT  ACA  AAA       1200
Arg  Ile  Tyr  Phe  Ile  Lys  Glu  Asn  Ser  Ile  Tyr  Ser  Phe  Asp  Thr  Lys
          385                     390                     395

TCT  AAA  CAA  ACT  CGT  AGC  TCG  CAA  GTC  GAT  GCG  CGA  CTA  TTT  TCA  GTA       1248
Ser  Lys  Gln  Thr  Arg  Ser  Ser  Gln  Val  Asp  Ala  Arg  Leu  Phe  Ser  Val
     400                      405                     410

ATG  GTA  ACT  TCG  AAA  CCG  TTA  TTT  ATA  GCA  GAT  ATA  GGG  ATA  GGA  GTA       1296
Met  Val  Thr  Ser  Lys  Pro  Leu  Phe  Ile  Ala  Asp  Ile  Gly  Ile  Gly  Val
415                      420                     425                     430

GGA  ATG  CCA  CAA  ATG  AAA  AAA  ATA  CTT  AAA  ATG  TAA                            1332
Gly  Met  Pro  Gln  Met  Lys  Lys  Ile  Leu  Lys  Met
                    435                     440
```

( 2 ) INFORMATION FOR SEQ ID NO:56:

( i ) SEQUENCE CHARACTERISTICS:
        ( A ) LENGTH: 441 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

```
Met  Met  Val  Leu  Leu  His  Ala  Val  Tyr  Ser  Ile  Val  Phe  Val  Asp  Val
1                   5                        10                       15

Ile  Ile  Ile  Lys  Val  Gln  Arg  Tyr  Ile  Asn  Asp  Ile  Leu  Thr  Leu  Asp
               20                       25                       30

Ile  Phe  Tyr  Leu  Phe  Lys  Met  Ile  Pro  Leu  Leu  Phe  Ile  Leu  Phe  Tyr
          35                       40                       45

Phe  Ala  Asn  Gly  Ile  Glu  Trp  His  Lys  Phe  Glu  Thr  Ser  Glu  Glu  Ile
     50                       55                       60
```

| Ile | Ser | Thr | Tyr | Leu | Leu | Asp | Asp | Val | Leu | Tyr | Thr | Gly | Val | Asn | Gly |
| 65 | | | | 70 | | | | | 75 | | | | | | 80 |

| Ala | Val | Tyr | Thr | Phe | Ser | Asn | Asn | Lys | Leu | Asn | Lys | Thr | Gly | Leu | Thr |
| | | | | 85 | | | | | 90 | | | | | 95 | |

| Asn | Asn | Asn | Tyr | Ile | Thr | Thr | Ser | Ile | Lys | Val | Glu | Asp | Ala | Asp | Lys |
| | | | 100 | | | | | 105 | | | | | 110 | | |

| Asp | Thr | Leu | Val | Cys | Gly | Thr | Asn | Asn | Gly | Asn | Pro | Lys | Cys | Trp | Lys |
| | | 115 | | | | | 120 | | | | | 125 | | | |

| Ile | Asp | Gly | Ser | Asp | Asp | Pro | Lys | His | Arg | Gly | Arg | Gly | Tyr | Ala | Pro |
| | 130 | | | | | 135 | | | | | 140 | | | | |

| Tyr | Gln | Asn | Ser | Lys | Val | Thr | Ile | Ile | Ser | His | Asn | Gly | Cys | Val | Leu |
| 145 | | | | | 150 | | | | | 155 | | | | | 160 |

| Ser | Asp | Ile | Asn | Ile | Ser | Lys | Glu | Gly | Ile | Lys | Arg | Trp | Arg | Arg | Phe |
| | | | | 165 | | | | | 170 | | | | | 175 | |

| Asp | Gly | Pro | Cys | Gly | Tyr | Asp | Leu | Tyr | Thr | Ala | Asp | Asn | Val | Ile | Pro |
| | | | 180 | | | | | 185 | | | | | 190 | | |

| Lys | Asp | Gly | Leu | Arg | Gly | Ala | Phe | Val | Asp | Lys | Asp | Gly | Thr | Tyr | Asp |
| | | 195 | | | | | 200 | | | | | 205 | | | |

| Lys | Val | Tyr | Ile | Leu | Phe | Thr | Asp | Thr | Ile | Gly | Ser | Lys | Arg | Ile | Val |
| | 210 | | | | | 215 | | | | | 220 | | | | |

| Lys | Ile | Pro | Tyr | Ile | Ala | Gln | Met | Cys | Leu | Asn | Asp | Glu | Gly | Gly | Pro |
| 225 | | | | | 230 | | | | | 235 | | | | | 240 |

| Ser | Ser | Leu | Ser | Ser | His | Arg | Trp | Ser | Thr | Phe | Leu | Lys | Val | Glu | Leu |
| | | | | 245 | | | | | 250 | | | | | 255 | |

| Glu | Cys | Asp | Ile | Asp | Gly | Arg | Ser | Tyr | Arg | Gln | Ile | Ile | His | Ser | Arg |
| | | | 260 | | | | | 265 | | | | | 270 | | |

| Thr | Ile | Lys | Thr | Asp | Asn | Asp | Thr | Ile | Leu | Tyr | Val | Phe | Phe | Asp | Ser |
| | | 275 | | | | | 280 | | | | | 285 | | | |

| Pro | Tyr | Ser | Lys | Ser | Ala | Leu | Cys | Thr | Tyr | Ser | Met | Asn | Thr | Ile | Lys |
| | 290 | | | | | 295 | | | | | 300 | | | | |

| Gln | Ser | Phe | Ser | Thr | Ser | Lys | Leu | Glu | Gly | Tyr | Thr | Lys | Gln | Leu | Pro |
| 305 | | | | | 310 | | | | | 315 | | | | | 320 |

| Ser | Pro | Ala | Ser | Gly | Ile | Cys | Leu | Pro | Ala | Gly | Lys | Val | Val | Pro | His |
| | | | | 325 | | | | | 330 | | | | | 335 | |

| Thr | Thr | Phe | Glu | Val | Ile | Glu | Lys | Tyr | Asn | Val | Leu | Asp | Asp | Ile | Ile |
| | | | 340 | | | | | 345 | | | | | 350 | | |

| Lys | Pro | Leu | Ser | Asn | Gln | Pro | Ile | Phe | Glu | Gly | Pro | Ser | Gly | Val | Lys |
| | | 355 | | | | | 360 | | | | | 365 | | | |

| Trp | Phe | Asp | Ile | Lys | Glu | Lys | Glu | Asn | Glu | His | Arg | Glu | Tyr | Arg | Ile |
| | 370 | | | | | 375 | | | | | 380 | | | | |

| Tyr | Phe | Ile | Lys | Glu | Asn | Ser | Ile | Tyr | Ser | Phe | Asp | Thr | Lys | Ser | Lys |
| 385 | | | | | 390 | | | | | 395 | | | | | 400 |

| Gln | Thr | Arg | Ser | Ser | Gln | Val | Asp | Ala | Arg | Leu | Phe | Ser | Val | Met | Val |
| | | | | 405 | | | | | 410 | | | | | 415 | |

| Thr | Ser | Lys | Pro | Leu | Phe | Ile | Ala | Asp | Ile | Gly | Ile | Gly | Val | Gly | Met |
| | | | 420 | | | | | 425 | | | | | 430 | | |

| Pro | Gln | Met | Lys | Lys | Ile | Leu | Lys | Met |
| | | 435 | | | | | 440 | |

(2) INFORMATION FOR SEQ ID NO:57:

(i) SEQUENCE CHARACTERISTICS:
(A) LENGTH: 2854 base pairs
(B) TYPE: nucleic acid
(C) STRANDEDNESS: double
(D) TOPOLOGY: linear (ii) MOLECULE TYPE: cDNA (ix) FEATURE:
    (A) NAME/KEY: CDS
    (B) LOCATION: 451..2640

(xi) SEQUENCE DESCRIPTION: SEQ ID NO:57:

```
ATTCCACCTC CCGCTGACCG CCTACGCCGC GACGATCTTT CCTCTCGCCA GGCGAAAACT          60

ACGACGTGTC AACAACATTT TTGTTTTTTC TGCTTCCGTG TTTTCATGTT CCGTGAAACC         120

GCTTCTCGCA TTACCACTCT TCCGTTTCCC AGTGTTTGTT TTCTCCGTTT CTTTCATCGT         180

GGATGTTTTG TTTTGGTGTA GCGAGTGACG AGCTTATGTC ATTAAACGTA CATCCAATCT         240

GTCGGTATAT TGGTGTGTGA TATTTACTA  TTATATATTT AGCCATCACT TGAAAGCCGT         300

GAAAAATTTT TGAAAGTGGA GAGGAAAAAG AAAAGGCGCA GAAGGCTTTT TAAGCTTCAT         360

GGATATGTGC TCTACGCTTC AACTACTGTC GCAGAATCAT CTTCCGGGAA AGGAAATTTC         420

GCCTGAAATG GTGCCGCGGC CGCACTGAAC ATG CGG GCG GCG CTG GTG GCC GTC         474
                                  Met Arg Ala Ala Leu Val Ala Val
                                    1               5

GCG GCG CTG CTT TGG GTG GCG CTG CAC GCC GCC GCA TGG GTC AAC GAC          522
Ala Ala Leu Leu Trp Val Ala Leu His Ala Ala Ala Trp Val Asn Asp
         10                  15                  20

GTC AGC CCC AAG ATG TAC GTC CAG TTC GGT GAG GAA CGG GTG CAA CGC          570
Val Ser Pro Lys Met Tyr Val Gln Phe Gly Glu Glu Arg Val Gln Arg
 25                  30                  35                  40

TTC CTG GGC AAT GAA TCG CAC AAA GAC CAC TTC AAG CTG CTG GAG AAG          618
Phe Leu Gly Asn Glu Ser His Lys Asp His Phe Lys Leu Leu Glu Lys
                 45                  50                  55

GAC CAC AAC TCG CTC CTC GTA GGA GCT AGG AAC ATC GTC TAC AAT ATC          666
Asp His Asn Ser Leu Leu Val Gly Ala Arg Asn Ile Val Tyr Asn Ile
             60                  65                  70

AGC CTT CGA GAC CTC ACA GAA TTC ACC GAG CAG AGG ATC GAG TGG CAC          714
Ser Leu Arg Asp Leu Thr Glu Phe Thr Glu Gln Arg Ile Glu Trp His
         75                  80                  85

TCG TCA GGT GCC CAT CGC GAG CTC TGC TAC CTC AAG GGG AAG TCA GAG          762
Ser Ser Gly Ala His Arg Glu Leu Cys Tyr Leu Lys Gly Lys Ser Glu
     90                  95                 100

GAC GAC TGC CAG AAC TAC ATC CGA GTC CTG GCG AAA ATT GAC GAT GAC          810
Asp Asp Cys Gln Asn Tyr Ile Arg Val Leu Ala Lys Ile Asp Asp Asp
105                 110                 115                 120

CGC GTA CTC ATC TGC GGT ACG AAC GCC TAT AAG CCA CTA TGT CGG CAC          858
Arg Val Leu Ile Cys Gly Thr Asn Ala Tyr Lys Pro Leu Cys Arg His
                125                 130                 135

TAC GCC CTC AAG GAT GGA GAT TAT GTT GTA GAG AAA GAA TAT GAG GGA          906
Tyr Ala Leu Lys Asp Gly Asp Tyr Val Val Glu Lys Glu Tyr Glu Gly
            140                 145                 150

AGA GGA TTG TGC CCA TTT GAC CCT GAC CAC AAC AGC ACT GCA ATA TAC          954
Arg Gly Leu Cys Pro Phe Asp Pro Asp His Asn Ser Thr Ala Ile Tyr
        155                 160                 165

AGT GAG GGA CAA TTG TAC TCA GCA ACA GTG GCA GAC TTC TCT GGA ACT         1002
Ser Glu Gly Gln Leu Tyr Ser Ala Thr Val Ala Asp Phe Ser Gly Thr
    170                 175                 180

GAC CCT CTC ATA TAC CGC GGC CCT CTA AGA ACA GAG AGA TCT GAC CTC         1050
Asp Pro Leu Ile Tyr Arg Gly Pro Leu Arg Thr Glu Arg Ser Asp Leu
185                 190                 195                 200

AAA CAA TTA AAT GCT CCT AAC TTT GTC AAC ACA ATG GAG TAC AAT GAT         1098
Lys Gln Leu Asn Ala Pro Asn Phe Val Asn Thr Met Glu Tyr Asn Asp
                205                 210                 215

TTT ATA TTC TTC TTC TTC CGA GAG ACT GCT GTT GAG TAC ATC AAC TGC         1146
```

|  |  |  |  |  |  |  |  |  |  |  |  |  |  |  |  |
|---|---|---|---|---|---|---|---|---|---|---|---|---|---|---|---|
| Phe | Ile | Phe | Phe | Phe | Phe | Arg | Glu | Thr | Ala | Val | Glu | Tyr | Ile | Asn | Cys |
|  |  |  | 220 |  |  |  | 225 |  |  |  |  |  | 230 |  |  |

| GGA | AAG | GCT | ATC | TAT | TCA | AGA | GTT | GCC | AGA | GTC | TGT | AAA | CAT | GAC | AAG | 1194 |
|---|---|---|---|---|---|---|---|---|---|---|---|---|---|---|---|---|
| Gly | Lys | Ala | Ile | Tyr | Ser | Arg | Val | Ala | Arg | Val | Cys | Lys | His | Asp | Lys |  |
|  |  | 235 |  |  |  | 240 |  |  |  |  | 245 |  |  |  |  |  |

| GGC | GGC | CCT | CAT | CAG | GGT | GGT | GAC | AGA | TGG | ACT | TCT | TTT | TTG | AAA | TCA | 1242 |
|---|---|---|---|---|---|---|---|---|---|---|---|---|---|---|---|---|
| Gly | Gly | Pro | His | Gln | Gly | Gly | Asp | Arg | Trp | Thr | Ser | Phe | Leu | Lys | Ser |  |
| 250 |  |  |  |  | 255 |  |  |  |  | 260 |  |  |  |  |  |  |

| CGT | CTG | AAC | TGT | TCC | GTC | CCT | GGA | GAT | TAT | CCA | TTT | TAC | TTC | AAT | GAA | 1290 |
|---|---|---|---|---|---|---|---|---|---|---|---|---|---|---|---|---|
| Arg | Leu | Asn | Cys | Ser | Val | Pro | Gly | Asp | Tyr | Pro | Phe | Tyr | Phe | Asn | Glu |  |
| 265 |  |  |  |  | 270 |  |  |  |  | 275 |  |  |  |  | 280 |  |

| ATT | CAG | TCA | ACA | AGT | GAC | ATC | ATT | GAA | GGA | AAT | TAT | GGT | GGT | CAA | GTG | 1338 |
|---|---|---|---|---|---|---|---|---|---|---|---|---|---|---|---|---|
| Ile | Gln | Ser | Thr | Ser | Asp | Ile | Ile | Glu | Gly | Asn | Tyr | Gly | Gly | Gln | Val |  |
|  |  |  |  | 285 |  |  |  |  | 290 |  |  |  |  | 295 |  |  |

| GAG | AAA | CTC | ATC | TAC | GGT | GTC | TTC | ACG | ACA | CCA | GTG | AAC | TCT | ATT | GGT | 1386 |
|---|---|---|---|---|---|---|---|---|---|---|---|---|---|---|---|---|
| Glu | Lys | Leu | Ile | Tyr | Gly | Val | Phe | Thr | Thr | Pro | Val | Asn | Ser | Ile | Gly |  |
|  |  |  | 300 |  |  |  |  | 305 |  |  |  |  | 310 |  |  |  |

| GGC | TCT | GCT | GTT | TGT | GCC | TTC | AGT | ATG | AAG | TCA | ATA | CTT | GAG | TCA | TTT | 1434 |
|---|---|---|---|---|---|---|---|---|---|---|---|---|---|---|---|---|
| Gly | Ser | Ala | Val | Cys | Ala | Phe | Ser | Met | Lys | Ser | Ile | Leu | Glu | Ser | Phe |  |
|  |  | 315 |  |  |  |  | 320 |  |  |  |  | 325 |  |  |  |  |

| GAT | GGT | CCA | TTT | AAA | GAG | CAG | GAA | ACG | ATG | AAC | TCA | AAC | TGG | TTG | GCA | 1482 |
|---|---|---|---|---|---|---|---|---|---|---|---|---|---|---|---|---|
| Asp | Gly | Pro | Phe | Lys | Glu | Gln | Glu | Thr | Met | Asn | Ser | Asn | Trp | Leu | Ala |  |
|  | 330 |  |  |  |  | 335 |  |  |  |  | 340 |  |  |  |  |  |

| GTG | CCA | AGC | CTT | AAA | GTG | CCA | GAA | CCA | AGG | CCT | GGA | CAA | TGT | GTG | AAT | 1530 |
|---|---|---|---|---|---|---|---|---|---|---|---|---|---|---|---|---|
| Val | Pro | Ser | Leu | Lys | Val | Pro | Glu | Pro | Arg | Pro | Gly | Gln | Cys | Val | Asn |  |
| 345 |  |  |  | 350 |  |  |  |  | 355 |  |  |  |  |  | 360 |  |

| GAC | AGT | CGT | ACA | CTT | CCT | GAT | GTG | TCT | GTC | AAT | TTT | GTA | AAG | TCA | CAT | 1578 |
|---|---|---|---|---|---|---|---|---|---|---|---|---|---|---|---|---|
| Asp | Ser | Arg | Thr | Leu | Pro | Asp | Val | Ser | Val | Asn | Phe | Val | Lys | Ser | His |  |
|  |  |  |  | 365 |  |  |  |  | 370 |  |  |  |  | 375 |  |  |

| ACA | CTG | ATG | GAT | GAG | GCC | GTG | CCA | GCA | TTT | TTT | ACT | CGG | CCA | ATT | CTC | 1626 |
|---|---|---|---|---|---|---|---|---|---|---|---|---|---|---|---|---|
| Thr | Leu | Met | Asp | Glu | Ala | Val | Pro | Ala | Phe | Phe | Thr | Arg | Pro | Ile | Leu |  |
|  |  |  | 380 |  |  |  |  | 385 |  |  |  |  | 390 |  |  |  |

| ATT | CGG | ATC | AGC | TTA | CAG | TAC | AGA | TTT | ACA | AAA | ATA | GCT | GTT | GAT | CAA | 1674 |
|---|---|---|---|---|---|---|---|---|---|---|---|---|---|---|---|---|
| Ile | Arg | Ile | Ser | Leu | Gln | Tyr | Arg | Phe | Thr | Lys | Ile | Ala | Val | Asp | Gln |  |
|  |  | 395 |  |  |  |  | 400 |  |  |  |  | 405 |  |  |  |  |

| CAA | GTC | CGA | ACA | CCA | GAT | GGG | AAA | GCG | TAT | GAT | GTC | CTG | TTT | ATA | GGA | 1722 |
|---|---|---|---|---|---|---|---|---|---|---|---|---|---|---|---|---|
| Gln | Val | Arg | Thr | Pro | Asp | Gly | Lys | Ala | Tyr | Asp | Val | Leu | Phe | Ile | Gly |  |
|  | 410 |  |  |  |  | 415 |  |  |  |  | 420 |  |  |  |  |  |

| ACT | GAT | GAT | GGC | AAA | GTG | ATA | AAA | GCT | TTG | AAC | TCT | GCC | TCC | TTT | GAT | 1770 |
|---|---|---|---|---|---|---|---|---|---|---|---|---|---|---|---|---|
| Thr | Asp | Asp | Gly | Lys | Val | Ile | Lys | Ala | Leu | Asn | Ser | Ala | Ser | Phe | Asp |  |
| 425 |  |  |  |  | 430 |  |  |  |  | 435 |  |  |  |  | 440 |  |

| TCA | TCT | GAT | ACT | GTA | GAT | AGT | GTT | GTA | ATA | GAA | GAA | CTG | CAA | GTG | TTG | 1818 |
|---|---|---|---|---|---|---|---|---|---|---|---|---|---|---|---|---|
| Ser | Ser | Asp | Thr | Val | Asp | Ser | Val | Val | Ile | Glu | Glu | Leu | Gln | Val | Leu |  |
|  |  |  |  | 445 |  |  |  |  | 450 |  |  |  |  | 455 |  |  |

| CCA | CCT | GGA | GTA | CCT | GTT | AAG | AAC | CTG | TAT | GTG | GTG | CGA | ATG | GAT | GGG | 1866 |
|---|---|---|---|---|---|---|---|---|---|---|---|---|---|---|---|---|
| Pro | Pro | Gly | Val | Pro | Val | Lys | Asn | Leu | Tyr | Val | Val | Arg | Met | Asp | Gly |  |
|  |  |  | 460 |  |  |  |  | 465 |  |  |  |  | 470 |  |  |  |

| GAT | GAT | AGC | AAG | CTG | GTG | GTT | GTG | TCT | GAT | GAT | GAG | ATT | CTG | GCA | ATT | 1914 |
|---|---|---|---|---|---|---|---|---|---|---|---|---|---|---|---|---|
| Asp | Asp | Ser | Lys | Leu | Val | Val | Val | Ser | Asp | Asp | Glu | Ile | Leu | Ala | Ile |  |
|  |  | 475 |  |  |  |  | 480 |  |  |  |  | 485 |  |  |  |  |

| AAG | CTT | CAT | CGT | TGT | GGC | TCA | GAT | AAA | ATA | ACA | AAT | TGT | CGA | GAA | TGT | 1962 |
|---|---|---|---|---|---|---|---|---|---|---|---|---|---|---|---|---|
| Lys | Leu | His | Arg | Cys | Gly | Ser | Asp | Lys | Ile | Thr | Asn | Cys | Arg | Glu | Cys |  |
|  | 490 |  |  |  |  | 495 |  |  |  |  | 500 |  |  |  |  |  |

| GTG | TCC | TTG | CAA | GAT | CCT | TAC | TGT | GCA | TGG | GAC | AAT | GTA | GAA | TTA | AAA | 2010 |
|---|---|---|---|---|---|---|---|---|---|---|---|---|---|---|---|---|
| Val | Ser | Leu | Gln | Asp | Pro | Tyr | Cys | Ala | Trp | Asp | Asn | Val | Glu | Leu | Lys |  |
| 505 |  |  |  |  | 510 |  |  |  |  | 515 |  |  |  |  | 520 |  |

| TGT | ACA | GCT | GTA | GGT | TCA | CCA | GAC | TGG | AGT | GCT | GGA | AAA | AGA | CGC | TTT | 2058 |
|---|---|---|---|---|---|---|---|---|---|---|---|---|---|---|---|---|
| Cys | Thr | Ala | Val | Gly | Ser | Pro | Asp | Trp | Ser | Ala | Gly | Lys | Arg | Arg | Phe |  |
|  |  |  |  | 525 |  |  |  |  | 530 |  |  |  |  | 535 |  |  |

| ATT | CAG | AAC | ATT | TCA | CTC | GGT | GAA | CAT | AAA | GCT | TGT | GGT | GGA | CGT | CCA | 2106 |
|---|---|---|---|---|---|---|---|---|---|---|---|---|---|---|---|---|

|  |  |  |  |  |  |  |  |  |  |  |  |  |  |  |  |
|---|---|---|---|---|---|---|---|---|---|---|---|---|---|---|---|
| Ile | Gln | Asn | Ile | Ser | Leu | Gly | Glu | His | Lys | Ala | Cys | Gly | Gly | Arg | Pro |
|  |  |  | 540 |  |  |  |  | 545 |  |  |  |  | 550 |  |  |

| CAA | ACA | GAA | ATC | GTT | GCT | TCT | CCT | GTA | CCA | ACT | CAG | CCG | ACG | ACA | AAA | 2154 |
|---|---|---|---|---|---|---|---|---|---|---|---|---|---|---|---|---|
| Gln | Thr | Glu | Ile | Val | Ala | Ser | Pro | Val | Pro | Thr | Gln | Pro | Thr | Thr | Lys |  |
|  |  | 555 |  |  |  |  | 560 |  |  |  |  | 565 |  |  |  |  |

| TCT | AGT | GGC | GAT | CCC | GTT | CAT | TCA | ATC | CAC | CAG | GCT | GAA | TTT | GAA | CCT | 2202 |
|---|---|---|---|---|---|---|---|---|---|---|---|---|---|---|---|---|
| Ser | Ser | Gly | Asp | Pro | Val | His | Ser | Ile | His | Gln | Ala | Glu | Phe | Glu | Pro |  |
|  | 570 |  |  |  |  | 575 |  |  |  |  | 580 |  |  |  |  |  |

| GAA | ATT | GAC | AAC | GAG | ATT | GTT | ATT | GGA | GTA | GAT | GAC | AGC | AAC | GTC | ATT | 2250 |
|---|---|---|---|---|---|---|---|---|---|---|---|---|---|---|---|---|
| Glu | Ile | Asp | Asn | Glu | Ile | Val | Ile | Gly | Val | Asp | Asp | Ser | Asn | Val | Ile |  |
| 585 |  |  |  |  | 590 |  |  |  |  | 595 |  |  |  |  | 600 |  |

| CCT | AAT | ACC | CTG | GCT | GAA | ATA | AAT | CAT | GCA | GGT | TCA | AAG | CTG | CCT | TCC | 2298 |
|---|---|---|---|---|---|---|---|---|---|---|---|---|---|---|---|---|
| Pro | Asn | Thr | Leu | Ala | Glu | Ile | Asn | His | Ala | Gly | Ser | Lys | Leu | Pro | Ser |  |
|  |  |  |  | 605 |  |  |  |  | 610 |  |  |  |  | 615 |  |  |

| TCC | CAG | GAA | AAG | TTG | CCT | ATT | TAT | ACA | GCG | GAG | ACT | CTG | ACT | ATT | GCT | 2346 |
|---|---|---|---|---|---|---|---|---|---|---|---|---|---|---|---|---|
| Ser | Gln | Glu | Lys | Leu | Pro | Ile | Tyr | Thr | Ala | Glu | Thr | Leu | Thr | Ile | Ala |  |
|  |  |  | 620 |  |  |  |  | 625 |  |  |  |  | 630 |  |  |  |

| ATA | GTT | ACA | TCA | TGC | CTT | GGA | GCT | CTA | GTT | GTT | GGC | TTC | ATC | TCT | GGA | 2394 |
|---|---|---|---|---|---|---|---|---|---|---|---|---|---|---|---|---|
| Ile | Val | Thr | Ser | Cys | Leu | Gly | Ala | Leu | Val | Val | Gly | Phe | Ile | Ser | Gly |  |
|  |  | 635 |  |  |  |  | 640 |  |  |  |  | 645 |  |  |  |  |

| TTT | CTT | TTT | TCT | CGG | CGA | TGC | AGG | GGA | GAG | GAT | TAC | ACA | GAC | ATG | CCT | 2442 |
|---|---|---|---|---|---|---|---|---|---|---|---|---|---|---|---|---|
| Phe | Leu | Phe | Ser | Arg | Arg | Cys | Arg | Gly | Glu | Asp | Tyr | Thr | Asp | Met | Pro |  |
|  | 650 |  |  |  |  | 655 |  |  |  |  | 660 |  |  |  |  |  |

| TTT | CCA | GAT | CAA | CGC | CAT | CAG | CTA | AAT | AGG | CTC | ACT | GAG | GCT | GGT | CTG | 2490 |
|---|---|---|---|---|---|---|---|---|---|---|---|---|---|---|---|---|
| Phe | Pro | Asp | Gln | Arg | His | Gln | Leu | Asn | Arg | Leu | Thr | Glu | Ala | Gly | Leu |  |
| 665 |  |  |  |  | 670 |  |  |  |  | 675 |  |  |  |  | 680 |  |

| AAT | GCA | GAC | TCA | CCC | TAT | CTT | CCA | CCC | TGT | GCC | AAT | AAC | AAG | GCA | GCC | 2538 |
|---|---|---|---|---|---|---|---|---|---|---|---|---|---|---|---|---|
| Asn | Ala | Asp | Ser | Pro | Tyr | Leu | Pro | Pro | Cys | Ala | Asn | Asn | Lys | Ala | Ala |  |
|  |  |  |  | 685 |  |  |  |  | 690 |  |  |  |  | 695 |  |  |

| ATA | AAT | CTT | GTG | CTC | AAT | GTC | CCA | CCA | AAG | AAT | GCA | AAT | GGA | AAA | AAT | 2586 |
|---|---|---|---|---|---|---|---|---|---|---|---|---|---|---|---|---|
| Ile | Asn | Leu | Val | Leu | Asn | Val | Pro | Pro | Lys | Asn | Ala | Asn | Gly | Lys | Asn |  |
|  |  |  | 700 |  |  |  |  | 705 |  |  |  |  | 710 |  |  |  |

| GCC | AAC | TCT | TCA | GCT | GAA | AAC | AAA | CCA | ATA | CAG | AAA | GTA | AAA | AAG | ACA | 2634 |
|---|---|---|---|---|---|---|---|---|---|---|---|---|---|---|---|---|
| Ala | Asn | Ser | Ser | Ala | Glu | Asn | Lys | Pro | Ile | Gln | Lys | Val | Lys | Lys | Thr |  |
|  |  | 715 |  |  |  |  | 720 |  |  |  |  | 725 |  |  |  |  |

| TAC | ATT | TAGCAGAAAT | CTTTGGTATC | TGTTTTGGTG | CAGACCCATG | CCACTAGAGT | 2690 |
|---|---|---|---|---|---|---|---|
| Tyr | Ile |  |  |  |  |  |  |
|  | 730 |  |  |  |  |  |  |

| AACCAAGACT | CTATTGAGAA | ATGTCCTCAA | GAAAGTTAAA | AAGATGTAGA | CTTCTGTAAT | 2750 |
|---|---|---|---|---|---|---|
| CGAGAGCACC | ACTTTCCATA | GTAATACAGA | ACAATGTGAA | ATAAATACTA | CAGAAGAAGT | 2810 |
| CTTTGTTACA | CAAAAAAGTG | TATAGTGATC | TGTGATCAGT | TTCG |  | 2854 |

( 2 ) INFORMATION FOR SEQ ID NO:58:

( i ) SEQUENCE CHARACTERISTICS:
        ( A ) LENGTH: 730 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

| Met | Arg | Ala | Ala | Leu | Val | Ala | Val | Ala | Ala | Leu | Leu | Trp | Val | Ala | Leu |
|---|---|---|---|---|---|---|---|---|---|---|---|---|---|---|---|
| 1 |  |  |  | 5 |  |  |  |  | 10 |  |  |  |  | 15 |  |

| His | Ala | Ala | Ala | Trp | Val | Asn | Asp | Val | Ser | Pro | Lys | Met | Tyr | Val | Gln |
|---|---|---|---|---|---|---|---|---|---|---|---|---|---|---|---|
|  |  |  | 20 |  |  |  |  | 25 |  |  |  |  | 30 |  |  |

| Phe | Gly | Glu | Glu | Arg | Val | Gln | Arg | Phe | Leu | Gly | Asn | Glu | Ser | His | Lys |
|---|---|---|---|---|---|---|---|---|---|---|---|---|---|---|---|
|  |  |  | 35 |  |  |  |  | 40 |  |  |  |  | 45 |  |  |

| Asp | His | Phe | Lys | Leu | Leu | Glu | Lys | Asp | His | Asn | Ser | Leu | Leu | Val | Gly |
|---|---|---|---|---|---|---|---|---|---|---|---|---|---|---|---|
|  | 50 |  |  |  |  | 55 |  |  |  |  | 60 |  |  |  |  |

```
Ala  Arg  Asn  Ile  Val  Tyr  Asn  Ile  Ser  Leu  Arg  Asp  Leu  Thr  Glu  Phe
 65                 70                     75                           80

Thr  Glu  Gln  Arg  Ile  Glu  Trp  His  Ser  Ser  Gly  Ala  His  Arg  Glu  Leu
                85                       90                           95

Cys  Tyr  Leu  Lys  Gly  Lys  Ser  Glu  Asp  Cys  Gln  Asn  Tyr  Ile  Arg
               100                     105                    110

Val  Leu  Ala  Lys  Ile  Asp  Asp  Arg  Val  Leu  Ile  Cys  Gly  Thr  Asn
          115                      120                    125

Ala  Tyr  Lys  Pro  Leu  Cys  Arg  His  Tyr  Ala  Leu  Lys  Asp  Gly  Asp  Tyr
     130                      135                    140

Val  Val  Glu  Lys  Glu  Tyr  Glu  Gly  Arg  Gly  Leu  Cys  Pro  Phe  Asp  Pro
145                      150                    155                      160

Asp  His  Asn  Ser  Thr  Ala  Ile  Tyr  Ser  Glu  Gly  Gln  Leu  Tyr  Ser  Ala
                165                      170                         175

Thr  Val  Ala  Asp  Phe  Ser  Gly  Thr  Asp  Pro  Leu  Ile  Tyr  Arg  Gly  Pro
               180                     185                         190

Leu  Arg  Thr  Glu  Arg  Ser  Asp  Leu  Lys  Gln  Leu  Asn  Ala  Pro  Asn  Phe
          195                      200                    205

Val  Asn  Thr  Met  Glu  Tyr  Asn  Asp  Phe  Ile  Phe  Phe  Phe  Phe  Arg  Glu
     210                     215                    220

Thr  Ala  Val  Glu  Tyr  Ile  Asn  Cys  Gly  Lys  Ala  Ile  Tyr  Ser  Arg  Val
225                      230                    235                      240

Ala  Arg  Val  Cys  Lys  His  Asp  Lys  Gly  Gly  Pro  His  Gln  Gly  Gly  Asp
               245                     250                         255

Arg  Trp  Thr  Ser  Phe  Leu  Lys  Ser  Arg  Leu  Asn  Cys  Ser  Val  Pro  Gly
               260                     265                         270

Asp  Tyr  Pro  Phe  Tyr  Phe  Asn  Glu  Ile  Gln  Ser  Thr  Ser  Asp  Ile  Ile
          275                      280                    285

Glu  Gly  Asn  Tyr  Gly  Gly  Gln  Val  Glu  Lys  Leu  Ile  Tyr  Gly  Val  Phe
     290                     295                    300

Thr  Thr  Pro  Val  Asn  Ser  Ile  Gly  Gly  Ser  Ala  Val  Cys  Ala  Phe  Ser
305                      310                    315                      320

Met  Lys  Ser  Ile  Leu  Glu  Ser  Phe  Asp  Gly  Pro  Phe  Lys  Glu  Gln  Glu
               325                     330                         335

Thr  Met  Asn  Ser  Asn  Trp  Leu  Ala  Val  Pro  Ser  Leu  Lys  Val  Pro  Glu
               340                     345                         350

Pro  Arg  Pro  Gly  Gln  Cys  Val  Asn  Asp  Ser  Arg  Thr  Leu  Pro  Asp  Val
          355                      360                    365

Ser  Val  Asn  Phe  Val  Lys  Ser  His  Thr  Leu  Met  Asp  Glu  Ala  Val  Pro
     370                     375                    380

Ala  Phe  Phe  Thr  Arg  Pro  Ile  Leu  Ile  Arg  Ile  Ser  Leu  Gln  Tyr  Arg
385                      390                    395                      400

Phe  Thr  Lys  Ile  Ala  Val  Asp  Gln  Gln  Val  Arg  Thr  Pro  Asp  Gly  Lys
               405                     410                         415

Ala  Tyr  Asp  Val  Leu  Phe  Ile  Gly  Thr  Asp  Asp  Gly  Lys  Val  Ile  Lys
               420                     425                         430

Ala  Leu  Asn  Ser  Ala  Ser  Phe  Asp  Ser  Ser  Asp  Thr  Val  Asp  Ser  Val
          435                      440                    445

Val  Ile  Glu  Glu  Leu  Gln  Val  Leu  Pro  Pro  Gly  Val  Pro  Val  Lys  Asn
     450                     455                    460

Leu  Tyr  Val  Val  Arg  Met  Asp  Gly  Asp  Asp  Ser  Lys  Leu  Val  Val  Val
465                      470                    475                      480

Ser  Asp  Asp  Glu  Ile  Leu  Ala  Ile  Lys  Leu  His  Arg  Cys  Gly  Ser  Asp
```

-continued

|   |   |   | 485 |   |   |   | 490 |   |   |   | 495 |   |   |
|---|---|---|---|---|---|---|---|---|---|---|---|---|---|
| Lys | Ile | Thr | Asn | Cys | Arg | Glu | Cys | Val | Ser | Leu | Gln | Asp | Pro | Tyr | Cys |
|  |  |  | 500 |  |  |  | 505 |  |  |  | 510 |  |  |

| Ala | Trp | Asp | Asn | Val | Glu | Leu | Lys | Cys | Thr | Ala | Val | Gly | Ser | Pro | Asp |
|  |  | 515 |  |  |  | 520 |  |  |  | 525 |  |  |  |  |  |

| Trp | Ser | Ala | Gly | Lys | Arg | Arg | Phe | Ile | Gln | Asn | Ile | Ser | Leu | Gly | Glu |
|  | 530 |  |  |  |  | 535 |  |  |  | 540 |  |  |  |  |  |

| His | Lys | Ala | Cys | Gly | Gly | Arg | Pro | Gln | Thr | Glu | Ile | Val | Ala | Ser | Pro |
| 545 |  |  |  |  | 550 |  |  |  | 555 |  |  |  |  | 560 |  |

| Val | Pro | Thr | Gln | Pro | Thr | Thr | Lys | Ser | Ser | Gly | Asp | Pro | Val | His | Ser |
|  |  |  |  | 565 |  |  |  |  | 570 |  |  |  |  | 575 |  |

| Ile | His | Gln | Ala | Glu | Phe | Glu | Pro | Glu | Ile | Asp | Asn | Glu | Ile | Val | Ile |
|  |  |  | 580 |  |  |  | 585 |  |  |  | 590 |  |  |  |  |

| Gly | Val | Asp | Asp | Ser | Asn | Val | Ile | Pro | Asn | Thr | Leu | Ala | Glu | Ile | Asn |
|  |  | 595 |  |  |  |  | 600 |  |  |  | 605 |  |  |  |  |

| His | Ala | Gly | Ser | Lys | Leu | Pro | Ser | Ser | Gln | Glu | Lys | Leu | Pro | Ile | Tyr |
|  | 610 |  |  |  |  | 615 |  |  |  | 620 |  |  |  |  |  |

| Thr | Ala | Glu | Thr | Leu | Thr | Ile | Ala | Ile | Val | Thr | Ser | Cys | Leu | Gly | Ala |
| 625 |  |  |  |  | 630 |  |  |  | 635 |  |  |  |  | 640 |  |

| Leu | Val | Val | Gly | Phe | Ile | Ser | Gly | Phe | Leu | Phe | Ser | Arg | Arg | Cys | Arg |
|  |  |  |  | 645 |  |  |  | 650 |  |  |  | 655 |  |  |  |

| Gly | Glu | Asp | Tyr | Thr | Asp | Met | Pro | Phe | Pro | Asp | Gln | Arg | His | Gln | Leu |
|  |  |  | 660 |  |  |  | 665 |  |  |  | 670 |  |  |  |

| Asn | Arg | Leu | Thr | Glu | Ala | Gly | Leu | Asn | Ala | Asp | Ser | Pro | Tyr | Leu | Pro |
|  |  | 675 |  |  |  | 680 |  |  |  | 685 |  |  |  |  |

| Pro | Cys | Ala | Asn | Asn | Lys | Ala | Ala | Ile | Asn | Leu | Val | Leu | Asn | Val | Pro |
|  | 690 |  |  |  | 695 |  |  |  | 700 |  |  |  |  |  |

| Pro | Lys | Asn | Ala | Asn | Gly | Lys | Asn | Ala | Asn | Ser | Ser | Ala | Glu | Asn | Lys |
| 705 |  |  |  | 710 |  |  |  | 715 |  |  |  |  | 720 |  |

| Pro | Ile | Gln | Lys | Val | Lys | Lys | Thr | Tyr | Ile |
|  |  |  |  | 725 |  |  |  |  | 730 |

( 2 ) INFORMATION FOR SEQ ID NO:59:

( i ) SEQUENCE CHARACTERISTICS:
        ( A ) LENGTH: 3560 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..1953

( x i ) SEQUENCE DESCRIPTION: SEQ ID NO:59:

| GAG | GAT | GAT | TGT | CAG | AAT | TAC | ATC | CGC | ATC | ATG | GTG | GTG | CCA | TCG | CCG | 48 |
| Glu | Asp | Asp | Cys | Gln | Asn | Tyr | Ile | Arg | Ile | Met | Val | Val | Pro | Ser | Pro |  |
| 1 |  |  |  | 5 |  |  |  |  | 10 |  |  |  |  | 15 |  |  |

| GGT | CGC | CTT | TTC | GTT | TGT | GGC | ACC | AAC | TCG | TTC | CGG | CCC | ATG | TGC | AAC | 96 |
| Gly | Arg | Leu | Phe | Val | Cys | Gly | Thr | Asn | Ser | Phe | Arg | Pro | Met | Cys | Asn |  |
|  |  |  | 20 |  |  |  |  | 25 |  |  |  |  | 30 |  |  |  |

| ACG | TAT | ATC | ATT | AGT | GAC | AGC | AAC | TAC | ACG | CTG | GAG | GCC | ACG | AAG | AAC | 144 |
| Thr | Tyr | Ile | Ile | Ser | Asp | Ser | Asn | Tyr | Thr | Leu | Glu | Ala | Thr | Lys | Asn |  |
|  |  | 35 |  |  |  |  | 40 |  |  |  |  | 45 |  |  |  |  |

| GGA | CAG | GCG | GTG | TGC | CCC | TAC | GAT | CCA | CGT | CAC | AAC | TCC | ACC | TCT | GTG | 192 |
| Gly | Gln | Ala | Val | Cys | Pro | Tyr | Asp | Pro | Arg | His | Asn | Ser | Thr | Ser | Val |  |
|  | 50 |  |  |  |  | 55 |  |  |  |  | 60 |  |  |  |  |  |

| | | | | | | | | | | | | | | | | |
|---|---|---|---|---|---|---|---|---|---|---|---|---|---|---|---|---|
| CTG | GCC | GAC | AAC | GAA | CTG | TAT | TCC | GGT | ACC | GTG | GCG | GAT | TTC | AGT | GGC | 240 |
| Leu | Ala | Asp | Asn | Glu | Leu | Tyr | Ser | Gly | Thr | Val | Ala | Asp | Phe | Ser | Gly | |
| 65 | | | | 70 | | | | | 75 | | | | | | 80 | |
| AGC | GAT | CCG | ATT | ATC | TAC | CGG | GAG | CCC | CTG | CAG | ACC | GAG | CAG | TAC | GAT | 288 |
| Ser | Asp | Pro | Ile | Ile | Tyr | Arg | Glu | Pro | Leu | Gln | Thr | Glu | Gln | Tyr | Asp | |
| | | | | 85 | | | | | 90 | | | | | 95 | | |
| AGC | CTA | AGT | CTC | AAC | GCA | CCG | AAC | TTT | GTG | AGC | TCA | TTT | ACG | CAG | GGC | 336 |
| Ser | Leu | Ser | Leu | Asn | Ala | Pro | Asn | Phe | Val | Ser | Ser | Phe | Thr | Gln | Gly | |
| | | | 100 | | | | | 105 | | | | | 110 | | | |
| GAC | TTT | GTC | TAT | TTC | TTC | TTT | CGG | GAA | ACC | GCC | GTT | GAG | TTT | ATC | AAC | 384 |
| Asp | Phe | Val | Tyr | Phe | Phe | Phe | Arg | Glu | Thr | Ala | Val | Glu | Phe | Ile | Asn | |
| | | 115 | | | | | 120 | | | | | 125 | | | | |
| TGT | GGC | AAG | GCG | ATT | TAT | TCG | CGC | GTT | GCC | CGC | GTC | TGC | AAA | TGG | GAC | 432 |
| Cys | Gly | Lys | Ala | Ile | Tyr | Ser | Arg | Val | Ala | Arg | Val | Cys | Lys | Trp | Asp | |
| | 130 | | | | | 135 | | | | | 140 | | | | | |
| AAA | GGT | GGC | CCG | CAT | CGA | TTC | CGC | AAC | CGC | TGG | ACA | TCC | TTC | CTC | AAG | 480 |
| Lys | Gly | Gly | Pro | His | Arg | Phe | Arg | Asn | Arg | Trp | Thr | Ser | Phe | Leu | Lys | |
| 145 | | | | | 150 | | | | | 155 | | | | | 160 | |
| TCC | CGC | CTC | AAC | TGC | TCC | ATT | CCC | GGC | GAT | TAT | CCT | TTC | TAC | TTT | AAT | 528 |
| Ser | Arg | Leu | Asn | Cys | Ser | Ile | Pro | Gly | Asp | Tyr | Pro | Phe | Tyr | Phe | Asn | |
| | | | | 165 | | | | | 170 | | | | | 175 | | |
| GAA | ATC | CAA | TCT | GCC | AGC | AAT | CTG | GTG | GAG | GGA | CAG | TAT | GGC | TCG | ATG | 576 |
| Glu | Ile | Gln | Ser | Ala | Ser | Asn | Leu | Val | Glu | Gly | Gln | Tyr | Gly | Ser | Met | |
| | | | 180 | | | | | 185 | | | | | 190 | | | |
| AGC | TCG | AAA | CTG | ATC | TAC | GGA | GTC | TTC | AAC | ACG | CCG | AGC | AAC | TCA | ATT | 624 |
| Ser | Ser | Lys | Leu | Ile | Tyr | Gly | Val | Phe | Asn | Thr | Pro | Ser | Asn | Ser | Ile | |
| | | 195 | | | | | 200 | | | | | 205 | | | | |
| CCC | GGC | TCA | GCG | GTT | TGT | GCC | TTT | GCC | CTC | CAG | GAC | ATT | GCC | GAT | ACG | 672 |
| Pro | Gly | Ser | Ala | Val | Cys | Ala | Phe | Ala | Leu | Gln | Asp | Ile | Ala | Asp | Thr | |
| | 210 | | | | | 215 | | | | | 220 | | | | | |
| TTT | GAG | GGT | CAG | TTC | AAG | GAG | CAG | ACT | GGC | ATC | AAC | TCC | AAC | TGG | CTG | 720 |
| Phe | Glu | Gly | Gln | Phe | Lys | Glu | Gln | Thr | Gly | Ile | Asn | Ser | Asn | Trp | Leu | |
| 225 | | | | | 230 | | | | | 235 | | | | | 240 | |
| CCA | GTG | AAC | AAC | GCC | AAG | GTA | CCC | GAT | CCT | CGA | CCC | GGT | TCC | TGT | CAC | 768 |
| Pro | Val | Asn | Asn | Ala | Lys | Val | Pro | Asp | Pro | Arg | Pro | Gly | Ser | Cys | His | |
| | | | | 245 | | | | | 250 | | | | | 255 | | |
| AAC | GAT | TCG | AGA | GCG | CTT | CCG | GAT | CCC | ACA | CTG | AAC | TTC | ATC | AAA | ACA | 816 |
| Asn | Asp | Ser | Arg | Ala | Leu | Pro | Asp | Pro | Thr | Leu | Asn | Phe | Ile | Lys | Thr | |
| | | | 260 | | | | | 265 | | | | | 270 | | | |
| CAT | TCG | CTA | ATG | GAC | GAG | AAT | GTG | CCG | GCA | TTT | TTC | AGT | CAA | CCG | ATT | 864 |
| His | Ser | Leu | Met | Asp | Glu | Asn | Val | Pro | Ala | Phe | Phe | Ser | Gln | Pro | Ile | |
| | | 275 | | | | | 280 | | | | | 285 | | | | |
| TTG | GTC | CGG | ACG | AGC | ACA | ATA | TAC | CGC | TTC | ACT | CAA | ATC | GCC | GTA | GAT | 912 |
| Leu | Val | Arg | Thr | Ser | Thr | Ile | Tyr | Arg | Phe | Thr | Gln | Ile | Ala | Val | Asp | |
| | | 290 | | | | | 295 | | | | | 300 | | | | |
| GCG | CAG | ATT | AAA | ACT | CCT | GGC | GGC | AAG | ACA | TAT | GAT | GTT | ATC | TTT | GTG | 960 |
| Ala | Gln | Ile | Lys | Thr | Pro | Gly | Gly | Lys | Thr | Tyr | Asp | Val | Ile | Phe | Val | |
| 305 | | | | | 310 | | | | | 315 | | | | | 320 | |
| GGC | ACA | GAT | CAT | GGA | AAG | ATT | ATT | AAG | TCA | GTG | AAT | GCT | GAA | TCT | GCC | 1008 |
| Gly | Thr | Asp | His | Gly | Lys | Ile | Ile | Lys | Ser | Val | Asn | Ala | Glu | Ser | Ala | |
| | | | | 325 | | | | | 330 | | | | | 335 | | |
| GAT | TCA | GCG | GAT | AAA | GTC | ACC | TCC | GTA | GTC | ATC | GAG | GAG | ATC | GAT | GTC | 1056 |
| Asp | Ser | Ala | Asp | Lys | Val | Thr | Ser | Val | Val | Ile | Glu | Glu | Ile | Asp | Val | |
| | | | 340 | | | | | 345 | | | | | 350 | | | |
| CTG | ACC | AAG | AGT | GAA | CCC | ATA | CGC | AAT | CTG | GAG | ATA | GTC | AGA | ACC | ATG | 1104 |
| Leu | Thr | Lys | Ser | Glu | Pro | Ile | Arg | Asn | Leu | Glu | Ile | Val | Arg | Thr | Met | |
| | | 355 | | | | | 360 | | | | | 365 | | | | |
| CAG | TAC | GAT | CAA | CCC | AAA | GAT | GGC | AGC | TAC | GAC | GAT | GGT | AAA | TTA | ATC | 1152 |
| Gln | Tyr | Asp | Gln | Pro | Lys | Asp | Gly | Ser | Tyr | Asp | Asp | Gly | Lys | Leu | Ile | |
| | | 370 | | | | | 375 | | | | | 380 | | | | |

| | | | | | | | | | | | | | | | | |
|---|---|---|---|---|---|---|---|---|---|---|---|---|---|---|---|---|
| ATT | GTG | ACG | GAC | AGT | CAG | GTG | GTA | GCC | ATA | CAA | TTG | CAT | CGT | TGT | CAC | 1200 |
| Ile | Val | Thr | Asp | Ser | Gln | Val | Val | Ala | Ile | Gln | Leu | His | Arg | Cys | His | |
| 385 | | | | 390 | | | | | 395 | | | | | | 400 | |
| AAT | GAC | AAA | ATC | ACC | AGC | TGC | AGC | GAG | TGC | GTC | GCA | TTG | CAG | GAT | CCG | 1248 |
| Asn | Asp | Lys | Ile | Thr | Ser | Cys | Ser | Glu | Cys | Val | Ala | Leu | Gln | Asp | Pro | |
| | | | | 405 | | | | | 410 | | | | | 415 | | |
| TAC | TGC | GCC | TGG | GAC | AAA | ATC | GCT | GGC | AAG | TGC | CGT | TCC | CAC | GGC | GCT | 1296 |
| Tyr | Cys | Ala | Trp | Asp | Lys | Ile | Ala | Gly | Lys | Cys | Arg | Ser | His | Gly | Ala | |
| | | | 420 | | | | | 425 | | | | | 430 | | | |
| CCC | CGA | TGG | CTA | GAG | GAG | AAC | TAT | TTC | TAC | CAG | AAT | GTG | GCC | ACT | GGC | 1344 |
| Pro | Arg | Trp | Leu | Glu | Glu | Asn | Tyr | Phe | Tyr | Gln | Asn | Val | Ala | Thr | Gly | |
| | | 435 | | | | | 440 | | | | | 445 | | | | |
| CAG | CAT | GCG | GCC | TGC | CCC | TCA | GGC | AAA | ATC | AAT | TCA | AAG | GAT | GCC | AAC | 1392 |
| Gln | His | Ala | Ala | Cys | Pro | Ser | Gly | Lys | Ile | Asn | Ser | Lys | Asp | Ala | Asn | |
| | 450 | | | | | 455 | | | | | 460 | | | | | |
| GCT | GGG | GAG | CAG | AAG | GGC | TTC | CGC | AAC | GAC | ATG | GAC | TTA | TTG | GAT | TCG | 1440 |
| Ala | Gly | Glu | Gln | Lys | Gly | Phe | Arg | Asn | Asp | Met | Asp | Leu | Leu | Asp | Ser | |
| 465 | | | | | 470 | | | | | 475 | | | | | 480 | |
| CGA | CGC | CAG | AGC | AAG | GAT | CAG | GAA | ATA | ATC | GAC | AAT | ATT | GAT | AAG | AAC | 1488 |
| Arg | Arg | Gln | Ser | Lys | Asp | Gln | Glu | Ile | Ile | Asp | Asn | Ile | Asp | Lys | Asn | |
| | | | | 485 | | | | | 490 | | | | | 495 | | |
| TTT | GAA | GAT | ATA | ATC | AAC | GCC | CAG | TAC | ACT | GTG | GAG | ACC | CTC | GTG | ATG | 1536 |
| Phe | Glu | Asp | Ile | Ile | Asn | Ala | Gln | Tyr | Thr | Val | Glu | Thr | Leu | Val | Met | |
| | | | 500 | | | | | 505 | | | | | 510 | | | |
| GCC | GTT | CTG | GCC | GGT | TCG | ATC | TTT | TCG | CTG | CTG | GTC | GGC | TTC | TTT | ACA | 1584 |
| Ala | Val | Leu | Ala | Gly | Ser | Ile | Phe | Ser | Leu | Leu | Val | Gly | Phe | Phe | Thr | |
| | | 515 | | | | | 520 | | | | | 525 | | | | |
| GGC | TAC | TTC | TGC | GGT | CGC | CGT | TGT | CAC | AAG | GAC | GAG | GAT | GAT | AAT | CTG | 1632 |
| Gly | Tyr | Phe | Cys | Gly | Arg | Arg | Cys | His | Lys | Asp | Glu | Asp | Asp | Asn | Leu | |
| | 530 | | | | | 535 | | | | | 540 | | | | | |
| CCG | TAT | CCG | GAT | ACG | GAG | TAC | GAG | TAC | TTC | GAG | CAG | CGA | CAG | AAT | GTC | 1680 |
| Pro | Tyr | Pro | Asp | Thr | Glu | Tyr | Glu | Tyr | Phe | Glu | Gln | Arg | Gln | Asn | Val | |
| 545 | | | | | 550 | | | | | 555 | | | | | 560 | |
| AAT | AGC | TTC | CCC | TCG | TCC | TGT | CGC | ATC | CAG | CAG | GAG | CCC | AAG | CTG | CTG | 1728 |
| Asn | Ser | Phe | Pro | Ser | Ser | Cys | Arg | Ile | Gln | Gln | Glu | Pro | Lys | Leu | Leu | |
| | | | | 565 | | | | | 570 | | | | | 575 | | |
| CCC | CAA | GTG | GAG | GAG | GTG | ACG | TAT | GCG | GAC | GCA | GTG | CTC | CTG | CCA | CAG | 1776 |
| Pro | Gln | Val | Glu | Glu | Val | Thr | Tyr | Ala | Asp | Ala | Val | Leu | Leu | Pro | Gln | |
| | | | 580 | | | | | 585 | | | | | 590 | | | |
| CCT | CCG | CCG | CCC | AAT | AAG | ATG | CAC | TCG | CCG | AAG | AAC | ACG | CTG | CGT | AAG | 1824 |
| Pro | Pro | Pro | Pro | Asn | Lys | Met | His | Ser | Pro | Lys | Asn | Thr | Leu | Arg | Lys | |
| | | 595 | | | | | 600 | | | | | 605 | | | | |
| CCC | CCG | ATG | CAC | CAG | ATG | CAC | CAG | GGT | CCC | AAC | TCG | GAG | ACC | CTC | TTC | 1872 |
| Pro | Pro | Met | His | Gln | Met | His | Gln | Gly | Pro | Asn | Ser | Glu | Thr | Leu | Phe | |
| | 610 | | | | | 615 | | | | | 620 | | | | | |
| CAG | TTC | CAC | GTG | ACG | GCT | ACA | ACA | CCC | AGC | AGT | CGT | ATC | GTG | GTC | GCG | 1920 |
| Gln | Phe | His | Val | Thr | Ala | Thr | Thr | Pro | Ser | Ser | Arg | Ile | Val | Val | Ala | |
| 625 | | | | | 630 | | | | | 635 | | | | | 640 | |
| ACA | ACT | TCG | GAA | CAC | TGC | GTT | CCC | ACC | AGG | TGATGGGCGA | | CAATTACAGG | | | | 1970 |
| Thr | Thr | Ser | Glu | His | Cys | Val | Pro | Thr | Arg | | | | | | | |
| | | | | 645 | | | | | 650 | | | | | | | |

| | | | | | |
|---|---|---|---|---|---|
| CGCGGCGATG | GCTTTTCCAC | CACCCGCAGC | GTCAAGAAGG | TTTACCTTTG | AGACGGGAGT | 2030 |
| GGGCGGCTG | AAACCAGTCA | GGACTAATT | ACCCAAAATA | TGGCTGTAAA | CAACACAAAC | 2090 |
| ACACGTAACA | GAAGTCTTGG | TCGCGCAAGA | AGACAGCCGC | CCCGTCATGG | CATTGTAACT | 2150 |
| CAACACCGCT | CGAATAGCCC | CCAGCAGCAG | CAGCAGCAGT | CGCAGCAGCC | GCACTCCAGT | 2210 |
| TCGGGCTCCT | CGCCCGTAAT | GTCCAACAGC | AGCAGCAGTC | CGGCTCCGCC | CTCCAGCAGT | 2270 |
| CCCAGTCCGC | AGGAGAGCCC | CAAGAACTGC | AGCTACATCT | ACCGTGATTG | ATTGATATGC | 2330 |

-continued

| | | | | | |
|---|---|---|---|---|---|
| AACACCAAAT | CGATGCCACT | CATCCAGGCC | CAGTCCACGC | ACGCCCAGCC | ACACTCACAC | 2390 |
| CCGCACCCGC | ACCCGCTTCC | GCCACCCGGT | CCGACCACGC | CCCCAGCACA | GCCACGCGCC | 2450 |
| AGAAGTCCAA | TGATCGGCAG | GACATATGCC | AAGTCCATGC | CCGTGACACC | AGTTCAACCG | 2510 |
| CAATCGCCGC | TGGCTGAGAC | GCCCTCCTAT | GAGCTCTACG | AACGCCACTC | GGATGCGGCC | 2570 |
| ACCTTCCACT | TTGGGGATGA | GGACGATGAC | GATGATGATG | AGCACGACCA | GGAGGACACC | 2630 |
| TCATCGCTGG | CCATGATCAC | ACCGCCGCCG | CCCTACGACA | CTCCGCATCT | GATTGCATCG | 2690 |
| CCACCGCTGC | CGCCGCCTCG | TAGATTTCGC | TTTGGCAACA | GGGAGCTGTT | CAGCATGAGT | 2750 |
| CCAGCCGGAG | GTGGAACCAC | GCCCACCGCC | TCGGCAGGCC | AACGCGGCAG | CAGCGCCATC | 2810 |
| ACGCCCACAA | AGTTGAGTGC | GGCGGCAGCG | GCCATGTTTG | CCGCACCCCA | AATGGCCACC | 2870 |
| CAACTCAACC | GGAAGTGGGC | TCATTTGCAA | AGGAAGCGGC | GCAGGCGCAA | CAGCAGCTCC | 2930 |
| GGCGATTCTA | AGGAGCTCGA | CAAACTGGTC | CTGCAATCGG | TCGACTGGGA | TGAGAATGAG | 2990 |
| ATGTACTAGA | ACGCAAACCA | ACAATGAGAT | AGCAGAAACA | CTTTGATTCG | GAATTTATAC | 3050 |
| ACCTTTGCAT | ATTTTGAATA | TGACTTCAAT | TTTAAAATGC | GTAATTATGT | TCTTATTTTT | 3110 |
| TAAAGAACGC | TTTAGAGAAG | TTTTCTGCTA | CCTTAAATAG | TACACACAAC | TCATATCTAA | 3170 |
| CGTGGCGCTG | CGATATAGGA | ATAACCACTC | CCCCTTCCCT | TAAACTTAAA | GTAGCAATCG | 3230 |
| AAAAGATCAT | TCATTAGCGA | CAGAAACTGG | ATGGGGATTT | ACTTACACAC | AAAAAGCCAG | 3290 |
| AGAAGTTATA | CACGAAGTTT | ATAGTTATAT | AGCCTTTATA | CATACTCCCC | GATCTGCTAA | 3350 |
| GTATACACAA | GCAAGCATAA | CATAACATAC | GTATATATGA | CTCTATATAT | ACCAATAGAT | 3410 |
| TTCATAGACG | ATTCACATGG | ATCGGCTACG | CTAAATTAGA | GCTGCAAAAT | GATATTGTTA | 3470 |
| ATTACGATTA | GAGAAAAAAA | AAAAGGAATT | CGATATCAAG | CKTATCGATA | CCNTCGACCT | 3530 |
| CGNNNNNGGG | GCCCGGTACC | CAATTCGCCC | | | | 3560 |

( 2 ) INFORMATION FOR SEQ ID NO:60:

( i ) SEQUENCE CHARACTERISTICS:
        ( A ) LENGTH: 650 amino acids
        ( B ) TYPE: amino acid
        ( D ) TOPOLOGY: linear ( i i ) MOLECULE TYPE: protein ( x i ) SEQUENCE DESCRIPTION: SEQ ID NO:60:

| | | | | | | | | | | | | | | |
|---|---|---|---|---|---|---|---|---|---|---|---|---|---|---|
| Glu | Asp | Asp | Cys | Gln | Asn | Tyr | Ile | Arg | Ile | Met | Val | Val | Pro | Ser | Pro |
| 1 | | | | 5 | | | | | 10 | | | | | 15 | |
| Gly | Arg | Leu | Phe | Val | Cys | Gly | Thr | Asn | Ser | Phe | Arg | Pro | Met | Cys | Asn |
| | | | 20 | | | | | 25 | | | | 30 | | | |
| Thr | Tyr | Ile | Ile | Ser | Asp | Ser | Asn | Tyr | Thr | Leu | Glu | Ala | Thr | Lys | Asn |
| | | 35 | | | | | 40 | | | | | 45 | | | |
| Gly | Gln | Ala | Val | Cys | Pro | Tyr | Asp | Pro | Arg | His | Asn | Ser | Thr | Ser | Val |
| | 50 | | | | | 55 | | | | | 60 | | | | |
| Leu | Ala | Asp | Asn | Glu | Leu | Tyr | Ser | Gly | Thr | Val | Ala | Asp | Phe | Ser | Gly |
| 65 | | | | | 70 | | | | | 75 | | | | | 80 |
| Ser | Asp | Pro | Ile | Ile | Tyr | Arg | Glu | Pro | Leu | Gln | Thr | Glu | Gln | Tyr | Asp |
| | | | | 85 | | | | | 90 | | | | | 95 | |
| Ser | Leu | Ser | Leu | Asn | Ala | Pro | Asn | Phe | Val | Ser | Ser | Phe | Thr | Gln | Gly |
| | | | | 100 | | | | | 105 | | | | | 110 | |
| Asp | Phe | Val | Tyr | Phe | Phe | Phe | Arg | Glu | Thr | Ala | Val | Glu | Phe | Ile | Asn |
| | | | 115 | | | | | 120 | | | | 125 | | | |
| Cys | Gly | Lys | Ala | Ile | Tyr | Ser | Arg | Val | Ala | Arg | Val | Cys | Lys | Trp | Asp |
| | | 130 | | | | | 135 | | | | 140 | | | | |

```
Lys  Gly  Gly  Pro  His  Arg  Phe  Arg  Asn  Arg  Trp  Thr  Ser  Phe  Leu  Lys
145                      150                      155                      160

Ser  Arg  Leu  Asn  Cys  Ser  Ile  Pro  Gly  Asp  Tyr  Pro  Phe  Tyr  Phe  Asn
                    165                      170                      175

Glu  Ile  Gln  Ser  Ala  Ser  Asn  Leu  Val  Glu  Gly  Gln  Tyr  Gly  Ser  Met
               180                      185                      190

Ser  Ser  Lys  Leu  Ile  Tyr  Gly  Val  Phe  Asn  Thr  Pro  Ser  Asn  Ser  Ile
          195                      200                      205

Pro  Gly  Ser  Ala  Val  Cys  Ala  Phe  Ala  Leu  Gln  Asp  Ile  Ala  Asp  Thr
     210                      215                      220

Phe  Glu  Gly  Gln  Phe  Lys  Glu  Gln  Thr  Gly  Ile  Asn  Ser  Asn  Trp  Leu
225                      230                      235                      240

Pro  Val  Asn  Asn  Ala  Lys  Val  Pro  Asp  Pro  Arg  Pro  Gly  Ser  Cys  His
                    245                      250                      255

Asn  Asp  Ser  Arg  Ala  Leu  Pro  Asp  Pro  Thr  Leu  Asn  Phe  Ile  Lys  Thr
               260                      265                      270

His  Ser  Leu  Met  Asp  Glu  Asn  Val  Pro  Ala  Phe  Phe  Ser  Gln  Pro  Ile
          275                      280                      285

Leu  Val  Arg  Thr  Ser  Thr  Ile  Tyr  Arg  Phe  Thr  Gln  Ile  Ala  Val  Asp
     290                      295                      300

Ala  Gln  Ile  Lys  Thr  Pro  Gly  Gly  Lys  Thr  Tyr  Asp  Val  Ile  Phe  Val
305                      310                      315                      320

Gly  Thr  Asp  His  Gly  Lys  Ile  Ile  Lys  Ser  Val  Asn  Ala  Glu  Ser  Ala
                    325                      330                      335

Asp  Ser  Ala  Asp  Lys  Val  Thr  Ser  Val  Ile  Glu  Glu  Ile  Asp  Val
               340                      345                      350

Leu  Thr  Lys  Ser  Glu  Pro  Ile  Arg  Asn  Leu  Glu  Ile  Val  Arg  Thr  Met
          355                      360                      365

Gln  Tyr  Asp  Gln  Pro  Lys  Asp  Gly  Ser  Tyr  Asp  Asp  Gly  Lys  Leu  Ile
     370                      375                      380

Ile  Val  Thr  Asp  Ser  Gln  Val  Val  Ala  Ile  Gln  Leu  His  Arg  Cys  His
385                      390                      395                      400

Asn  Asp  Lys  Ile  Thr  Ser  Cys  Ser  Glu  Cys  Val  Ala  Leu  Gln  Asp  Pro
                    405                      410                      415

Tyr  Cys  Ala  Trp  Asp  Lys  Ile  Ala  Gly  Lys  Cys  Arg  Ser  His  Gly  Ala
               420                      425                      430

Pro  Arg  Trp  Leu  Glu  Glu  Asn  Tyr  Phe  Tyr  Gln  Asn  Val  Ala  Thr  Gly
          435                      440                      445

Gln  His  Ala  Ala  Cys  Pro  Ser  Gly  Lys  Ile  Asn  Ser  Lys  Asp  Ala  Asn
     450                      455                      460

Ala  Gly  Glu  Gln  Lys  Gly  Phe  Arg  Asn  Asp  Met  Asp  Leu  Leu  Asp  Ser
465                      470                      475                      480

Arg  Arg  Gln  Ser  Lys  Asp  Gln  Glu  Ile  Ile  Asp  Asn  Ile  Asp  Lys  Asn
                    485                      490                      495

Phe  Glu  Asp  Ile  Ile  Asn  Ala  Gln  Tyr  Thr  Val  Glu  Thr  Leu  Val  Met
               500                      505                      510

Ala  Val  Leu  Ala  Gly  Ser  Ile  Phe  Ser  Leu  Leu  Val  Gly  Phe  Phe  Thr
          515                      520                      525

Gly  Tyr  Phe  Cys  Gly  Arg  Arg  Cys  His  Lys  Asp  Glu  Asp  Asp  Asn  Leu
     530                      535                      540

Pro  Tyr  Pro  Asp  Thr  Glu  Tyr  Glu  Tyr  Phe  Glu  Gln  Arg  Gln  Asn  Val
545                      550                      555                      560

Asn  Ser  Phe  Pro  Ser  Ser  Cys  Arg  Ile  Gln  Gln  Glu  Pro  Lys  Leu  Leu
```

|                |                |                |                | 5 6 5          |                |                |                | 5 7 0          |                |                |                | 5 7 5          |                |                |
| -------------- | -------------- | -------------- | -------------- | -------------- | -------------- | -------------- | -------------- | -------------- | -------------- | -------------- | -------------- | -------------- | -------------- | -------------- |
| Pro            | Gln            | Val            | Glu<br>580     | Glu            | Val            | Thr            | Tyr            | Ala<br>585     | Asp            | Ala            | Val            | Leu<br>590     | Leu            | Pro            | Gln            |
| Pro            | Pro            | Pro<br>595     | Pro            | Asn            | Lys            | Met            | His<br>600     | Ser            | Pro            | Lys            | Asn            | Thr<br>605     | Leu            | Arg            | Lys            |
| Pro            | Pro<br>610     | Met            | His            | Gln            | Met            | His<br>615     | Gln            | Gly            | Pro            | Asn            | Ser<br>620     | Glu            | Thr            | Leu            | Phe            |
| Gln<br>625     | Phe            | His            | Val            | Thr            | Ala<br>630     | Thr            | Thr            | Pro            | Ser            | Ser<br>635     | Arg            | Ile            | Val            | Val            | Ala<br>640     |
| Thr            | Thr            | Ser            | Glu            | His<br>645     | Cys            | Val            | Pro            | Thr            | Arg<br>650     |                |                |                |                |                |

( 2 ) INFORMATION FOR SEQ ID NO:61:

( i ) SEQUENCE CHARACTERISTICS:
  ( A ) LENGTH: 2670 base pairs
  ( B ) TYPE: nucleic acid
  ( C ) STRANDEDNESS: double
  ( D ) TOPOLOGY: linear ( i i ) MOLECULE TYPE: cDNA ( i x ) FEATURE:
  ( A ) NAME/KEY: CDS
  ( B ) LOCATION: 268..2439

( x i ) SEQUENCE DESCRIPTION: SEQ ID NO:61:

```
GAAAATCGAA  CWCCGAATTG  AATGAACWGC  AAAACGCCAA  TTAGATAGTT  GCAAGCCTAA      60

TGCATTTCAG  AKATTTNMMC  GATGCGAAAC  AAGTTCCGCC  ACGAAAGTGA  ACAGTGGTAA     120

AATGCCCAAG  AATCTCGAGC  GGAAACACCA  AACACAAAAG  AACAAGCAAC  CGCCTCTCAC     180

TCGCTCTTGC  ACTTTAATCC  AATTGAGGTT  GGTGGGGTCG  CATTCGCCCC  CCGGTCGACC     240

ACCCCTCTCG  CTCGCACCGC  CCTCGCA ATG TCT CTT CTA CAG CTA TCG CCG CTC        294
                                Met Ser Leu Leu Gln Leu Ser Pro Leu
                                  1               5
```

| CTC | GCA | CTC | CTG | CTA | CTC | CTC | TGC | AGT | AGT | GTG | AGC | GAG | ACG | GCT | GCG | 342 |
| --- | --- | --- | --- | --- | --- | --- | --- | --- | --- | --- | --- | --- | --- | --- | --- | --- |
| Leu | Ala | Leu | Leu | Leu | Leu | Leu | Cys | Ser | Ser | Val | Ser | Glu | Thr | Ala | Ala |     |
| 10  |     |     |     |     | 15  |     |     |     |     | 20  |     |     |     |     | 25  |     |

| GAC | TAC | GAG | AAC | ACC | TGG | AAC | TTC | TAC | TAC | GAG | CGT | CCC | TGT | TGC | ACT | 390 |
| --- | --- | --- | --- | --- | --- | --- | --- | --- | --- | --- | --- | --- | --- | --- | --- | --- |
| Asp | Tyr | Glu | Asn | Thr | Trp | Asn | Phe | Tyr | Tyr | Glu | Arg | Pro | Cys | Cys | Thr |     |
|     |     |     |     | 30  |     |     |     |     | 35  |     |     |     |     | 40  |     |     |

| GGA | AAC | GAT | CAG | GGG | AAC | AAC | AAT | TAC | GGA | AAA | CAC | GGC | GCA | GAT | CAT | 438 |
| --- | --- | --- | --- | --- | --- | --- | --- | --- | --- | --- | --- | --- | --- | --- | --- | --- |
| Gly | Asn | Asp | Gln | Gly | Asn | Asn | Asn | Tyr | Gly | Lys | His | Gly | Ala | Asp | His |     |
|     |     |     | 45  |     |     |     |     | 50  |     |     |     |     | 55  |     |     |     |

| GTG | CGG | GAG | TTC | AAC | TGC | GGC | AAG | CTG | TAC | TAT | CGT | ACA | TTC | CAT | ATG | 486 |
| --- | --- | --- | --- | --- | --- | --- | --- | --- | --- | --- | --- | --- | --- | --- | --- | --- |
| Val | Arg | Glu | Phe | Asn | Cys | Gly | Lys | Leu | Tyr | Tyr | Arg | Thr | Phe | His | Met |     |
|     |     | 60  |     |     |     |     | 65  |     |     |     |     | 70  |     |     |     |     |

| AAC | GAA | GAT | CGA | GAT | ACG | CTC | TAT | GTG | GGA | GCC | ATG | GAT | CGC | GTA | TTC | 534 |
| --- | --- | --- | --- | --- | --- | --- | --- | --- | --- | --- | --- | --- | --- | --- | --- | --- |
| Asn | Glu | Asp | Arg | Asp | Thr | Leu | Tyr | Val | Gly | Ala | Met | Asp | Arg | Val | Phe |     |
|     |     | 75  |     |     |     |     | 80  |     |     |     |     | 85  |     |     |     |     |

| CGT | GTG | AAC | CTG | CAG | AAT | ATC | TCC | TCA | TCC | AAT | TGT | AAT | CGG | GAT | GCG | 582 |
| --- | --- | --- | --- | --- | --- | --- | --- | --- | --- | --- | --- | --- | --- | --- | --- | --- |
| Arg | Val | Asn | Leu | Gln | Asn | Ile | Ser | Ser | Ser | Asn | Cys | Asn | Arg | Asp | Ala |     |
| 90  |     |     |     |     | 95  |     |     |     |     | 100 |     |     |     |     | 105 |     |

| ATC | AAC | TTG | GAG | CCA | ACA | CGG | GAT | GAT | GTG | GTT | AGC | TGC | GTC | TCC | AAA | 630 |
| --- | --- | --- | --- | --- | --- | --- | --- | --- | --- | --- | --- | --- | --- | --- | --- | --- |
| Ile | Asn | Leu | Glu | Pro | Thr | Arg | Asp | Asp | Val | Val | Ser | Cys | Val | Ser | Lys |     |
|     |     |     |     | 110 |     |     |     |     | 115 |     |     |     |     | 120 |     |     |

| GGC | AAA | AGT | CAG | ATC | TTC | GAC | TGC | AAG | AAC | CAT | GTG | CGT | GTC | ATC | CAG | 678 |
| --- | --- | --- | --- | --- | --- | --- | --- | --- | --- | --- | --- | --- | --- | --- | --- | --- |
| Gly | Lys | Ser | Gln | Ile | Phe | Asp | Cys | Lys | Asn | His | Val | Arg | Val | Ile | Gln |     |
|     |     |     | 125 |     |     |     |     | 130 |     |     |     |     | 135 |     |     |     |

| TCA | ATG | GAC | CAG | GGG | GAT | AGG | CTC | TAT | GTA | TGC | GGC | ACC | AAC | GCC | CAC | 726 |
| --- | --- | --- | --- | --- | --- | --- | --- | --- | --- | --- | --- | --- | --- | --- | --- | --- |
| Ser | Met | Asp | Gln | Gly | Asp | Arg | Leu | Tyr | Val | Cys | Gly | Thr | Asn | Ala | His |     |

-continued

|     | 140 |     |     |     |     | 145 |     |     |     |     | 150 |     |     |     |     |      |
|-----|-----|-----|-----|-----|-----|-----|-----|-----|-----|-----|-----|-----|-----|-----|-----|------|
| AAT | CCC | AAG | GAT | TAT | GTT | ATC | TAT | GCG | AAT | CTA | ACC | CAC | CTG | CCG | CGC | 774  |
| Asn | Pro | Lys | Asp | Tyr | Val | Ile | Tyr | Ala | Asn | Leu | Thr | His | Leu | Pro | Arg |      |
|     | 155 |     |     |     | 160 |     |     |     |     |     | 165 |     |     |     |     |      |
| TCG | GAA | TAT | GTG | ATT | GGC | GTG | GGT | CTG | GGC | ATT | GCC | AAG | TGC | CCC | TAC | 822  |
| Ser | Glu | Tyr | Val | Ile | Gly | Val | Gly | Leu | Gly | Ile | Ala | Lys | Cys | Pro | Tyr |      |
| 170 |     |     |     |     | 175 |     |     |     |     | 180 |     |     |     |     | 185 |      |
| GAT | CCC | CTC | GAC | AAC | TCA | ACT | GCG | ATT | TAT | GTG | GAG | AAT | GGC | AAT | CCG | 870  |
| Asp | Pro | Leu | Asp | Asn | Ser | Thr | Ala | Ile | Tyr | Val | Glu | Asn | Gly | Asn | Pro |      |
|     |     |     |     | 190 |     |     |     |     | 195 |     |     |     |     | 200 |     |      |
| GGT | GGT | CTG | CCC | GGT | TTG | TAC | TCC | GGC | ACC | AAT | GCG | GAG | TTC | ACC | AAG | 918  |
| Gly | Gly | Leu | Pro | Gly | Leu | Tyr | Ser | Gly | Thr | Asn | Ala | Glu | Phe | Thr | Lys |      |
|     |     |     | 205 |     |     |     |     | 210 |     |     |     |     | 215 |     |     |      |
| GCG | GAT | ACG | GTT | ATT | TTC | CGC | ACT | GAT | CTG | TAT | AAT | ACT | TCG | GCT | AAA | 966  |
| Ala | Asp | Thr | Val | Ile | Phe | Arg | Thr | Asp | Leu | Tyr | Asn | Thr | Ser | Ala | Lys |      |
|     |     | 220 |     |     |     |     | 225 |     |     |     |     | 230 |     |     |     |      |
| CGT | TTG | GAA | TAT | AAA | TTC | AAG | AGG | ACT | CTG | AAA | TAC | GAC | TCC | AAG | TGG | 1014 |
| Arg | Leu | Glu | Tyr | Lys | Phe | Lys | Arg | Thr | Leu | Lys | Tyr | Asp | Ser | Lys | Trp |      |
|     | 235 |     |     |     |     | 240 |     |     |     |     | 245 |     |     |     |     |      |
| TTG | GAC | AAA | CCA | AAC | TTT | GTC | GGC | TCC | TTT | GAT | ATT | GGG | GAG | TAC | GTG | 1062 |
| Leu | Asp | Lys | Pro | Asn | Phe | Val | Gly | Ser | Phe | Asp | Ile | Gly | Glu | Tyr | Val |      |
| 250 |     |     |     |     | 255 |     |     |     |     | 260 |     |     |     |     | 265 |      |
| TAT | TTC | TTT | TTC | CGT | GAA | ACC | GCC | GTG | GAA | TAC | ATC | AAC | TGC | GGC | AAG | 1110 |
| Tyr | Phe | Phe | Phe | Arg | Glu | Thr | Ala | Val | Glu | Tyr | Ile | Asn | Cys | Gly | Lys |      |
|     |     |     |     | 270 |     |     |     |     | 275 |     |     |     |     |     | 280 |      |
| GCT | GTC | TAT | TCG | CGC | ATC | GCA | CGG | GTG | TGC | AAG | AAG | GAT | GTG | GGT | GGA | 1158 |
| Ala | Val | Tyr | Ser | Arg | Ile | Ala | Arg | Val | Cys | Lys | Lys | Asp | Val | Gly | Gly |      |
|     |     |     | 285 |     |     |     |     | 290 |     |     |     |     | 295 |     |     |      |
| AAG | AAT | CTG | CTG | GCC | CAC | AAC | TGG | GCC | ACC | TAC | CTG | AAG | GCC | AGA | CTC | 1206 |
| Lys | Asn | Leu | Leu | Ala | His | Asn | Trp | Ala | Thr | Tyr | Leu | Lys | Ala | Arg | Leu |      |
|     |     |     | 300 |     |     |     |     | 305 |     |     |     |     | 310 |     |     |      |
| AAC | TGC | AGC | ATC | TCC | GGC | GAA | TTT | CCG | TTC | TAT | TTC | AAC | GAG | ATC | CAA | 1254 |
| Asn | Cys | Ser | Ile | Ser | Gly | Glu | Phe | Pro | Phe | Tyr | Phe | Asn | Glu | Ile | Gln |      |
|     |     | 315 |     |     |     |     | 320 |     |     |     |     | 325 |     |     |     |      |
| TCG | GTC | TAC | CAG | CTG | CCC | TCC | GAT | AAG | AGT | CGA | TTC | TTC | GCC | ACA | TTC | 1302 |
| Ser | Val | Tyr | Gln | Leu | Pro | Ser | Asp | Lys | Ser | Arg | Phe | Phe | Ala | Thr | Phe |      |
| 330 |     |     |     |     | 335 |     |     |     |     | 340 |     |     |     |     | 345 |      |
| ACG | ACG | AGC | ACT | AAT | GGC | CTG | ATT | GGA | TCT | GCC | GTA | TGC | AGT | TTC | CAC | 1350 |
| Thr | Thr | Ser | Thr | Asn | Gly | Leu | Ile | Gly | Ser | Ala | Val | Cys | Ser | Phe | His |      |
|     |     |     |     | 350 |     |     |     |     | 355 |     |     |     |     | 360 |     |      |
| ATT | AAC | GAG | ATT | CAG | GCT | GCC | TTC | AAT | GGC | AAA | TTC | AAG | GAG | CAA | TCT | 1398 |
| Ile | Asn | Glu | Ile | Gln | Ala | Ala | Phe | Asn | Gly | Lys | Phe | Lys | Glu | Gln | Ser |      |
|     |     |     | 365 |     |     |     |     | 370 |     |     |     |     | 375 |     |     |      |
| TCA | TCG | AAT | TCC | GCA | TGG | CTG | CCG | GTG | CTT | AAC | TCC | CGG | GTG | CCG | GAA | 1446 |
| Ser | Ser | Asn | Ser | Ala | Trp | Leu | Pro | Val | Leu | Asn | Ser | Arg | Val | Pro | Glu |      |
|     |     | 380 |     |     |     |     | 385 |     |     |     |     | 390 |     |     |     |      |
| CCA | CGG | CCG | GGT | ACA | TGT | GTC | AAC | GAT | ACA | TCA | AAC | CTG | CCC | GAT | ACC | 1494 |
| Pro | Arg | Pro | Gly | Thr | Cys | Val | Asn | Asp | Thr | Ser | Asn | Leu | Pro | Asp | Thr |      |
|     | 395 |     |     |     | 400 |     |     |     |     | 405 |     |     |     |     |     |      |
| GTA | CTG | AAT | TTC | ATC | AGA | TCC | CAT | CCA | CTT | ATG | GAC | AAA | GCC | GTA | AAT | 1542 |
| Val | Leu | Asn | Phe | Ile | Arg | Ser | His | Pro | Leu | Met | Asp | Lys | Ala | Val | Asn |      |
| 410 |     |     |     |     | 415 |     |     |     |     | 420 |     |     |     |     | 425 |      |
| CAC | GAG | CAC | AAC | AAT | CCA | GTC | TAT | TAT | AAA | AGG | GAT | TTG | GTC | TTC | ACC | 1590 |
| His | Glu | His | Asn | Asn | Pro | Val | Tyr | Tyr | Lys | Arg | Asp | Leu | Val | Phe | Thr |      |
|     |     |     |     | 430 |     |     |     |     | 435 |     |     |     |     | 440 |     |      |
| AAG | CTC | GTC | GTT | GAC | AAA | ATT | CGC | ATT | GAC | ATC | CTC | AAC | CAG | GAA | TAC | 1638 |
| Lys | Leu | Val | Val | Asp | Lys | Ile | Arg | Ile | Asp | Ile | Leu | Asn | Gln | Glu | Tyr |      |
|     |     |     | 445 |     |     |     |     | 450 |     |     |     |     | 455 |     |     |      |
| ATT | GTG | TAC | TAT | GTG | GGC | ACC | AAT | CTG | GGT | CGC | ATT | TAC | AAA | ATC | GTG | 1686 |
| Ile | Val | Tyr | Tyr | Val | Gly | Thr | Asn | Leu | Gly | Arg | Ile | Tyr | Lys | Ile | Val |      |

|     |     |     |     |     | 460 |     |     |     |     |     | 465 |     |     |     |     | 470 |      |
|-----|-----|-----|-----|-----|-----|-----|-----|-----|-----|-----|-----|-----|-----|-----|-----|-----|------|
| CAG | TAC | TAC | CGT | AAC | GGA | GAG | TCG | CTG | TCC | AAG | CTT | CTG | GAT | ATC | TTC |     | 1734 |
| Gln | Tyr | Tyr | Arg | Asn | Gly | Glu | Ser | Leu | Ser | Lys | Leu | Leu | Asp | Ile | Phe |     |      |
|     | 475 |     |     |     |     | 480 |     |     |     |     | 485 |     |     |     |     |     |      |
| GAG | GTG | GCT | CCA | AAC | GAG | GCC | ATC | CAA | GTG | ATG | GAA | ATC | AGC | CAG | ACA |     | 1782 |
| Glu | Val | Ala | Pro | Asn | Glu | Ala | Ile | Gln | Val | Met | Glu | Ile | Ser | Gln | Thr |     |      |
| 490 |     |     |     |     | 495 |     |     |     |     | 500 |     |     |     |     | 505 |     |      |
| CGT | AAG | AGC | CTC | TAC | ATT | GGC | ACC | GAT | CAT | CGC | ATC | AAG | CAA | ATC | GAC |     | 1830 |
| Arg | Lys | Ser | Leu | Tyr | Ile | Gly | Thr | Asp | His | Arg | Ile | Lys | Gln | Ile | Asp |     |      |
|     |     |     |     | 510 |     |     |     |     | 515 |     |     |     |     | 520 |     |     |      |
| CTG | GCC | ATG | TGC | AAT | CGC | CGT | TAC | GAC | AAC | TGC | TTC | CGC | TGC | GTC | CGT |     | 1878 |
| Leu | Ala | Met | Cys | Asn | Arg | Arg | Tyr | Asp | Asn | Cys | Phe | Arg | Cys | Val | Arg |     |      |
|     |     |     | 525 |     |     |     |     | 530 |     |     |     |     | 535 |     |     |     |      |
| GAT | CCC | TAC | TGC | GGC | TGG | GAT | AAG | GAG | GCC | AAT | ACG | TGC | CGA | CCG | TAC |     | 1926 |
| Asp | Pro | Tyr | Cys | Gly | Trp | Asp | Lys | Glu | Ala | Asn | Thr | Cys | Arg | Pro | Tyr |     |      |
|     |     | 540 |     |     |     |     | 545 |     |     |     |     | 550 |     |     |     |     |      |
| GAG | CTG | GAT | TTA | CTG | CAG | GAT | GTG | GCC | AAT | GAA | ACG | AGT | GAC | ATT | TGC |     | 1974 |
| Glu | Leu | Asp | Leu | Leu | Gln | Asp | Val | Ala | Asn | Glu | Thr | Ser | Asp | Ile | Cys |     |      |
|     | 555 |     |     |     |     | 560 |     |     |     |     | 565 |     |     |     |     |     |      |
| GAT | TCG | AGT | GTG | CTG | AAA | AAG | AAG | ATT | GTG | GTG | ACC | TAT | GGC | CAG | AGT |     | 2022 |
| Asp | Ser | Ser | Val | Leu | Lys | Lys | Lys | Ile | Val | Val | Thr | Tyr | Gly | Gln | Ser |     |      |
| 570 |     |     |     |     | 575 |     |     |     |     | 580 |     |     |     |     | 585 |     |      |
| GTA | CAT | CTG | GGC | TGT | TTC | GTC | AAA | ATA | CCC | GAA | GTG | CTG | AAG | AAT | GAG |     | 2070 |
| Val | His | Leu | Gly | Cys | Phe | Val | Lys | Ile | Pro | Glu | Val | Leu | Lys | Asn | Glu |     |      |
|     |     |     |     | 590 |     |     |     |     | 595 |     |     |     |     | 600 |     |     |      |
| CAA | GTG | ACC | TGG | TAT | CAT | CAC | TCC | AAG | GAC | AAG | GGA | CGC | TAC | GAG | ATT |     | 2118 |
| Gln | Val | Thr | Trp | Tyr | His | His | Ser | Lys | Asp | Lys | Gly | Arg | Tyr | Glu | Ile |     |      |
|     |     |     | 605 |     |     |     |     | 610 |     |     |     |     | 615 |     |     |     |      |
| CGT | TAC | TCG | CCG | ACC | AAA | TAC | ATT | GAG | ACC | ACC | GAA | CGT | GGC | CTG | GTT |     | 2166 |
| Arg | Tyr | Ser | Pro | Thr | Lys | Tyr | Ile | Glu | Thr | Thr | Glu | Arg | Gly | Leu | Val |     |      |
|     |     | 620 |     |     |     |     | 625 |     |     |     |     | 630 |     |     |     |     |      |
| GTG | GTT | TCC | GTG | AAC | GAA | GCC | GAT | GGT | GGT | CGG | TAC | GAT | TGC | CAT | TTG |     | 2214 |
| Val | Val | Ser | Val | Asn | Glu | Ala | Asp | Gly | Gly | Arg | Tyr | Asp | Cys | His | Leu |     |      |
|     | 635 |     |     |     |     | 640 |     |     |     |     | 645 |     |     |     |     |     |      |
| GGC | GGC | TCG | CTT | TTG | TGC | AGC | TAC | AAC | ATT | ACA | GTG | GAT | GCC | CAC | AGA |     | 2262 |
| Gly | Gly | Ser | Leu | Leu | Cys | Ser | Tyr | Asn | Ile | Thr | Val | Asp | Ala | His | Arg |     |      |
| 650 |     |     |     |     | 655 |     |     |     |     | 660 |     |     |     |     | 665 |     |      |
| TGC | ACT | CCG | CCG | AAC | AAG | AGT | AAT | GAC | TAT | CAG | AAA | ATC | TAC | TCG | GAC |     | 2310 |
| Cys | Thr | Pro | Pro | Asn | Lys | Ser | Asn | Asp | Tyr | Gln | Lys | Ile | Tyr | Ser | Asp |     |      |
|     |     |     |     | 670 |     |     |     |     | 675 |     |     |     |     | 680 |     |     |      |
| TGG | TGC | CAC | GAG | TTC | GAG | AAA | TAC | AAA | ACA | GCA | ATG | AAG | TCC | TGG | GAA |     | 2358 |
| Trp | Cys | His | Glu | Phe | Glu | Lys | Tyr | Lys | Thr | Ala | Met | Lys | Ser | Trp | Glu |     |      |
|     |     |     | 685 |     |     |     |     | 690 |     |     |     |     | 695 |     |     |     |      |
| AAG | AAG | CAA | GGC | CAA | TGC | TCG | ACA | CGG | CAG | AAC | TTC | AGC | TGC | AAT | CAG |     | 2406 |
| Lys | Lys | Gln | Gly | Gln | Cys | Ser | Thr | Arg | Gln | Asn | Phe | Ser | Cys | Asn | Gln |     |      |
|     |     | 700 |     |     |     |     | 705 |     |     |     |     | 710 |     |     |     |     |      |
| CAT | CCG | AAT | GAG | ATT | TTC | CGT | AAG | CCC | AAT | GTC | TGATATCACG | | AAGAGAGTAT | | |     | 2459 |
| His | Pro | Asn | Glu | Ile | Phe | Arg | Lys | Pro | Asn | Val |     |     |     |     |     |     |      |
|     | 715 |     |     |     |     | 720 |     |     |     |     |     |     |     |     |     |     |      |

| CGCCCTCAAA | ATGCCGTCAT | CGTCGTCCAA | TCAATTTTAG | TTAATCGAAA | GCGAAGAGGA | 2519 |
| TAATAACAGT | GCGGAATAGA | AAGCCCAGGA | CGAGAAGAAC | TCATTATAAT | CATTATTATC | 2579 |
| AGCGACATCA | TCATAGACAT | ACTTTCTTCA | GCAATGAACA | GAAAACTCTT | CCTAAAGGAT | 2639 |
| TATGCATTTA | CCGAAGCATT | TACAATGCAT | C |     |     | 2670 |

( 2 ) INFORMATION FOR SEQ ID NO:62:

( i ) SEQUENCE CHARACTERISTICS:
        ( A ) LENGTH: 724 amino acids
        ( B ) TYPE: amino acid ( D ) TOPOLOGY: linear ( i i ) MOLECULE TYPE: protein ( x i ) SEQUENCE DESCRIPTION: SEQ ID NO:62:

```
Met  Ser  Leu  Leu  Gln  Leu  Ser  Pro  Leu  Leu  Ala  Leu  Leu  Leu  Leu  Leu
 1                   5                        10                            15

Cys  Ser  Ser  Val  Ser  Glu  Thr  Ala  Ala  Asp  Tyr  Glu  Asn  Thr  Trp  Asn
               20                       25                        30

Phe  Tyr  Tyr  Glu  Arg  Pro  Cys  Cys  Thr  Gly  Asn  Asp  Gln  Gly  Asn  Asn
                35                  40                        45

Asn  Tyr  Gly  Lys  His  Gly  Ala  Asp  His  Val  Arg  Glu  Phe  Asn  Cys  Gly
          50                       55                  60

Lys  Leu  Tyr  Tyr  Arg  Thr  Phe  His  Met  Asn  Glu  Asp  Arg  Asp  Thr  Leu
 65                       70                       75                       80

Tyr  Val  Gly  Ala  Met  Asp  Arg  Val  Phe  Arg  Val  Asn  Leu  Gln  Asn  Ile
                     85                       90                       95

Ser  Ser  Ser  Asn  Cys  Asn  Arg  Asp  Ala  Ile  Asn  Leu  Glu  Pro  Thr  Arg
               100                      105                      110

Asp  Asp  Val  Val  Ser  Cys  Val  Ser  Lys  Gly  Lys  Ser  Gln  Ile  Phe  Asp
               115                      120                      125

Cys  Lys  Asn  His  Val  Arg  Val  Ile  Gln  Ser  Met  Asp  Gln  Gly  Asp  Arg
     130                      135                      140

Leu  Tyr  Val  Cys  Gly  Thr  Asn  Ala  His  Asn  Pro  Lys  Asp  Tyr  Val  Ile
145                           150                      155                 160

Tyr  Ala  Asn  Leu  Thr  His  Leu  Pro  Arg  Ser  Glu  Tyr  Val  Ile  Gly  Val
                    165                      170                      175

Gly  Leu  Gly  Ile  Ala  Lys  Cys  Pro  Tyr  Asp  Pro  Leu  Asp  Asn  Ser  Thr
               180                      185                      190

Ala  Ile  Tyr  Val  Glu  Asn  Gly  Asn  Pro  Gly  Gly  Leu  Pro  Gly  Leu  Tyr
          195                      200                      205

Ser  Gly  Thr  Asn  Ala  Glu  Phe  Thr  Lys  Ala  Asp  Thr  Val  Ile  Phe  Arg
     210                      215                      220

Thr  Asp  Leu  Tyr  Asn  Thr  Ser  Ala  Lys  Arg  Leu  Glu  Tyr  Lys  Phe  Lys
225                           230                      235                 240

Arg  Thr  Leu  Lys  Tyr  Asp  Ser  Lys  Trp  Leu  Asp  Lys  Pro  Asn  Phe  Val
                    245                      250                      255

Gly  Ser  Phe  Asp  Ile  Gly  Glu  Tyr  Val  Tyr  Phe  Phe  Phe  Arg  Glu  Thr
               260                      265                      270

Ala  Val  Glu  Tyr  Ile  Asn  Cys  Gly  Lys  Ala  Val  Tyr  Ser  Arg  Ile  Ala
          275                      280                      285

Arg  Val  Cys  Lys  Lys  Asp  Val  Gly  Gly  Lys  Asn  Leu  Leu  Ala  His  Asn
     290                      295                      300

Trp  Ala  Thr  Tyr  Leu  Lys  Ala  Arg  Leu  Asn  Cys  Ser  Ile  Ser  Gly  Glu
305                      310                      315                      320

Phe  Pro  Phe  Tyr  Phe  Asn  Glu  Ile  Gln  Ser  Val  Tyr  Gln  Leu  Pro  Ser
                    325                      330                      335

Asp  Lys  Ser  Arg  Phe  Phe  Ala  Thr  Phe  Thr  Thr  Ser  Thr  Asn  Gly  Leu
               340                      345                      350

Ile  Gly  Ser  Ala  Val  Cys  Ser  Phe  His  Ile  Asn  Glu  Ile  Gln  Ala  Ala
          355                      360                      365

Phe  Asn  Gly  Lys  Phe  Lys  Glu  Gln  Ser  Ser  Ser  Asn  Ser  Ala  Trp  Leu
     370                      375                      380

Pro  Val  Leu  Asn  Ser  Arg  Val  Pro  Glu  Pro  Arg  Pro  Gly  Thr  Cys  Val
385                      390                      395                      400
```

| | | | | | | | | | | | | | | |
|---|---|---|---|---|---|---|---|---|---|---|---|---|---|---|
|Asn|Asp|Thr|Ser|Asn<br>405|Leu|Pro|Asp|Thr|Val<br>410|Leu|Asn|Phe|Ile|Arg<br>415|Ser|

| | | | | | | | | | | | | | | | |
|---|---|---|---|---|---|---|---|---|---|---|---|---|---|---|---|
|His|Pro|Leu|Met<br>420|Asp|Lys|Ala|Val|Asn<br>425|His|Glu|His|Asn|Asn<br>430|Pro|Val|
|Tyr|Tyr|Lys<br>435|Arg|Asp|Leu|Val|Phe<br>440|Thr|Lys|Leu|Val|Val<br>445|Asp|Lys|Ile|
|Arg|Ile<br>450|Asp|Ile|Leu|Asn|Gln<br>455|Glu|Tyr|Ile|Val|Tyr<br>460|Tyr|Val|Gly|Thr|
|Asn<br>465|Leu|Gly|Arg|Ile|Tyr<br>470|Lys|Ile|Val|Gln|Tyr<br>475|Tyr|Arg|Asn|Gly|Glu<br>480|
|Ser|Leu|Ser|Lys|Leu<br>485|Leu|Asp|Ile|Phe|Glu<br>490|Val|Ala|Pro|Asn|Glu<br>495|Ala|
|Ile|Gln|Val|Met<br>500|Glu|Ile|Ser|Gln|Thr<br>505|Arg|Lys|Ser|Leu|Tyr<br>510|Ile|Gly|
|Thr|Asp|His<br>515|Arg|Ile|Lys|Gln|Ile<br>520|Asp|Leu|Ala|Met|Cys<br>525|Asn|Arg|Arg|
|Tyr|Asp<br>530|Asn|Cys|Phe|Arg|Cys<br>535|Val|Arg|Asp|Pro|Tyr<br>540|Cys|Gly|Trp|Asp|
|Lys<br>545|Glu|Ala|Asn|Thr|Cys<br>550|Arg|Pro|Tyr|Glu|Leu<br>555|Asp|Leu|Leu|Gln|Asp<br>560|
|Val|Ala|Asn|Glu|Thr<br>565|Ser|Asp|Ile|Cys|Asp<br>570|Ser|Ser|Val|Leu|Lys<br>575|Lys|
|Lys|Ile|Val|Val<br>580|Thr|Tyr|Gly|Gln|Ser<br>585|Val|His|Leu|Gly|Cys<br>590|Phe|Val|
|Lys|Ile|Pro<br>595|Glu|Val|Leu|Lys|Asn<br>600|Glu|Gln|Val|Thr|Trp<br>605|Tyr|His|His|
|Ser|Lys<br>610|Asp|Lys|Gly|Arg|Tyr<br>615|Glu|Ile|Arg|Tyr|Ser<br>620|Pro|Thr|Lys|Tyr|
|Ile<br>625|Glu|Thr|Thr|Glu|Arg<br>630|Gly|Leu|Val|Val|Val<br>635|Ser|Val|Asn|Glu|Ala<br>640|
|Asp|Gly|Gly|Arg|Tyr<br>645|Asp|Cys|His|Leu|Gly<br>650|Gly|Ser|Leu|Leu|Cys<br>655|Ser|
|Tyr|Asn|Ile|Thr<br>660|Val|Asp|Ala|His|Arg<br>665|Cys|Thr|Pro|Pro|Asn<br>670|Lys|Ser|
|Asn|Asp|Tyr<br>675|Gln|Lys|Ile|Tyr|Ser<br>680|Asp|Trp|Cys|His|Glu<br>685|Phe|Glu|Lys|
|Tyr|Lys<br>690|Thr|Ala|Met|Lys|Ser<br>695|Trp|Glu|Lys|Lys|Gln<br>700|Gly|Gln|Cys|Ser|
|Thr<br>705|Arg|Gln|Asn|Phe|Ser<br>710|Cys|Asn|Gln|His|Pro<br>715|Asn|Glu|Ile|Phe|Arg<br>720|
|Lys|Pro|Asn|Val| | | | | | | | | | | | |

( 2 ) INFORMATION FOR SEQ ID NO:63:

( i ) SEQUENCE CHARACTERISTICS:
    ( A ) LENGTH: 2504 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 355..2493

( x i ) SEQUENCE DESCRIPTION: SEQ ID NO:63:

-continued

```
GGCCGGTCGA CCACGAGCGA AGTTTAGTAT CAAGTTGAGA GTTTGTTTGG AGCGTAGTTT    60

ACGGAGCGTA CATTTAAATT TGCGGACAAA TCGTGTTTTG GTGCTTCTCT GTGGATTGTT   120

GTGTTCTTGA AGATGCTTCC CTTGGTTTTC GGATAAGCTT TCCTGTGGAT TGTTGTGTTC   180

TTGAAGATGC TTCCCTTGGT TTTCGGATAA GCTTTCCAGC GTGGTTTCAG CCTCGGCTTG   240

TTTGGACCCC GACATAATCT TCGAACTACA ATGAAGAGGA AATTTTGAAA CGCGTTTCAG   300

ACGCGTACAA TCGACAAAAT GTTTGGTTTC CAATTGATCT TGCAATGTAG CTAC ATG    357
                                                              Met
                                                               1
```

| GTG | GTG | AAG | ATC | TTG | GTT | TGG | TCG | ATA | TGT | CTG | ATA | GCG | CTG | TGT | CAT | 405 |
|---|---|---|---|---|---|---|---|---|---|---|---|---|---|---|---|---|
| Val | Val | Lys | Ile | Leu | Val | Trp | Ser | Ile | Cys | Leu | Ile | Ala | Leu | Cys | His | |
| | | | | 5 | | | | 10 | | | | | 15 | | | |

| GCT | TGG | ATG | CCG | GAT | AGT | TCT | TCC | AAA | TTA | ATA | AAC | CAT | TTT | AAA | TCA | 453 |
|---|---|---|---|---|---|---|---|---|---|---|---|---|---|---|---|---|
| Ala | Trp | Met | Pro | Asp | Ser | Ser | Ser | Lys | Leu | Ile | Asn | His | Phe | Lys | Ser | |
| | | 20 | | | | | 25 | | | | | 30 | | | | |

| GTT | GAA | AGT | AAA | AGC | TTT | ACC | GGG | AAC | GCC | ACG | TTC | CCT | GAT | CAC | TTT | 501 |
|---|---|---|---|---|---|---|---|---|---|---|---|---|---|---|---|---|
| Val | Glu | Ser | Lys | Ser | Phe | Thr | Gly | Asn | Ala | Thr | Phe | Pro | Asp | His | Phe | |
| | | 35 | | | | | 40 | | | | | 45 | | | | |

| ATT | GTC | TTG | AAT | CAA | GAC | GAA | ACT | TCG | ATA | TTA | GTA | GGC | GGT | AGA | AAT | 549 |
|---|---|---|---|---|---|---|---|---|---|---|---|---|---|---|---|---|
| Ile | Val | Leu | Asn | Gln | Asp | Glu | Thr | Ser | Ile | Leu | Val | Gly | Gly | Arg | Asn | |
| 50 | | | | | 55 | | | | | 60 | | | | | 65 | |

| AGG | GTT | TAC | AAT | TTA | AGT | ATA | TTC | GAC | CTC | AGT | GAG | CGT | AAA | GGG | GGG | 597 |
|---|---|---|---|---|---|---|---|---|---|---|---|---|---|---|---|---|
| Arg | Val | Tyr | Asn | Leu | Ser | Ile | Phe | Asp | Leu | Ser | Glu | Arg | Lys | Gly | Gly | |
| | | | | 70 | | | | | 75 | | | | | 80 | | |

| CGA | ATC | GAC | TGG | CCA | TCG | TCC | GAT | GCA | CAT | GGC | CAG | TTG | TGT | ATA | TTG | 645 |
|---|---|---|---|---|---|---|---|---|---|---|---|---|---|---|---|---|
| Arg | Ile | Asp | Trp | Pro | Ser | Ser | Asp | Ala | His | Gly | Gln | Leu | Cys | Ile | Leu | |
| | | | 85 | | | | | 90 | | | | | 95 | | | |

| AAA | GGG | AAA | ACG | GAC | GAC | GAC | TGC | CAA | AAT | TAC | ATT | AGA | ATA | CTG | TAC | 693 |
|---|---|---|---|---|---|---|---|---|---|---|---|---|---|---|---|---|
| Lys | Gly | Lys | Thr | Asp | Asp | Asp | Cys | Gln | Asn | Tyr | Ile | Arg | Ile | Leu | Tyr | |
| | | 100 | | | | | 105 | | | | | 110 | | | | |

| TCT | TCA | GAA | CCG | GGG | AAA | TTA | GTT | ATT | TGC | GGG | ACC | AAT | TCG | TAC | AAA | 741 |
|---|---|---|---|---|---|---|---|---|---|---|---|---|---|---|---|---|
| Ser | Ser | Glu | Pro | Gly | Lys | Leu | Val | Ile | Cys | Gly | Thr | Asn | Ser | Tyr | Lys | |
| | | 115 | | | | | 120 | | | | | 125 | | | | |

| CCC | CTC | TGT | CGG | ACG | TAC | GCA | TTT | AAG | GAG | GGA | AAG | TAC | CTG | GTT | GAG | 789 |
|---|---|---|---|---|---|---|---|---|---|---|---|---|---|---|---|---|
| Pro | Leu | Cys | Arg | Thr | Tyr | Ala | Phe | Lys | Glu | Gly | Lys | Tyr | Leu | Val | Glu | |
| 130 | | | | | 135 | | | | | 140 | | | | | 145 | |

| AAA | GAA | GTA | GAA | GGG | ATA | GGC | TTG | TGT | CCA | TAC | AAT | CCG | GAA | CAC | AAC | 837 |
|---|---|---|---|---|---|---|---|---|---|---|---|---|---|---|---|---|
| Lys | Glu | Val | Glu | Gly | Ile | Gly | Leu | Cys | Pro | Tyr | Asn | Pro | Glu | His | Asn | |
| | | | | 150 | | | | | 155 | | | | | 160 | | |

| AGC | ACA | TCT | GTC | TCC | TAC | AAT | GGC | CAA | TTA | TTT | TCA | GCG | ACG | GTC | GCC | 885 |
|---|---|---|---|---|---|---|---|---|---|---|---|---|---|---|---|---|
| Ser | Thr | Ser | Val | Ser | Tyr | Asn | Gly | Gln | Leu | Phe | Ser | Ala | Thr | Val | Ala | |
| | | | 165 | | | | | 170 | | | | | 175 | | | |

| GAC | TTT | TCC | GGG | GGC | GAC | CCT | CTC | ATA | TAC | AGG | GAG | CCC | CAG | CGC | ACC | 933 |
|---|---|---|---|---|---|---|---|---|---|---|---|---|---|---|---|---|
| Asp | Phe | Ser | Gly | Gly | Asp | Pro | Leu | Ile | Tyr | Arg | Glu | Pro | Gln | Arg | Thr | |
| | | 180 | | | | | 185 | | | | | 190 | | | | |

| GAA | CTC | TCA | GAT | CTC | AAA | CAA | CTG | AAC | GCA | CCG | AAT | TTC | GTA | AAC | TCG | 981 |
|---|---|---|---|---|---|---|---|---|---|---|---|---|---|---|---|---|
| Glu | Leu | Ser | Asp | Leu | Lys | Gln | Leu | Asn | Ala | Pro | Asn | Phe | Val | Asn | Ser | |
| 195 | | | | | 200 | | | | | 205 | | | | | | |

| GTG | GCC | TAT | GGC | GAC | TAC | ATA | TTC | TTC | TTC | TAC | CGT | GAA | ACC | GCC | GTC | 1029 |
|---|---|---|---|---|---|---|---|---|---|---|---|---|---|---|---|---|
| Val | Ala | Tyr | Gly | Asp | Tyr | Ile | Phe | Phe | Phe | Tyr | Arg | Glu | Thr | Ala | Val | |
| 210 | | | | | 215 | | | | | 220 | | | | | 225 | |

| GAG | TAC | ATG | AAC | TGC | GGA | AAA | GTC | ATC | TAC | TCG | CGG | GTC | GCC | AGG | GTG | 1077 |
|---|---|---|---|---|---|---|---|---|---|---|---|---|---|---|---|---|
| Glu | Tyr | Met | Asn | Cys | Gly | Lys | Val | Ile | Tyr | Ser | Arg | Val | Ala | Arg | Val | |
| | | | | 230 | | | | | 235 | | | | | 240 | | |

| TGC | AAG | GAC | GAC | AAA | GGG | GGC | CCT | CAC | CAG | TCA | CGC | GAC | CGC | TGG | ACG | 1125 |
|---|---|---|---|---|---|---|---|---|---|---|---|---|---|---|---|---|
| Cys | Lys | Asp | Asp | Lys | Gly | Gly | Pro | His | Gln | Ser | Arg | Asp | Arg | Trp | Thr | |
| | | | 245 | | | | | 250 | | | | | 255 | | | |

| TCG | TTC | CTC | AAA | GCA | CGT | CTC | AAT | TGT | TCA | ATT | CCC | GGC | GAG | TAC | CCC | 1173 |
|---|---|---|---|---|---|---|---|---|---|---|---|---|---|---|---|---|
| Ser | Phe | Leu | Lys | Ala | Arg | Leu | Asn | Cys | Ser | Ile | Pro | Gly | Glu | Tyr | Pro | |

```
                           260                           265                              270
TTT  TAC  TTT  GAT  GAA  ATC  CAA  TCA  ACA  AGT  GAT  ATA  GTC  GAG  GGT  CGG        1221
Phe  Tyr  Phe  Asp  Glu  Ile  Gln  Ser  Thr  Ser  Asp  Ile  Val  Glu  Gly  Arg
     275                      280                     285

TAC  AAT  TCC  GAC  GAC  AGC  AAA  AAG  ATC  ATT  TAT  GGA  ATC  CTC  ACA  ACT        1269
Tyr  Asn  Ser  Asp  Asp  Ser  Lys  Lys  Ile  Ile  Tyr  Gly  Ile  Leu  Thr  Thr
290                           295                     300                     305

CCA  GTT  AAT  GCC  ATC  GGC  GGC  TCG  GCC  ATT  TGC  GCG  TAT  CAA  ATG  GCC        1317
Pro  Val  Asn  Ala  Ile  Gly  Gly  Ser  Ala  Ile  Cys  Ala  Tyr  Gln  Met  Ala
                         310                     315                          320

GAC  ATC  TTG  CGC  GTG  TTT  GAA  GGG  AGC  TTC  AAG  CAC  CAA  GAG  ACG  ATC        1365
Asp  Ile  Leu  Arg  Val  Phe  Glu  Gly  Ser  Phe  Lys  His  Gln  Glu  Thr  Ile
               325                     330                     335

AAC  TCG  AAC  TGG  CTC  CCC  GTG  CCC  CAG  AAC  CTA  GTC  CCT  GAA  CCC  AGG        1413
Asn  Ser  Asn  Trp  Leu  Pro  Val  Pro  Gln  Asn  Leu  Val  Pro  Glu  Pro  Arg
          340                     345                     350

CCC  GGG  CAG  TGC  GTA  CGC  GAC  AGC  AGG  ATC  CTG  CCC  GAC  AAG  AAC  GTC        1461
Pro  Gly  Gln  Cys  Val  Arg  Asp  Ser  Arg  Ile  Leu  Pro  Asp  Lys  Asn  Val
     355                     360                     365

AAC  TTT  ATT  AAG  ACC  CAC  TCT  TTG  ATG  GAG  GAC  GTT  CCG  GCT  CTT  TTC        1509
Asn  Phe  Ile  Lys  Thr  His  Ser  Leu  Met  Glu  Asp  Val  Pro  Ala  Leu  Phe
370                      375                     380                          385

GGA  AAA  CCA  GTT  CTG  GTC  CGA  GTG  AGT  CTG  CAG  TAT  CGG  TTT  ACA  GCC        1557
Gly  Lys  Pro  Val  Leu  Val  Arg  Val  Ser  Leu  Gln  Tyr  Arg  Phe  Thr  Ala
                         390                     395                          400

ATA  ACA  GTG  GAT  CCA  CAA  GTG  AAA  ACA  ATC  AAT  AAT  CAG  TAT  CTC  GAT        1605
Ile  Thr  Val  Asp  Pro  Gln  Val  Lys  Thr  Ile  Asn  Asn  Gln  Tyr  Leu  Asp
               405                     410                     415

GTT  TTG  TAT  ATC  GGA  ACA  GAT  GAT  GGG  AAG  GTA  CTA  AAA  GCT  GTT  AAT        1653
Val  Leu  Tyr  Ile  Gly  Thr  Asp  Asp  Gly  Lys  Val  Leu  Lys  Ala  Val  Asn
          420                     425                     430

ATA  CCA  AAG  CGA  CAC  GCT  AAA  GCG  TTG  TTA  TAT  CGA  AAA  TAC  CGT  ACA        1701
Ile  Pro  Lys  Arg  His  Ala  Lys  Ala  Leu  Leu  Tyr  Arg  Lys  Tyr  Arg  Thr
     435                     440                     445

TCC  GTA  CAT  CCG  CAC  GGA  GCT  CCC  GTA  AAA  CAG  CTG  AAG  ATC  GCT  CCC        1749
Ser  Val  His  Pro  His  Gly  Ala  Pro  Val  Lys  Gln  Leu  Lys  Ile  Ala  Pro
450                      455                     460                          465

GGT  TAT  GGC  AAA  GTT  GTG  GTG  GTC  GGG  AAA  GAC  GAA  ATC  AGA  CTT  GCT        1797
Gly  Tyr  Gly  Lys  Val  Val  Val  Val  Gly  Lys  Asp  Glu  Ile  Arg  Leu  Ala
                         470                     475                          480

AAT  CTC  AAC  CAT  TGT  GCA  AGC  AAA  ACG  CGG  TGC  AAG  GAC  TGT  GTG  GAA        1845
Asn  Leu  Asn  His  Cys  Ala  Ser  Lys  Thr  Arg  Cys  Lys  Asp  Cys  Val  Glu
               485                     490                     495

CTG  CAA  GAC  CCA  CAT  TGC  GCC  TGG  GAC  GCC  AAA  CAA  AAC  CTG  TGT  GTC        1893
Leu  Gln  Asp  Pro  His  Cys  Ala  Trp  Asp  Ala  Lys  Gln  Asn  Leu  Cys  Val
          500                     505                     510

AGC  ATT  GAC  ACC  GTC  ACT  TCG  TAT  CGC  TTC  CTG  ATC  CAG  GAC  GTA  GTT        1941
Ser  Ile  Asp  Thr  Val  Thr  Ser  Tyr  Arg  Phe  Leu  Ile  Gln  Asp  Val  Val
     515                     520                     525

CGC  GGC  GAC  GAC  AAC  AAA  TGT  TGG  TCG  CCG  CAA  ACA  GAC  AAA  AAG  ACT        1989
Arg  Gly  Asp  Asp  Asn  Lys  Cys  Trp  Ser  Pro  Gln  Thr  Asp  Lys  Lys  Thr
530                      535                     540                          545

GTG  ATT  AAG  AAT  AAG  CCC  AGC  GAG  GTT  GAG  AAC  GAG  ATT  ACG  AAC  TCC        2037
Val  Ile  Lys  Asn  Lys  Pro  Ser  Glu  Val  Glu  Asn  Glu  Ile  Thr  Asn  Ser
                         550                     555                          560

ATT  GAC  GAA  AAG  GAT  CTC  GAT  TCA  AGC  GAT  CCG  CTC  ATC  AAA  ACT  GGT        2085
Ile  Asp  Glu  Lys  Asp  Leu  Asp  Ser  Ser  Asp  Pro  Leu  Ile  Lys  Thr  Gly
               565                     570                     575

CTC  GAT  GAC  GAT  TCC  GAT  TGT  GAT  CCA  GTC  AGC  GAG  AAC  AGC  ATA  GGC        2133
Leu  Asp  Asp  Asp  Ser  Asp  Cys  Asp  Pro  Val  Ser  Glu  Asn  Ser  Ile  Gly
```

|     |     |     |     |     | 580 |     |     |     |     | 585 |     |     |     |     | 590 |     |      |
|-----|-----|-----|-----|-----|-----|-----|-----|-----|-----|-----|-----|-----|-----|-----|-----|-----|------|
| GGA | TGC | GCC | GTC | CGC | CAG | CAA | CTT | GTT | ATA | TAC | ACA | GCT | GGG | ACT | CTA |     | 2181 |
| Gly | Cys | Ala | Val | Arg | Gln | Gln | Leu | Val | Ile | Tyr | Thr | Ala | Gly | Thr | Leu |     |      |
|     | 595 |     |     |     |     | 600 |     |     |     |     | 605 |     |     |     |     |     |      |
| CAC | ATT | GTC | GTG | GTC | GTC | GTC | AGC | ATC | GTG | GGT | TTA | TTT | TCT | TGG | CTT |     | 2229 |
| His | Ile | Val | Val | Val | Val | Val | Ser | Ile | Val | Gly | Leu | Phe | Ser | Trp | Leu |     |      |
| 610 |     |     |     |     | 615 |     |     |     |     | 620 |     |     |     |     | 625 |     |      |
| TAT | AGC | GGG | TTA | TCT | GTT | TTC | GCA | AAA | TTT | CAC | TCG | GAT | TCG | CAA | TAT |     | 2277 |
| Tyr | Ser | Gly | Leu | Ser | Val | Phe | Ala | Lys | Phe | His | Ser | Asp | Ser | Gln | Tyr |     |      |
|     |     |     |     | 630 |     |     |     |     | 635 |     |     |     |     | 640 |     |     |      |
| CCT | GAG | GCG | CCG | TTT | ATA | GAG | CAG | CAC | AAT | CAT | TTG | GAA | AGA | TTA | AGC |     | 2325 |
| Pro | Glu | Ala | Pro | Phe | Ile | Glu | Gln | His | Asn | His | Leu | Glu | Arg | Leu | Ser |     |      |
|     |     |     | 645 |     |     |     |     | 650 |     |     |     |     | 655 |     |     |     |      |
| GCC | AAC | CAG | ACG | GGG | TAT | TTG | ACT | CCG | AGG | GCC | AAT | AAA | GCG | GTC | AAT |     | 2373 |
| Ala | Asn | Gln | Thr | Gly | Tyr | Leu | Thr | Pro | Arg | Ala | Asn | Lys | Ala | Val | Asn |     |      |
|     |     | 660 |     |     |     |     | 665 |     |     |     |     | 670 |     |     |     |     |      |
| TTG | GTG | GTG | AAG | GTG | TCT | AGT | AGC | ACG | CCG | CGG | CCG | AAA | AAG | GAC | AAT |     | 2421 |
| Leu | Val | Val | Lys | Val | Ser | Ser | Ser | Thr | Pro | Arg | Pro | Lys | Lys | Asp | Asn |     |      |
|     |     | 675 |     |     |     |     | 680 |     |     |     |     | 685 |     |     |     |     |      |
| CTC | GAT | GTC | AGC | AAA | GAC | TTG | AAC | ATT | GCG | AGT | GAC | GGG | ACT | TTG | CAA |     | 2469 |
| Leu | Asp | Val | Ser | Lys | Asp | Leu | Asn | Ile | Ala | Ser | Asp | Gly | Thr | Leu | Gln |     |      |
| 690 |     |     |     |     | 695 |     |     |     |     | 700 |     |     |     |     | 705 |     |      |
| AAA | ATC | AAG | AAG | ACT | TAC | ATT | TAGTGCGACT | TTTT |  |  |  |  |  |  |  |  | 2504 |
| Lys | Ile | Lys | Lys | Thr | Tyr | Ile |  |  |  |  |  |  |  |  |  |  |      |
|     |     |     |     | 710 |     |     |  |  |  |  |  |  |  |  |  |  |      |

( 2 ) INFORMATION FOR SEQ ID NO:64:

( i ) SEQUENCE CHARACTERISTICS:
        ( A ) LENGTH: 712 amino acids
        ( B ) TYPE: amino acid
        ( D ) TOPOLOGY: linear ( i i ) MOLECULE TYPE: protein ( x i ) SEQUENCE DESCRIPTION: SEQ ID NO:64:

| Met | Val | Val | Lys | Ile | Leu | Val | Trp | Ser | Ile | Cys | Leu | Ile | Ala | Leu | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| His | Ala | Trp | Met | Pro | Asp | Ser | Ser | Lys | Leu | Ile | Asn | His | Phe | Lys |     |
|     |     |     | 20  |     |     |     |     | 25  |     |     |     |     | 30  |     |     |
| Ser | Val | Glu | Ser | Lys | Ser | Phe | Thr | Gly | Asn | Ala | Thr | Phe | Pro | Asp | His |
|     |     |     | 35  |     |     |     |     | 40  |     |     |     |     | 45  |     |     |
| Phe | Ile | Val | Leu | Asn | Gln | Asp | Glu | Thr | Ser | Ile | Leu | Val | Gly | Gly | Arg |
|     |     | 50  |     |     |     |     | 55  |     |     |     |     | 60  |     |     |     |
| Asn | Arg | Val | Tyr | Asn | Leu | Ser | Ile | Phe | Asp | Leu | Ser | Glu | Arg | Lys | Gly |
| 65  |     |     |     |     | 70  |     |     |     |     | 75  |     |     |     |     | 80  |
| Gly | Arg | Ile | Asp | Trp | Pro | Ser | Ser | Asp | Ala | His | Gly | Gln | Leu | Cys | Ile |
|     |     |     |     | 85  |     |     |     |     | 90  |     |     |     |     | 95  |     |
| Leu | Lys | Gly | Lys | Thr | Asp | Asp | Asp | Cys | Gln | Asn | Tyr | Ile | Arg | Ile | Leu |
|     |     |     | 100 |     |     |     |     | 105 |     |     |     |     | 110 |     |     |
| Tyr | Ser | Ser | Glu | Pro | Gly | Lys | Leu | Val | Ile | Cys | Gly | Thr | Asn | Ser | Tyr |
|     |     |     | 115 |     |     |     |     | 120 |     |     |     |     | 125 |     |     |
| Lys | Pro | Leu | Cys | Arg | Thr | Tyr | Ala | Phe | Lys | Glu | Gly | Lys | Tyr | Leu | Val |
|     |     | 130 |     |     |     |     | 135 |     |     |     |     | 140 |     |     |     |
| Glu | Lys | Glu | Val | Glu | Gly | Ile | Gly | Leu | Cys | Pro | Tyr | Asn | Pro | Glu | His |
| 145 |     |     |     |     | 150 |     |     |     |     | 155 |     |     |     |     | 160 |
| Asn | Ser | Thr | Ser | Val | Ser | Tyr | Asn | Gly | Gln | Leu | Phe | Ser | Ala | Thr | Val |
|     |     |     |     | 165 |     |     |     |     | 170 |     |     |     |     | 175 |     |
| Ala | Asp | Phe | Ser | Gly | Gly | Asp | Pro | Leu | Ile | Tyr | Arg | Glu | Pro | Gln | Arg |

|   |   |   | 180 |   |   |   |   | 185 |   |   |   |   | 190 |   |   |
|---|---|---|---|---|---|---|---|---|---|---|---|---|---|---|---|
| Thr | Glu | Leu | Ser | Asp | Leu | Lys | Gln | Leu | Asn | Ala | Pro | Asn | Phe | Val | Asn |
|   |   | 195 |   |   |   |   | 200 |   |   |   |   | 205 |   |   |   |
| Ser | Val | Ala | Tyr | Gly | Asp | Tyr | Ile | Phe | Phe | Phe | Tyr | Arg | Glu | Thr | Ala |
|   | 210 |   |   |   |   | 215 |   |   |   |   | 220 |   |   |   |   |
| Val | Glu | Tyr | Met | Asn | Cys | Gly | Lys | Val | Ile | Tyr | Ser | Arg | Val | Ala | Arg |
| 225 |   |   |   |   | 230 |   |   |   |   | 235 |   |   |   |   | 240 |
| Val | Cys | Lys | Asp | Asp | Lys | Gly | Gly | Pro | His | Gln | Ser | Arg | Asp | Arg | Trp |
|   |   |   |   | 245 |   |   |   |   | 250 |   |   |   |   | 255 |   |
| Thr | Ser | Phe | Leu | Lys | Ala | Arg | Leu | Asn | Cys | Ser | Ile | Pro | Gly | Glu | Tyr |
|   |   |   |   | 260 |   |   |   |   | 265 |   |   |   |   | 270 |   |
| Pro | Phe | Tyr | Phe | Asp | Glu | Ile | Gln | Ser | Thr | Ser | Asp | Ile | Val | Glu | Gly |
|   |   | 275 |   |   |   |   | 280 |   |   |   |   | 285 |   |   |   |
| Arg | Tyr | Asn | Ser | Asp | Asp | Ser | Lys | Lys | Ile | Ile | Tyr | Gly | Ile | Leu | Thr |
|   |   | 290 |   |   |   |   | 295 |   |   |   |   | 300 |   |   |   |
| Thr | Pro | Val | Asn | Ala | Ile | Gly | Gly | Ser | Ala | Ile | Cys | Ala | Tyr | Gln | Met |
| 305 |   |   |   |   | 310 |   |   |   |   | 315 |   |   |   |   | 320 |
| Ala | Asp | Ile | Leu | Arg | Val | Phe | Glu | Gly | Ser | Phe | Lys | His | Gln | Glu | Thr |
|   |   |   |   | 325 |   |   |   |   | 330 |   |   |   |   | 335 |   |
| Ile | Asn | Ser | Asn | Trp | Leu | Pro | Val | Pro | Gln | Asn | Leu | Val | Pro | Glu | Pro |
|   |   |   | 340 |   |   |   |   | 345 |   |   |   |   | 350 |   |   |
| Arg | Pro | Gly | Gln | Cys | Val | Arg | Asp | Ser | Arg | Ile | Leu | Pro | Asp | Lys | Asn |
|   |   | 355 |   |   |   |   | 360 |   |   |   |   | 365 |   |   |   |
| Val | Asn | Phe | Ile | Lys | Thr | His | Ser | Leu | Met | Glu | Asp | Val | Pro | Ala | Leu |
|   | 370 |   |   |   |   | 375 |   |   |   |   | 380 |   |   |   |   |
| Phe | Gly | Lys | Pro | Val | Leu | Val | Arg | Val | Ser | Leu | Gln | Tyr | Arg | Phe | Thr |
| 385 |   |   |   |   | 390 |   |   |   |   | 395 |   |   |   |   | 400 |
| Ala | Ile | Thr | Val | Asp | Pro | Gln | Val | Lys | Thr | Ile | Asn | Asn | Gln | Tyr | Leu |
|   |   |   |   | 405 |   |   |   |   | 410 |   |   |   |   | 415 |   |
| Asp | Val | Leu | Tyr | Ile | Gly | Thr | Asp | Asp | Gly | Lys | Val | Leu | Lys | Ala | Val |
|   |   |   | 420 |   |   |   |   | 425 |   |   |   |   | 430 |   |   |
| Asn | Ile | Pro | Lys | Arg | His | Ala | Lys | Ala | Leu | Leu | Tyr | Arg | Lys | Tyr | Arg |
|   |   | 435 |   |   |   |   | 440 |   |   |   |   | 445 |   |   |   |
| Thr | Ser | Val | His | Pro | His | Gly | Ala | Pro | Val | Lys | Gln | Leu | Lys | Ile | Ala |
|   | 450 |   |   |   |   | 455 |   |   |   |   | 460 |   |   |   |   |
| Pro | Gly | Tyr | Gly | Lys | Val | Val | Val | Gly | Lys | Asp | Glu | Ile | Arg | Leu |   |
| 465 |   |   |   |   | 470 |   |   |   |   | 475 |   |   |   | 480 |   |
| Ala | Asn | Leu | Asn | His | Cys | Ala | Ser | Lys | Thr | Arg | Cys | Lys | Asp | Cys | Val |
|   |   |   |   | 485 |   |   |   |   | 490 |   |   |   |   | 495 |   |
| Glu | Leu | Gln | Asp | Pro | His | Cys | Ala | Trp | Asp | Ala | Lys | Gln | Asn | Leu | Cys |
|   |   |   | 500 |   |   |   |   | 505 |   |   |   |   | 510 |   |   |
| Val | Ser | Ile | Asp | Thr | Val | Thr | Ser | Tyr | Arg | Phe | Leu | Ile | Gln | Asp | Val |
|   |   | 515 |   |   |   |   | 520 |   |   |   |   | 525 |   |   |   |
| Val | Arg | Gly | Asp | Asp | Asn | Lys | Cys | Trp | Ser | Pro | Gln | Thr | Asp | Lys | Lys |
|   | 530 |   |   |   |   | 535 |   |   |   |   | 540 |   |   |   |   |
| Thr | Val | Ile | Lys | Asn | Lys | Pro | Ser | Glu | Val | Glu | Asn | Glu | Ile | Thr | Asn |
| 545 |   |   |   |   | 550 |   |   |   |   | 555 |   |   |   |   | 560 |
| Ser | Ile | Asp | Glu | Lys | Asp | Leu | Asp | Ser | Ser | Asp | Pro | Leu | Ile | Lys | Thr |
|   |   |   |   | 565 |   |   |   |   | 570 |   |   |   |   | 575 |   |
| Gly | Leu | Asp | Asp | Asp | Ser | Asp | Cys | Asp | Pro | Val | Ser | Glu | Asn | Ser | Ile |
|   |   |   | 580 |   |   |   |   | 585 |   |   |   |   | 590 |   |   |
| Gly | Gly | Cys | Ala | Val | Arg | Gln | Gln | Leu | Val | Ile | Tyr | Thr | Ala | Gly | Thr |
|   |   | 595 |   |   |   |   | 600 |   |   |   |   | 605 |   |   |   |

| Leu | His | Ile | Val | Val | Val | Val | Ser | Ile | Val | Gly | Leu | Phe | Ser | Trp |
|---|---|---|---|---|---|---|---|---|---|---|---|---|---|---|
| | 610 | | | | 615 | | | | | 620 | | | | |

| Leu | Tyr | Ser | Gly | Leu | Ser | Val | Phe | Ala | Lys | Phe | His | Ser | Asp | Ser | Gln |
|---|---|---|---|---|---|---|---|---|---|---|---|---|---|---|---|
| 625 | | | | | 630 | | | | | 635 | | | | | 640 |

| Tyr | Pro | Glu | Ala | Pro | Phe | Ile | Glu | Gln | His | Asn | His | Leu | Glu | Arg | Leu |
|---|---|---|---|---|---|---|---|---|---|---|---|---|---|---|---|
| | | | | 645 | | | | | 650 | | | | | 655 | |

| Ser | Ala | Asn | Gln | Thr | Gly | Tyr | Leu | Thr | Pro | Arg | Ala | Asn | Lys | Ala | Val |
|---|---|---|---|---|---|---|---|---|---|---|---|---|---|---|---|
| | | | 660 | | | | | 665 | | | | | 670 | | |

| Asn | Leu | Val | Val | Lys | Val | Ser | Ser | Ser | Thr | Pro | Arg | Pro | Lys | Lys | Asp |
|---|---|---|---|---|---|---|---|---|---|---|---|---|---|---|---|
| | | 675 | | | | | 680 | | | | | 685 | | | |

| Asn | Leu | Asp | Val | Ser | Lys | Asp | Leu | Asn | Ile | Ala | Ser | Asp | Gly | Thr | Leu |
|---|---|---|---|---|---|---|---|---|---|---|---|---|---|---|---|
| | 690 | | | | | 695 | | | | | 700 | | | | |

| Gln | Lys | Ile | Lys | Lys | Thr | Tyr | Ile |
|---|---|---|---|---|---|---|---|
| 705 | | | | | 710 | | |

(2) INFORMATION FOR SEQ ID NO:65:

(i) SEQUENCE CHARACTERISTICS:
        (A) LENGTH: 369 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..369

(xi) SEQUENCE DESCRIPTION: SEQ ID NO:65:

| ATG | ATT | TAT | TTA | TAC | ACG | GCG | GAT | AAC | GTA | ATT | CCA | AAA | GAT | GGT | TTA | 48 |
|---|---|---|---|---|---|---|---|---|---|---|---|---|---|---|---|---|
| Met | Ile | Tyr | Leu | Tyr | Thr | Ala | Asp | Asn | Val | Ile | Pro | Lys | Asp | Gly | Leu | |
| 1 | | | | 5 | | | | | 10 | | | | | 15 | | |

| CAA | GGA | GCA | TTT | GTC | GAT | AAA | GAC | GGT | ACT | TAT | GAC | AAA | GTT | TAC | ATT | 96 |
|---|---|---|---|---|---|---|---|---|---|---|---|---|---|---|---|---|
| Gln | Gly | Ala | Phe | Val | Asp | Lys | Asp | Gly | Thr | Tyr | Asp | Lys | Val | Tyr | Ile | |
| | | | 20 | | | | | 25 | | | | | 30 | | | |

| CTT | TTC | ACT | GTT | ACT | ATC | GGC | TCA | AAG | AGA | ATT | GTT | AAA | ATT | CCG | TAT | 144 |
|---|---|---|---|---|---|---|---|---|---|---|---|---|---|---|---|---|
| Leu | Phe | Thr | Val | Thr | Ile | Gly | Ser | Lys | Arg | Ile | Val | Lys | Ile | Pro | Tyr | |
| | | 35 | | | | | 40 | | | | | 45 | | | | |

| ATA | GCA | CAA | ATG | TGC | TTA | AAC | GAC | GAA | TGT | GGT | CCA | TCA | TCA | TTG | TCT | 192 |
|---|---|---|---|---|---|---|---|---|---|---|---|---|---|---|---|---|
| Ile | Ala | Gln | Met | Cys | Leu | Asn | Asp | Glu | Cys | Gly | Pro | Ser | Ser | Leu | Ser | |
| | 50 | | | | | 55 | | | | | 60 | | | | | |

| AGT | CAT | AGA | TGG | TCG | ACG | TTG | CTC | AAA | GTC | GAA | TTA | GAA | TGT | GAC | ATC | 240 |
|---|---|---|---|---|---|---|---|---|---|---|---|---|---|---|---|---|
| Ser | His | Arg | Trp | Ser | Thr | Leu | Leu | Lys | Val | Glu | Leu | Glu | Cys | Asp | Ile | |
| 65 | | | | | 70 | | | | | 75 | | | | | 80 | |

| GAC | GGA | AGA | AGT | TAT | AGT | CAA | ATT | AAT | CAT | TCT | AAA | ACT | ATA | AAA | CAG | 288 |
|---|---|---|---|---|---|---|---|---|---|---|---|---|---|---|---|---|
| Asp | Gly | Arg | Ser | Tyr | Ser | Gln | Ile | Asn | His | Ser | Lys | Thr | Ile | Lys | Gln | |
| | | | | 85 | | | | | 90 | | | | | 95 | | |

| ATA | ATG | ATA | CGA | TAC | TAT | ATG | TAT | TCT | TTG | ATA | GTC | CTT | TTC | CAA | GTC | 336 |
|---|---|---|---|---|---|---|---|---|---|---|---|---|---|---|---|---|
| Ile | Met | Ile | Arg | Tyr | Tyr | Met | Tyr | Ser | Leu | Ile | Val | Leu | Phe | Gln | Val | |
| | | | 100 | | | | | 105 | | | | | 110 | | | |

| CGC | ATT | ATG | TAC | CTA | TTC | TAT | GAA | TAC | CAT | TAA | | | | | | 369 |
|---|---|---|---|---|---|---|---|---|---|---|---|---|---|---|---|---|
| Arg | Ile | Met | Tyr | Leu | Phe | Tyr | Glu | Tyr | His | | | | | | | |
| | | 115 | | | | | 120 | | | | | | | | | |

(2) INFORMATION FOR SEQ ID NO:66:

(i) SEQUENCE CHARACTERISTICS:
        (A) LENGTH: 122 amino acids
        (B) TYPE: amino acid
        (D) TOPOLOGY: linear (ii) MOLECULE TYPE: protein (x i) SEQUENCE DESCRIPTION: SEQ ID NO:66:

| Met | Ile | Tyr | Leu | Tyr | Thr | Ala | Asp | Asn | Val | Ile | Pro | Lys | Asp | Gly | Leu |
| 1 | | | | 5 | | | | | 10 | | | | | 15 | |

| Gln | Gly | Ala | Phe | Val | Asp | Lys | Asp | Gly | Thr | Tyr | Asp | Lys | Val | Tyr | Ile |
| | | | 20 | | | | | 25 | | | | | 30 | | |

| Leu | Phe | Thr | Val | Thr | Ile | Gly | Ser | Lys | Arg | Ile | Val | Lys | Ile | Pro | Tyr |
| | | 35 | | | | | 40 | | | | | 45 | | | |

| Ile | Ala | Gln | Met | Cys | Leu | Asn | Asp | Glu | Cys | Gly | Pro | Ser | Ser | Leu | Ser |
| | 50 | | | | | 55 | | | | | 60 | | | | |

| Ser | His | Arg | Trp | Ser | Thr | Leu | Leu | Lys | Val | Glu | Leu | Glu | Cys | Asp | Ile |
| 65 | | | | | 70 | | | | | 75 | | | | | 80 |

| Asp | Gly | Arg | Ser | Tyr | Ser | Gln | Ile | Asn | His | Ser | Lys | Thr | Ile | Lys | Gln |
| | | | | 85 | | | | | 90 | | | | | 95 | |

| Ile | Met | Ile | Arg | Tyr | Tyr | Met | Tyr | Ser | Leu | Ile | Val | Leu | Phe | Gln | Val |
| | | | 100 | | | | | 105 | | | | | 110 | | |

| Arg | Ile | Met | Tyr | Leu | Phe | Tyr | Glu | Tyr | His |
| | | 115 | | | | | 120 | | |

(2) INFORMATION FOR SEQ ID NO:67:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:67:

| Asp | Cys | Gln | Asn | Tyr | Ile |
| 1 | | | | 5 | |

(2) INFORMATION FOR SEQ ID NO:68:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..8
        (D) OTHER INFORMATION: /label=SEQ68
            / note= "Xaa denotes N or G at residue #4; and A or S at residue #5"

(x i) SEQUENCE DESCRIPTION: SEQ ID NO:68:

| Cys | Gly | Thr | Xaa | Xaa | Xaa | Xaa | Pro |
| 1 | | | | 5 | | | |

(2) INFORMATION FOR SEQ ID NO:69:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..7
        (D) OTHER INFORMATION: /label=SEQ69

/ note= "Xaa denotes S or C at residue #3"

( x i ) SEQUENCE DESCRIPTION: SEQ ID NO:69:

Gly Xaa Xaa Pro Tyr Asp Pro
1               5

( 2 ) INFORMATION FOR SEQ ID NO:70:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..7
    ( D ) OTHER INFORMATION: /label=SEQ70
         / note= "Xaa denotes V, N or A"

( x i ) SEQUENCE DESCRIPTION: SEQ ID NO:70:

Leu Tyr Ser Gly Thr Xaa Ala
1               5

( 2 ) INFORMATION FOR SEQ ID NO:71:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:71:

Leu Asn Ala Pro Asn Phe Val
1               5

( 2 ) INFORMATION FOR SEQ ID NO:72:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..7
    ( D ) OTHER INFORMATION: /label=SEQ72
         / note= "Xaa denotes V or I"

( x i ) SEQUENCE DESCRIPTION: SEQ ID NO:72:

Arg Xaa Ala Arg Val Cys Lys ( 2 ) INFORMATION FOR SEQ ID NO:73:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9

(D) OTHER INFORMATION: /label=SEQ73
/ note= "Xaa denotes T or A at residue #2; T or S at residue #3; F or Y at residue #4; and A or S at residue #7"

(xi) SEQUENCE DESCRIPTION: SEQ ID NO:73:

Trp Xaa Xaa Xaa Leu Lys Xaa Arg Leu
1               5

(2) INFORMATION FOR SEQ ID NO:74:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION: 1..9
      (D) OTHER INFORMATION: /label=SEQ74
         / note= "Xaa denotes N or D"

(xi) SEQUENCE DESCRIPTION: SEQ ID NO:74:

Pro Phe Tyr Phe Xaa Glu Ile Gln Ser
1               5

(2) INFORMATION FOR SEQ ID NO:75:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION: 1..7
      (D) OTHER INFORMATION: /label=SEQ75
         / note= "Xaa denotes F or Y at residue #7"

(xi) SEQUENCE DESCRIPTION: SEQ ID NO:75:

Gly Ser Ala Val Cys Xaa Xaa
1               5

(2) INFORMATION FOR SEQ ID NO:76:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION: 1..7
      (D) OTHER INFORMATION: /label=SEQ76
         / note= "Xaa denotes P or A at residue #6"

(xi) SEQUENCE DESCRIPTION: SEQ ID NO:76:

Asn Ser Asn Trp Leu Xaa Val
1               5

(2) INFORMATION FOR SEQ ID NO:77:

(i) SEQUENCE CHARACTERISTICS:

(A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label=SEQ77
            / note= "Xaa denotes E or D at residue #2; T, Q or S
              at residue #7"

(xi) SEQUENCE DESCRIPTION: SEQ ID NO:77:

Pro Xaa Pro Arg Pro Gly Xaa Cys
1                   5

(2) INFORMATION FOR SEQ ID NO:78:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label=SEQ78
            / note= "Xaa denotes A or G"

(xi) SEQUENCE DESCRIPTION: SEQ ID NO:78:

Asp Pro Tyr Cys Xaa Trp Asp
1                   5

(2) INFORMATION FOR SEQ ID NO:79:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label=SEQ79
            / note= "Xaa denotes N or G at residue #4; A or S at
              residue #5; Y, F, H or G at residue #6; and K, R, H, N or
              Q at residue #7"

(xi) SEQUENCE DESCRIPTION: SEQ ID NO:79:

Cys Gly Thr Xaa Xaa Xaa Xaa
1                   5

(2) INFORMATION FOR SEQ ID NO:80:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label=SEQ80

/ note= "Xaa denotes N or G at residue #4; A, S or N
at residue #5; Y, F or H at residue #6; and K, R, ( 2 ) INFORMATION FOR SEQ ID NO:84:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ84
            / note= "Xaa denotes V or I at residue #1; F or Y
            at residue #2; F, Y, I or L at residue #3; F, Y or I at
            residue #4; R or T at residue #6; and T or N at residue
            # 8"

( x i ) SEQUENCE DESCRIPTION: SEQ ID NO:84:

Xaa Xaa Xaa Xaa Phe Xaa Xaa Xaa
1                 5

( 2 ) INFORMATION FOR SEQ ID NO:85:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ85
            / note= "Xaa denotes V or I at residue #1; F or Y
            at residue #2; F, Y, I or L at residue #3; F, Y, I or L
            at residue #4; and T or N at residue #8"

( x i ) SEQUENCE DESCRIPTION: SEQ ID NO:85:

Xaa Xaa Xaa Xaa Phe Arg Xaa Xaa
1                 5

( 2 ) INFORMATION FOR SEQ ID NO:86:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ86
            / note= "Xaa denotes V or I at residue #1; F or Y
            at residue #2; F, Y or L at residue #3; F, Y, I or L at
            residue #4; F or Y at residue #5, R or T at residue #6,
            E, D or V at residue #7; and T or N at residue #8"

( x i ) SEQUENCE DESCRIPTION: SEQ ID NO:86:

Xaa Xaa Xaa Xaa Xaa Xaa Xaa Xaa
1                 5

( 2 ) INFORMATION FOR SEQ ID NO:87:

( i ) SEQUENCE CHARACTERISTICS:
        ( A ) LENGTH: 7 amino acids (B) TYPE: amino acid
(C) STRANDEDNESS: single
(D) TOPOLOGY: linear (ii) MOLECULE TYPE: peptide (ix) FEATURE:
    (A) NAME/KEY: Peptide
    (B) LOCATION: 1..7
    (D) OTHER INFORMATION: /label=SEQ87
        / note= "Xaa denotes R, K or N at residue #1; T or A at residue #3; T, A or S at residue #4; F, Y or L at residue #5; and K or R at residue #7"

(xi) SEQUENCE DESCRIPTION: SEQ ID NO:87:

Xaa  Trp  Xaa  Xaa  Xaa  Leu  Xaa
1                    5

(2) INFORMATION FOR SEQ ID NO:88:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..9
    (D) OTHER INFORMATION: /label=SEQ88
        / note= "Xaa denotes T or A at residue #2; T, A or S at residue #3; F, Y or L at residue #4; A, S, V, I or L at residue #7"

(xi) SEQUENCE DESCRIPTION: SEQ ID NO:88:

Trp  Xaa  Xaa  Xaa  Leu  Lys  Xaa  Xaa  Leu
1                    5

(2) INFORMATION FOR SEQ ID NO:89:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1..9
    (D) OTHER INFORMATION: /label=SEQ89
        / note= "Xaa denotes T, A or S at residue #2; T, A or S at residue #3; F, Y or L at residue #4; A, S, I or L at residue #7"

(xi) SEQUENCE DESCRIPTION: SEQ ID NO:89:

Trp  Xaa  Xaa  Xaa  Leu  Lys  Xaa  Xaa  Leu
1                    5

(2) INFORMATION FOR SEQ ID NO:90:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide ( B ) LOCATION: 1..11
            ( D ) OTHER INFORMATION: /label=SEQ90
                    / note= "Xaa denotes T or A at residue #2; and T, A or S
                    at residue #3"

( x i ) SEQUENCE DESCRIPTION: SEQ ID NO:90:

Trp  Xaa  Xaa  Xaa  Leu  Lys  Xaa  Xaa  Leu  Xaa  Cys
    1                    5                        10

( 2 ) INFORMATION FOR SEQ ID NO:91:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..9
                ( D ) OTHER INFORMATION: /label=SEQ91
                        / note= "Xaa denotes V, L or I at residue #1"

( x i ) SEQUENCE DESCRIPTION: SEQ ID NO:91:

Xaa  Pro  Xaa  Pro  Arg  Pro  Gly  Xaa  Cys
    1                    5

( 2 ) INFORMATION FOR SEQ ID NO:92:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..7
                ( D ) OTHER INFORMATION: /label=SEQ92
                        / note= "Xaa denotes K or Y at residue #2; F or Y
                        at residue #4; F, Y or L at residue #5; F, Y, I or L at
                        residue #6; and F or Y at residue #7"

( x i ) SEQUENCE DESCRIPTION: SEQ ID NO:92:

Asp  Xaa  Val  Xaa  Xaa  Xaa  Xaa
    1                    5

( 2 ) INFORMATION FOR SEQ ID NO:93:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 1..7
                ( D ) OTHER INFORMATION: /label=SEQ93
                        / note= "Xaa denotes K or Y at residue #2; F or Y
                        at residue #4; F, Y, I or L at residue #5; F, Y or I at
                        residue #6; and F or Y at residue #7"

( x i ) SEQUENCE DESCRIPTION: SEQ ID NO:93:

Asp  Xaa  Val  Xaa  Xaa  Xaa  Xaa
    1                    5

( 2 ) INFORMATION FOR SEQ ID NO:94:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ94
            / note= "Xaa denotes V or I at residue #1; F, Y or L
            at residue #3; F, Y, I or L at residue #4; R or T at
            residue #6; and T or N at residue #8"

( x i ) SEQUENCE DESCRIPTION: SEQ ID NO:94:

Xaa  Tyr  Xaa  Xaa  Phe  Xaa  Xaa  Xaa
    1                              5

( 2 ) INFORMATION FOR SEQ ID NO:95:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ95
            / note= "Xaa denotes V or I at residue #1; F, Y, I or L
            at residue #3; F, Y or I at residue #4; R or T at
            residue #6; and T or N at residue #8"

( x i ) SEQUENCE DESCRIPTION: SEQ ID NO:95:

Xaa  Tyr  Xaa  Xaa  Phe  Xaa  Xaa  Xaa
    1                              5

( 2 ) INFORMATION FOR SEQ ID NO:96:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=SEQ96
            / note= "Xaa denotes V or I at residue #1; F, Y, I or L
            at residue #3; F, Y, I or L at residue #4; and T or N at
            residue #8"

( x i ) SEQUENCE DESCRIPTION: SEQ ID NO:96:

Xaa  Tyr  Xaa  Xaa  Phe  Arg  Xaa  Xaa
    1                              5

( 2 ) INFORMATION FOR SEQ ID NO:97:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /label=SEQ97
        / note= "Xaa denotes F or Y at residue #2; F, Y or L
        at residue #3; F, Y, I or L at residue #4; F or Y at
        residue #5; R or T at residue #6; E, D, or V at residue
        # 7; and T or N at residue #8"

( x i ) SEQUENCE DESCRIPTION: SEQ ID NO:97:

Val Xaa Xaa Xaa Xaa Xaa Xaa Xaa
1                      5

( 2 ) INFORMATION FOR SEQ ID NO:98:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /label=SEQ98
        / note= "Xaa denotes F or Y at residue #2; F, Y, I or L
        at residue #3; F, Y or I at residue #4; F or Y at
        residue #5; R or T at residue #6; E, D, or V at residue
        # 7; and T or N at residue #8"

( x i ) SEQUENCE DESCRIPTION: SEQ ID NO:98:

Val Xaa Xaa Xaa Xaa Xaa Xaa Xaa
1                      5

( 2 ) INFORMATION FOR SEQ ID NO:99:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /label=SEQ99
        / note= "Xaa denotes F or Y at residue #2; F, Y, I or L
        at residue #3; F, Y, I or L at residue #4; F or Y at
        residue #5; E, D, or V at residue #7; and T or N at
        residue #8"

( x i ) SEQUENCE DESCRIPTION: SEQ ID NO:99:

Val Xaa Xaa Xaa Xaa Arg Xaa Xaa
1                      5

( 2 ) INFORMATION FOR SEQ ID NO:100:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide 5,807,826

135

-continued (B) LOCATION: 1..8
(D) OTHER INFORMATION: /label=SEQ100
/ note= "Xaa denotes F or Y at residue #2; F, Y, I or L
at residue #3; F, Y, I or L at residue #4; F or Y at
residue #5; R or T at residue #6; E, D, or V at residue
7; and T or N at residue #8"

(xi) SEQUENCE DESCRIPTION: SEQ ID NO:100:

Val Xaa Xaa Xaa Xaa Xaa Xaa Xaa
1               5

SEMAPHORIN GENE FAMILY

This is a division of application Ser. No. 08/121,713 filed Sep. 13, 1993 now U.S. Pat. No. 5,639,856.

The research carried out in the subject application was supported in part by grants from the National Institutes of Health. The government may have rights in any patent issuing on this application.

INTRODUCTION

1. Technical Field

The technical field of this invention concerns peptides, polypeptides, and polynucleotides involved in nerve cell growth.

2. Background

The specificity of the wiring of the nervous system—the complex pattern of specific synaptic connections—begins to unfold during development as the growing tips of neurons—the growth cones—traverse long distances to find their correct targets. Along their journey, they are confronted by and correctly navigate a series of choice points in a remarkably unerring way to ultimately contact and recognize their correct target.

The identification of growth cone guidance cues is to a large extent, the holy grail of neurobiology. These are the compounds that tell neurons when to grow, where to grow, and when to stop growing. The medical applications of such compounds and their antagonists are enormous and include modulating neuronal growth regenerative capacity, treating neurodegenerative disease, and mapping (e.g. diagnosing) genetic neurological defects.

Over decades of concentrated research, various hypotheses of chemo-attractants and repellant, labeled pathways, cell adhesion molecules, etc. have been evoked to explain guidance. Recently, several recent lines of experiments suggest repulsion may play an important role in neuron guidance and two apparently unrelated factors ("Neurite Growth Inhibitor" and "Collapsin") capable of inhibiting or collapsing growth cones have been reported.

3. Relevant Literature

For a recent review of much of the literature in this field, see Goodman and Shatz (1993) Cell 72/Neuron 10, 77–98. A description of grasshopper fasciclin IV (now called G-Semaphorin I) appears in Kolodkin et al. (1992) Neuron 9, 831–845. Recent reports on Collapsin and Neurite Growth Inhibitor include Raper and Kapfhammer (1990) Neuron 4, 21–29, an abstract presented by Raper at the GIBCO-BRL Symposium on "Genes and Development/Function of Brain" on Jul. 26, 1993 and Schwab and Caroni (1988) J Neurosci 8, 2381 and Schnell and Schwab (1990) Nature 343, 269, respectively.

SUMMARY OF THE INVENTION

A novel class of proteins, semaphorins, nucleic acids encoding semaphorins, and methods of using semaphorins and semaphorin-encoding nucleic acids are disclosed. Semaphorins include the first known family of human proteins which function as growth cone inhibitors and a family of proteins involved in viral, particularly pox viral, pathogenesis and oncogenesis. Families of semaphorin-specific receptors, including receptors found on nerve growth cones and immune cells are also disclosed.

The invention provides agents, including semaphorin peptides, which specifically bind semaphorin receptors and agents, including semaphorin receptor peptides, which specifically bind semaphorins. These agents provide potent modulators of nerve cell growth, immune responsiveness and viral pathogenesis and find use in the treatment and diagnosis of neurological disease and neuro-regeneration, immune modulation including hypersensitivity and graft-rejection, and diagnosis and treatment of viral and oncological infection/diseases.

Semaphorins, semaphorin receptors, semaphorin-encoding nucleic acids, and unique portions thereof also find use variously in screening chemical libraries for regulators of semaphorin or semaphorin receptor-mediated cell activity, in genetic mapping, as probes for related genes, as diagnostic reagents for genetic neurological, immunological and oncological disease and in the production of specific cellular and animal systems for the development of neurological, immunological, oncological and viral disease therapy.

DESCRIPTION OF SPECIFIC EMBODIMENTS

The present invention discloses novel families of proteins important in nerve and immune cell function: the semaphorins and the semaphorin receptors. The invention provides agents, including semaphorin peptides, which specifically bind semaphorin receptors and agents, including semaphorin receptor peptides, which specifically bind semaphorins. These agents find a wide variety of clinical, therapeutic and research uses, especially agents which modulate nerve and/or immune cell function by specifically mimicing or interfering with semaphorin-receptor binding. For example, selected semaphorin peptides shown to act as semaphorin receptor antagonists are effective by competitively inhibiting native semaphorin association with cellular receptors. Thus, depending on the targeted receptor, these agents can be used to block semaphorin mediated neural cell growth cone repulsion or contact inhibition. Such agents find broad clinical application where nerve cell growth is indicated, e.g. traumatic injury to nerve cells, neurodegenerative disease, etc. A wide variety of semaphorin- and semaphorin receptor-specific binding agents and methods for identifying, making and using the same are described below.

Binding agents of particular interest are semaphorin peptides which specifically bind and antagonize a semaphorin receptor and semaphorin receptor peptides which specifically bind a semaphorin and prevent binding to a native receptor. While exemplified primarily with semaphorin peptides, much of the following description applies analogously to semaphorin receptor peptides.

The semaphorin peptides of the invention comprise a unique portion of a semaphorin and have semaphorin binding specificity. A "unique portion" of a semaphorin has an amino acid sequence unique to that disclosed in that it is not found in any previously known protein. Thus a unique portion has an amino acid sequence length at least long enough to define a novel peptide. Unique semaphorin portions are found to vary from about 5 to about 25 residues, preferably from 5 to 10 residues in length, depending on the particular amino acid sequence. Unique semaphorin portions are readily identified by comparing the subject semaphorin portion sequences with known peptide/protein sequence data bases. Preferred unique portions derive from the semaphorin domains (which exclude the Ig-like, intracellular and transmembrane domains as well as the signal sequences) of the disclosed semaphorin sequences, especially regions that bind the semaphorin receptor, especially that of the human varieties. Preferred semaphorin receptor unique portions derive from the semaphorin binding domains, especially regions with residues which contact the semaphorin ligand, especially that of the human varieties. Particular preferred peptides are further described herein.

The subject peptides may be free or coupled to other atoms or molecules. Frequently the peptides are present as a portion of a larger polypeptide comprising the subject peptide where the remainder of the polypeptide need not be semaphorin- or semaphorin receptor-derived. Alternatively, the subject peptide may be present as a portion of a "substantially full-length" semaphorin domain or semaphorin receptor sequence which comprises or encodes at least about 200, preferably at least about 250, more preferably at least about 300 amino acids of a disclosed semaphorin/receptor sequence. Thus the invention also provides polypeptides comprising a sequence substantially similar to that of a substantially full-length semaphorin domain or a semaphorin receptor. "Substantially similar" sequences share at least about 40%, more preferably at least about 60%, and most preferably at least about 80% sequence identity. Where the sequences diverge, the differences are generally point insertions/deletions or conservative substitutions, i.e. a cysteine/threonine or serine substitution, an acidic/acidic or hydrophobic/hydrophobic amino acid substitution, etc.

The subject semaphorin peptides/polypeptides are "isolated", meaning unaccompanied by at least some of the material with which they are associated in their natural state. Generally, an isolated peptide/polypeptide constitutes at least about 1%, preferably at least about 10%, and more preferably at least about 50% by weight of the total peptide/protein in a given sample. By pure peptide/polypeptide is intended at least about 90%, preferably at least 95%, and more preferably at least about 99% by weight of total peptide/protein. Included in the subject peptide/polypeptide weight are any atoms, molecules, groups, or polymers covalently coupled to the subject semaphorin/receptor peptide/polypeptide, especially peptides, proteins, detectable labels, glycosylations, phosphorylations, etc.

The subject peptides/polypeptides may be isolated or purified in a variety of ways known to those skilled in the art depending on what other components are present in the sample and to what, if anything, the peptide/polypeptide is covalently linked. Purification methods include electrophoretic, molecular, immunological and chromatographic techniques, especially affinity chromatography and RP-HPLC in the case peptides. For general guidance in suitable purification techniques, see Scopes, R., Protein Purification, Springer-Verlag, NY (1982).

The subject peptides/polypeptides generally comprise naturally occurring amino acids but D-amino acids or amino acid mimetics coupled by peptide bonds or peptide bond mimetics may also be used. Amino acid mimetics are other than naturally occurring amino acids that conformationally mimic the amino acid for the purpose of the requisite semaphorin/receptor binding specificity. Suitable mimetics are known to those of ordinary skill in the art and include β-γ-δ amino and imino acids, cyclohexylalanine, adamantylacetic acid, etc., modifications of the amide nitrogen, the α-carbon, amide carbonyl, backbone modifications, etc. See, generally, Morgan and Gainor (1989) Ann. Repts. Med. Chem 24, 243–252; Spatola (1983) Chemistry and Biochemistry of Amino Acids, Peptides and Proteins, Vol VII (Weinstein) and Cho et. al (1993) Science 261, 1303–1305 for the synthesis and screening of oligocarbamates.

The subject semaphorin peptides/polypeptides have a "semaphorin binding specificity" meaning that the subject peptide/polypeptide retains a molecular conformation specific to one or more of the disclosed semaphorins and specifically recognizable by a semaphorin-specific receptor, antibody, etc. As such, a semaphorin binding specificity may be provided by a semaphorin-specific immunological epitope, lectin binding site, etc., and preferably, a receptor binding site. Analogously, the semaphorin receptor peptides/polypeptides have a "semaphorin receptor binding specificity" meaning that these peptides/polypeptides retain a molecular conformation specific to one or more of the disclosed semaphorin receptors and specifically recognizable by a semaphorin, a receptor-specific antibody, etc.

"Specific binding" is empirically determined by contacting, for example a semaphorin-derived peptide with a mixture of components and identifying those components that preferentially bind the semaphorin. Specific binding is most conveniently shown by competition with labeled ligand using recombinant semaphorin peptide either in vitro or in cellular expression systems as disclosed herein. Generally, specific binding of the subject semaphorin has binding affinity of $10^{-6}$M, preferably $10^{-8}$M, more preferably $10^{-10}$M, under in vitro conditions as exemplified below.

The peptides/polypeptides may be modified or joined to other compounds using physical, chemical, and molecular techniques disclosed or cited herein or otherwise known to those skilled in the relevant art to affect their semaphorin binding specificity or other properties such as solubility, membrane transportability, stability, binding specificity and affinity, chemical reactivity, toxicity, bioavailability, localization, detectability, in vivo half-life, etc. as assayed by methods disclosed herein or otherwise known to those of ordinary skill in the art. For example, point mutations are introduced by site directed mutagenesis of nucleotides in the DNA encoding the disclosed semaphorin polypeptides or in the course of in vitro peptide synthesis.

Other modifications to further modulate binding specificity/affinity include chemical/enzymatic intervention (e.g. fatty acid-acylation, proteolysis, glycosylation) and especially where the peptide/polypeptide is integrated into a larger polypeptide, selection of a particular expression host, etc. In particular, many of the disclosed semaphorin peptides contain serine and threonine residues which are phosphorylated or dephosphorylated. See e.g. methods disclosed in Roberts et al. (1991) Science 253, 1022–1026 and in Wegner et al. (1992) Science 256, 370–373. Amino and/or carboxyl termini may be functionalized e.g., for the amino group, acylation or alkylation, and for the carboxyl group, esterification or amidification, or the like. Many of the disclosed semaphorin peptides/polypeptides also contain glycosylation sites and patterns which may disrupted or modified, e.g. by enzymes like glycosidases or used to purify/identify the receptor, e.g. with lectins. For instance, N or O-linked glycosylation sites of the disclosed semaphorin peptides may be deleted or substituted for by another basic amino acid such as Lys or His for N-linked glycosylation alterations, or deletions or polar substitutions are introduced at Ser and Thr residues for modulating O-linked glycosylation. Glycosylation variants are also produced by selecting appropriate host cells, e.g. yeast, insect, or various mammalian cells, or by in vitro methods such as neuraminidase digestion. Useful expression systems include COS-7, 293, BHK, CHO, TM4, CV1, VERO-76, HELA, MDCK, BRL 3A, W138, Hep G2, MMT 060562, TRI cells, baculovirus systems, for examples. Other covalent modifications of the disclosed semaphorin peptides/polypeptides may be introduced by reacting the targeted amino acid residues with an organic derivatizing (e.g. methyl-3-[(p-azido-phenyl)dithio]propioimidate) or crosslinking agent (e.g. 1,1-bis (diazoacetyl)-2-phenylethane) capable of reacting with selected side chains or termini. For therapeutic and diagnostic localization, semaphorins and peptides thereof may be labeled directly (radioisotopes, fluorescers, etc.) or indirectly with an agent capable of providing a detectable signal, for example, a heart muscle kinase labeling site.

The following are 14 classes of preferred semaphorin peptides where bracketed positions may be occupied by any one of the residues contained in the brackets and "Xaa" signifies that the position may be occupied by any one of the 20 naturally encoded amino acids (see, Table 1). These enumerated peptides maintain highly conserved structures which provide important semaphorin binding specificities;

(a) [AspGlu]Cys[GlnLysArgAlaAsn]Asn[TyrPheVal]Ile (SEQ ID NO:1)
Cys[GlnLysArgAlaAsn]Asn[TyrPheVal]Ile[ArgLysGlnThr] (SEQ ID NO:2)

(b) CysGlyThr[AsnGly][AlaSerAsn][TyrPheHisGly][LysArgHisAsnGln] (SEQ ID NO:3)
CysGlyThr[AsnGly][AlaSerAsn]XaaXaaPro (SEQ ID NO:4)
CysGlyThr[AsnGly]XaaXaaXaaProXaa[CysAsp] (SEQ ID NO:5)
CysGlyThrXaaXaaXaaXaaProXaa[CysAsp]XaaXaa[TyrIle] (SEQ ID NO:6)

(c) [ArgIleGlnVal][GlyAla][LeuValLys][CysSer]Pro[PheTyr][AspAsn] (SEQ ID NO:7)
[CysSer]Pro[PheTyr][AspAsn]Pro[AspGluArgLys][HisLeuAsp] (SEQ ID NO:8)
GlyXaa[GlyAla]Xaa[CysSer]ProTyr[AspAsn]Pro (SEQ ID NO:9)

(d) Leu[PheTyr]Ser[GlyAla]Thr[ValAsnAla]Ala (SEQ ID NO:10)
Leu[PheTyr]SerXaaThrXaaAla[AspGlu][PheTyr] (SEQ ID NO:11)
[PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14)
PhePhe[PheTyr]ArgGlu[ThrAsn] (SEQ ID NO:15)
PhePheArgGlu[ThrAsn]Ala (SEQ ID NO:16)
Phe[PheTyr]ArgGlu[ThrAsn]Ala (SEQ ID NO:17)
TyrPhePhe[PheTyr]ArgGlu (SEQ ID NO:18)
[PheTyr]PhePhe[PheTyr]ArgGlu (SEQ ID NO:19)
[PheTyr][PheTyr][PheTyr]ArgGlu[ThrAsn]Ala (SEQ ID NO:20)
[IleVal][PheTyr]Phe[PheTyr][PheTyr]ArgGlu (SEQ ID NO:21)
Asp[LysPheTyr]Val[PheTyr][PheTyrIleLeu][PheTyrIleLeu][PheTyr] (SEQ ID NO:22)
[ValIle][PheTyr][PheTyrIleLeu][PheTyrIleLeu]Phe[ArgThr]Xaa[ThrAsn] (SEQ ID NO:23)
[ValIle][PheTyr][PheTyrIleLeu][PheTyrIleLeu][PheTyr][ArgThr][GluAspVal][ThrAsn] (SEQ ID NO:24)

(g) Glu[PheTyr]IleAsn[CysSer]GlyLys (SEQ ID NO:25)
[PheTyr]IleAsnCysGlyLys[AlaValIle] (SEQ ID NO:26)

(h) Arg[ValIle][AlaGly][ArgGln][ValIle]CysLys (SEQ ID NO:27)
Arg[ValIle]Xaa[ArgGln][ValIle]CysXaaXaaAsp (SEQ ID NO:28)
GlyLys[ValAlaIle]XaaXaaXaaArg[ValAlaIle]XaaXaaXaaCysLys (SEQ ID NO:29)

(i) [ArgLysAsn]Trp[ThrAlaSer][ThrAlaSer][PheTyrLeu]Leu[LysArg] (SEQ ID NO:30)

[PheTyr]Leu[LysArg][AlaSer]ArgLeu[AsnIle]Cys (SEQ ID NO:31)
[AsnIle]CysSer[IleVal][ProSer]Gly (SEQ ID NO:32)
Trp[ThrAlaSer][ThrAlaSer][PheTyrLeu]LeuLys[AlaSerValIleLeu]XaaLeu (SEQ ID NO:33)
Trp[ThrAlaSer][ThrAlaSer]XaaLeuLysXaaXaaLeuXaaCys (SEQ ID NO:34)
TrpXaa[ThrSer]XaaLeuLysXaaXaaLeuXaaCys (SEQ ID NO:35)

(j) [PheTyr][PheTyr][AsnAsp]GluIleGlnSer (SEQ ID NO:36)
[PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38)
SerAla[ValIleLeu]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41)
[ValLeuIle]ProXaaPro[ArgAla]ProGlyXaaCys (SEQ ID NO:42)
Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44)
Pro[HisPheTyr]Cys[AlaGly]TrpAsp (SEQ ID NO:45)
AspProXaaCys[AlaGly]TrpAsp (SEQ ID NO:46)
CysXaaXaaXaaXaaAspProXaaCysXaaTrpAsp (SEQ ID NO:47)
CysXaaXaaXaaAspProXaaCysXaaTrpAsp (SEQ ID NO:48)
CysXaaXaaAspProXaaCysXaaTrpAsp (SEQ ID NO:49)
CysXaaXaaCysXaaXaaXaaXaaAspXaaXaaCysXaaTrpAsp (SEQ ID NO:50)
CysXaaXaaCysXaaXaaXaaAspXaaXaaCysXaaTrpAsp (SEQ ID NO:51)
CysXaaXaaCysXaaXaaAspXaaXaaCysXaaTrpAsp (SEQ ID NO:52)

The following peptides represent particularly preferred members of each class:
(a) AspCysGlnAsnTyrIle (SEQ ID NO:67)
(b) CysGlyThr[AsnGly][AlaSer]XaaXaaPro (SEQ ID NO:68)
(c) GlyXaa[SerCys]ProTyrAspPro (SEQ ID NO:69)
(d) LeuTyrSerGlyThr[ValAsnAla]Ala (SEQ ID NO:70)
(e) LeuAsnAlaProAsnPheVal (SEQ ID NO:71)
(f) [PheTyr]PhePhe[PheTyr]ArgGlu (SEQ ID NO:19)
(g) Glu[PheTyr]IleAsn[CysSer]GlyLys (SEQ ID NO:25)
(h) Arg[ValIle]AlaArgValCysLys (SEQ ID NO:72)
(i) Trp[ThrAla][ThrSer][PheTyr]LeuLys[AlaSer]ArgLeu (SEQ ID NO:73)
(j) ProPheTyrPhe[AsnAsp]GluIleGlnSer (SEQ ID NO:74)
(k) GlySerAlaValCysXaa[PheTyr] (SEQ ID NO:75)
(l) AsnSerAsnTrpLeu[ProAla]Val (SEQ ID NO:76)
(m) Pro[GluAsp]ProArgProGly[ThrGlnSer]Cys (SEQ ID NO:77)
(n) AspProTyrCys[AlaGly]TrpAsp (SEQ ID NO:78)

The following 14 classes are preferred peptides which exclude semaphorin peptides encoded in open reading frames of Variola major or Vaccinia viruses.
(a) [AspGlu]Cys[GlnLysArgAlaAsn]Asn[TyrPheVal]Ile (SEQ ID NO:01)
Cys[GlnLysArgAlaAsn]Asn[TyrPheVal]Ile[ArgLysGlnThr] (SEQ ID NO:02)
(b) CysGlyThr[AsnGly][AlaSer][TyrPheHisGly][LysArgHisAsnGln] (SEQ ID NO:79)

CysGlyThr[AsnGly][AlaSerAsn][TyrPheHis][LysArgHisAsnGln] (SEQ ID NO:80)

CysGlyThr[AsnGly][AlaSer]XaaXaaPro (SEQ ID NO:81)

(c) [ArgIleGlnVal][GlyAla][LeuValLys][CysSer]Pro[PheTyr][AspAsn] (SEQ ID NO:07)

[CysSer]Pro[PheTyr][AspAsn]Pro[AspGluArgLys][HisLeuAsp] (SEQ ID NO:08)

GlyXaa[GlyAla]Xaa[CysSer]ProTyr[AspAsn]Pro (SEQ ID NO:09)

(d) Leu[PheTyr]Ser[GlyAla]Thr[ValAsnAla]Ala (SEQ ID NO:10)

Leu[PheTyr]SerXaaThrXaaAla[AspGlu][PheTyr] (SEQ ID NO:11)

[PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14)

PhePhe[PheTyr]ArgGlu[ThrAsn] (SEQ ID NO:15)

PhePheArgGlu[ThrAsn]Ala (SEQ ID NO:16)

Phe[PheTyr]ArgGlu[ThrAsn]Ala (SEQ ID NO:17)

TyrPhePhe[PheTyr]ArgGlu (SEQ ID NO:18)

[PheTyr]PhePhe[PheTyr]ArgGlu (SEQ ID NO:19)

[PheTyr][PheTyr][PheTyr]ArgGlu[ThrAsn]Ala (SEQ ID NO:20)

[IleVal][PheTyr]Phe[PheTyr][PheTyr]ArgGlu (SEQ ID NO:21)

Asp[LysPheTyr]Val[PheTyr][PheTyrLeu][PheTyrIleLeu][PheTyr] (SEQ ID NO:22)

Asp[LysPheTyr]Val[PheTyr][PheTyrIleLeu][PheTyrIle][PheTyr] (SEQ ID NO:82)

[ValIle][PheTyr][PheTyrLeu][PheTyrIleLeu]Phe[ArgThr]Xaa[ThrAsn] (SEQ ID NO:83)

[ValIle][PheTyr][PheTyrIleLeu][PheTyrIle]Phe[ArgThr]Xaa[ThrAsn] (SEQ ID NO:84)

[ValIle][PheTyr][PheTyrIleLeu][PheTyrIleLeu]PheArgXaa[ThrAsn] (SEQ ID NO:85)

[ValIle][PheTyr][PheTyrLeu][PheTyrIleLeu][PheTyr][ArgThr][GluAspVal][ThrAsn] (SEQ ID NO:86)

(g) Glu[PheTyr]IleAsn[CysSer]GlyLys (SEQ ID NO:25)

[PheTyr]IleAsnCysGlyLys[AlaValIle] (SEQ ID NO:26)

(h) Arg[ValIle][AlaGly][ArgGln][ValIle]CysLys (SEQ ID NO:27)

Arg[ValIle]Xaa[ArgGln][ValIle]CysXaaXaaAsp (SEQ ID NO:28)

GlyLys[ValAlaIle]XaaXaaXaaArg[ValAlaIle]XaaXaaXaaCysLys (SEQ ID NO:29)

(i) [ArgLysAsn]Trp[ThrAla][ThrAlaSer][PheTyrLeu]Leu[LysArg] (SEQ ID NO:87)

[PheTyr]Leu[LysArg][AlaSer]ArgLeu[AsnIle]Cys (SEQ ID NO:31)

[AsnIle]CysSer[IleVal][ProSer]Gly (SEQ ID NO:32)

Trp[ThrAla][ThrAlaSer][PheTyrLeu]LeuLys[AlaSerValIleLeu]XaaLeu (SEQ ID NO:88)

Trp[AlaSer][ThrAlaSer][PheTyrLeu]LeuLys[AlaSerIleLeu]XaaLeu (SEQ ID NO:89)

Trp[Ala][ThrAlaSer]XaaLeuLysXaaXaaLeuXaaCys (SEQ ID NO:90)

(j) [PheTyr][PheTyr][AsnAsp]GluIleGlnSer (SEQ ID NO:36)

[PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38)

SerAla[ValIle]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41)

[ValLeuIle]ProXaaProArgProGlyXaaCys (SEQ ID NO:91)

Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44)

Pro[HisPheTyr]Cys[AlaGly]TrpAsp (SEQ ID NO:45)

AspProXaaCys[AlaGly]TrpAsp (SEQ ID NO:46)

CysXaaXaaXaXaaAspProXaaCysXaaTrpAsp (SEQ ID NO:47)

CysXaaXaaXaaAspProXaaCysXaaTrpAsp (SEQ ID NO:48)

CysXaaXaaAspProXaaCysXaaTrpAsp (SEQ ID NO:49)

CysXaaXaaCysXaaXaaXaaXaaAspXaaXaaCysXaaTrpAsp (SEQ ID NO:50)

CysXaaXaaCysXaaXaaXaaAspXaaXaaCysXaaTrpAsp (SEQ ID NO:51)

CysXaaXaaCysXaaXaaAspXaaXaaCysXaaTrpAsp (SEQ ID NO:52)

The following 2 classes are preferred peptides which exclude semaphorin peptides encoded in open reading frames of Variola major or Vaccinia viruses Grasshopper Semaphorin I.

(f) TyrPhePhe[PheTyr]ArgGlu (SEQ ID NO:18)

Asp[LysTyr]Val[PheTyr][PheTyrLeu][PheTyrIleLeu][PheTyr] (SEQ ID NO:92)

Asp[LysTyr]Val[PheTyr][PheTyrIleLeu][PheTyrIle][PheTyr] (SEQ ID NO:93)

[ValIle]Tyr[PheTyrLeu][PheTyrIleLeu]Phe[ArgThr]Xaa[ThrAsn] (SEQ ID NO:94)

[ValIle]Tyr[PheTyrIleLeu][PheTyrIle]Phe[ArgThr]Xaa[ThrAsn] (SEQ ID NO:95)

[ValIle]Tyr[PheTyrIleLeu][PheTyrIleLeu]PheArgXaa[ThrAsn] (SEQ ID NO:96)

Val[PheTyr][PheTyrLeu][PheTyrIleLeu][PheTyr][ArgThr][GluAspVal][ThrAsn](SEQ ID NO:97)

Val[PheTyr][PheTyrIleLeu][PheTyrIle][PheTyr][ArgThr][GluAspVal][ThrAsn](SEQ ID NO:98)

Val[PheTyr][PheTyrIleLeu][PheTyrIleLeu][PheTyr]Arg[GluAspVal][ThrAsn](SEQ ID NO:99)

(n) CysXaaXaaXaaAspProXaaCysXaaTrpAsp (SEQ ID NO:48)

CysXaaXaaAspProXaaCysXaaTrpAsp (SEQ ID NO:49)

CysXaaXaaCysXaaXaaXaaAspXaaXaaCysXaaTrpAsp (SEQ ID NO:51)

CysXaaXaaCysXaaXaaAspXaaXaaCysXaaTrpAsp (SEQ ID NO:52)

The following 5 classes include peptides which encompass peptides encoded in open reading frames of Variola major or Vaccinia viruses. Accordingly, in the event that these viral peptides are not novel per se, the present invention discloses a hitherto unforseen and unforseeable utility for these peptides as immunosuppressants and targets of anti-viral therapy.

(b) CysGlyThr[AsnGly][AlaSerAsn][TyrPheHisGly][LysArgHisAsnGln] (SEQ ID NO:03)

CysGlyThr[AsnGly][AlaSerAsn]XaaXaaPro (SEQ ID NO:04)

CysGlyThr[AsnGly]XaaXaaXaaProXaa[CysAsp] (SEQ ID NO:05)

CysGlyThrXaaXaaXaaXaaProXaa[CysAsp]XaaXaa[TyrIle] (SEQ ID NO:06)

(f) Asp[LysPheTyr]Val[PheTyr][PheTyrIleLeu][PheTyrIleLeu][PheTyr] (SEQ ID NO:22)

[ValIle][PheTyr][PheTyrIleLeu][PheTyrIleLeu]Phe[ArgThr]Xaa[ThrAsn] (SEQ ID NO:23)

Val[PheTyr][PheTyrIleLeu][PheTyrIleLeu][PheTyr][ArgThr][GluAspVal][ThrAsn] (SEQ ID NO:100)

(i) [ArgLysAsn]Trp[ThrAlaSer][ThrAlaSer][PheTyrLeu]Leu[LysArg] (SEQ ID NO:30)

Trp[ThrAlaSer][ThrAlaSer][PheTyrLeu]LeuLys[AlaSerValIleLeu]XaaLeu (SEQ ID NO:33)

Trp[ThrAlaSer][ThrAlaSer]XaaLeuLysXaaXaaLeuXaaCys (SEQ ID NO:34)

TrpXaa[ThrSer]XaaLeuLysXaaXaaLeuXaaCys (SEQ ID NO:35)

(k) SerAla[ValIleLeu]CysXaa[PheTyr]XaaMet (SEQ ID NO:39)

(m) [ValLeuIle]ProXaaPro[ArgAla]ProGlyXaaCys (SEQ ID NO:42)

The disclosed semaphorin sequence data are used to define a wide variety of other semaphorin- and semaphorin receptor-specific binding agents using immunologic, chromatographic or synthetic methods available to those skilled in the art.

Of particular significance are peptides comprising unique portions of semaphorin-specific receptors and polypeptides comprising a sequence substantially similar to that of a substantially full-length semaphorin receptor. Using semaphorin peptides, these receptors are identified by a variety of techniques known to those skilled in the art where a ligand to the target receptor is known, including expression cloning as set out in the exemplification below. For other examples of receptor isolation with known ligand using expression cloning, see, Staunton et al (1989) Nature 339, 61; Davis et al (1991) Science 253, 59; Lin et al (1992) Cell 68, 775; Gearing et al (1989) EMBO 8, 3667; Aruffo and Seed (1987) PNAS 84, 8573 and references therein. Generally, COS cells are transfected to express a cDNA library or PCR product and cells producing peptides/polypeptides which bind a semaphorin/receptor peptide/polypeptide are isolated. For neurosemaphorin receptors, fetal brain cDNA libraries are preferred; for immunosemaphorin receptors, libraries derived from activated lymphoid or myeloid cell lines or tissue derived from sites of inflammation or delayed-type hypersensitivity are preferred; and for semaphorin and semaphorin receptor variants used by tumor cells to evade immune surveilance or suppress an immune response (oncosemaphorins), libraries derived from cancerous tissue or tumor cell lines resistant to the host immune system are preferred. Alternatively, PCR primers based upon known semaphorin/receptor sequences such as those disclosed herein are used to amplify PCR product from such tissues/cells. Other receptor/ligand isolation methods using immobilized ligand or antibody are known to those skilled in the art.

Semaphorin receptor peptides with receptor binding specificity are identified by a variety of ways including having conserved consensus sequences with other semaphorin receptors, by crosslinking to ligand or receptor-specific antibody, or preferably, by screening such peptides for semaphorin binding or disruption of semaphorin-receptor binding. Methods for identifying semaphorin receptor peptides with the requisite binding activity are described herein or otherwise known to those skilled in the art. By analogous methods, semaphorin receptor peptides are used to define additional semaphorin peptides with semaphorin binding specificity, particularly receptor specificity.

The various semaphorin and semaphorin receptor peptides are used to define functional domains of semaphorins, identify compounds that associate with semaphorins, design compounds capable of modulating semaphorin-mediated nerve and immune cell function, and define additional semaphorin and semaphorin receptor-specific binding agents. For example, semaphorin mutants, including deletion mutants are generated from the disclosed semaphorin sequences and used to identify regions important for specific protein-ligand or protein-protein interactions, for example, by assaying for the ability to mediate repulsion or preclude aggregation in cell-based assays as described herein. Further, x-ray crystallographic data of the disclosed protein are used to rationally design binding molecules of determined structure or complementarity for modulating growth cone growth and guidance.

Additional semaphorin- and receptor-specific agents include specific antibodies that can be modified to a monovalent form, such as Fab, Fab', or Fv, specifically binding oligopeptides or oligonucleotides and most preferably, small molecular weight organic receptor antagonists. For example, the disclosed semaphorin and receptor peptides are used as immunogens to generate semaphorin- and receptor-specific polyclonal or monoclonal antibodies. See, Harlow and Lane (1988) Antibodies, A Laboratory Manual, Cold Spring Harbor Laboratory, for general methods. Anti-idiotypic antibody, especially internal imaging anti-ids are also prepared using the disclosures herein.

In addition to semaphorin and semaphorin-receptor derived polypeptides and peptides, other prospective agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. See, e.g. Houghten et al. and Lam et al (1991) Nature 354, 84 and 81, respectively and Blake and Litzi-Davis (1992), Bioconjugate Chem 3, 510.

Useful agents are identified with a range of assays employing a compound comprising the subject peptides or encoding nucleic acids. A wide variety of in vitro, cell-free binding assays, especially assays for specific binding to immobilized compounds comprising semaphorin or semaphorin receptor peptide find convenient use. While less preferred, cell-based assays may be used to determine specific effects of prospective agents on semaphorin-receptor binding may be assayed. Optionally, the intracellular C-terminal domain is substituted with a sequence encoding a oligopeptide or polypeptide domain that provides a detectable intracellular signal upon ligand binding different from the natural receptor. Useful intracellular domains include those of the human insulin receptor and the TCR, especially domains with kinase activity and domains capable of triggering calcium influx which is conveniently detected by fluorimetry by preloading the host cells with Fura-2. More preferred assays involve simple cell-free in vitro binding of candidate agents to immobilized semaphorin or receptor peptides, or vice versa. See, e.g. Fodor et al (1991) Science 251, 767 for light directed parallel synthesis method. Such assays are amenable to scale-up, high throughput usage suitable for volume drug screening.

Useful agents are typically those that bind to a semaphorin or disrupt the association of a semaphorin with its receptor. Preferred agents are semaphorin-specific and do not cross react with other neural or lymphoid cell membrane proteins. Useful agents may be found within numerous chemical classes, though typically they are organic compounds; preferably small organic compounds. Small organic compounds have a molecular weight of more than 150 yet less than about 4,500, preferably less than about 1500, more preferably, less than about 500. Exemplary classes include peptides, saccharides, steroids, heterocyclics, polycyclics, substituted aromatic compounds, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways as described above, e.g. to enhance their proteolytic stability. Other methods of stabilization may include encapsulation, for example, in liposomes, etc.

The subject binding agents may be prepared in a variety of ways known to those skilled in the art. For example, peptides under about 60 amino acids can be readily synthesized today using conventional commercially available automatic synthesizers. Alternatively, DNA sequences may be prepared encoding the desired peptide and inserted into an appropriate expression vector for expression in a prokaryotic or eukaryotic host. A wide variety of expression vectors are available today and may be used in conventional ways for transformation of a competent host for expression and isolation. If desired, the open reading frame encoding the desired peptide may be joined to a signal sequence for secretion, so as to permit isolation from the culture medium. Methods for preparing the desired sequence, inserting the sequence into an expression vector, transforming a competent host, and growing the host in culture for production of the product may be found in U.S. Pat. Nos. 4,710,473, 4,711,843 and 4,713,339.

For therapeutic uses, the compositions and agents disclosed herein may be administered by any convenient way, preferably parenterally, conveniently in a pharmaceutically or physiologically acceptable carrier, e.g., phosphate buffered saline, saline, deionized water, or the like. Typically, the compositions are added to a retained physiological fluid such as blood or synovial fluid. For CNS administration, a variety of techniques are available for promoting transfer of the therapeutic across the blood brain barrier including disruption by surgery or injection, drugs which transciently open adhesion contact between CNS vasculature endothelial cells, and compounds which facilitate translocation through such cells. As examples, many of the disclosed therapeutics are amenable to directly injected or infused, contained within implants e.g. osmotic pumps, grafts comprising appropriately transformed cells. Generally, the amount administered will be empirically determined, typically in the range of about 10 to 1000 $\mu$g/kg of the recipient. For peptide agents, the concentration will generally be in the range of about 50 to 500 $\mu$g/ml in the dose administered. Other additives may be included, such as stabilizers, bactericides, etc. These additives will be present in conventional amounts.

The invention provides isolated nucleic acid sequences encoding the disclosed semaphorin and semaphorin receptor peptides and polypeptides, including sequences substantially identical to sequences encoding such polypeptides. An "isolated" nucleic acid sequence is present as other than a naturally occurring chromosome or transcript in its natural state and typically is removed from at least some of the nucleotide sequences with which it is normally associated with on a natural chromosome. A complementary sequence hybridizes to a unique portion of the disclosed semaphorin sequence under low stringency conditions, for example, at 50° C. and SSC (0.9M saline/0.09M sodium citrate) and that remains bound when subject to washing at 55° C. with SSC. Regions of non-identity of complementary nucleic acids are preferably or in the case of homologous nucleic acids, a nucleotide change providing a redundant codon. A partially pure nucleotide sequence constitutes at least about 5%, preferably at least about 30%, and more preferably at least about 90% by weight of total nucleic acid present in a given fraction.

Unique portions of the disclosed nucleic acid sequence are of length sufficient to distinguish previously known nucleic acid sequences. Thus, a unique portion has a nucleotide sequence at least long enough to define a novel oligonucleotide. Preferred nucleic acid portions encode a unique semaphorin peptide. The nucleic acids of the invention and portions thereof, other than those used as PCR primers, are usually at least about 60 bp and usually less than about 60 kb in length. PCR primers are generally between about 15 and 100 nucleotides in length.

Nucleotide (cDNA) sequences encoding several full length semaphorins are disclosed in herein. The invention also provides for the disclosed sequences modified by transitions, transversions, deletions, insertions, or other modifications such as alternative splicing and also provides for genomic semaphorin sequences, and gene flanking sequences, including regulatory sequences; included are DNA and RNA sequences, sense and antisense. Preferred DNA sequence portions include portions encoding the preferred amino acid sequence portions disclosed above. For antisense applications where the inhibition of semaphorin expression is indicated, especially useful oligonucleotides are between about 10 and 30 nucleotides in length and include sequences surrounding the disclosed ATG start site, especially the oligonucleotides defined by the disclosed sequence beginning about 5 nucleotides before the start site and ending about 10 nucleotides after the disclosed start site. Other especially useful semaphorin mutants involve deletion or substitution modifications of the disclosed cytoplasmic C-termini of transmembrane semaphorins. Accordingly, semaphorin mutants with semaphorin binding affinities but with altered intracellular signal transduction capacities are produced.

For modified semaphorin-encoding sequences or related sequences encoding proteins with semaphorin-like functions, there will generally be substantial sequence identity between at least a segment thereof and a segment encoding at least a portion of the disclosed semaphorin sequence, preferably at least about 60%, more preferably at least 80%, most preferably at least 90% identity. Homologous segments are particularly within semaphorin domain-encoding regions and regions encoding protein domains involved in protein-protein, particularly semaphorin-receptor interactions and differences within such segments are particularly conservative substitutions.

Typically, the invention's semaphorin peptide encoding polynucleotides are associated with heterologous sequences. Examples of such heterologous sequences include regulatory sequences such as promoters, enhancers, response elements, signal sequences, polyadenylation sequences, etc., introns, 5' and 3' noncoding regions, etc. Other useful heterologous sequences are known to those skilled in the art or otherwise disclosed references cited herein. According to a particular embodiment of the invention, portions of the semaphorin encoding sequence are spliced with heterologous sequences to produce soluble, secreted fusion proteins, using appropriate signal sequences and optionally, a fusion partner such as β-Gal.

The disclosed sequences are also used to identify and isolate other natural semaphorins and analogs. In particular, the disclosed nucleic acid sequences are used as hybridization probes under low-stringency or PCR primers, e.g. oligonucleotides encoding functional semaphorin domains are $^{32}$P-labeled and used to screen λcDNA libraries at low stringency to identify similar cDNAs that encode proteins with related functional domains. Additionally, nucleic acids encoding at least a portion of the disclosed semaphorin are used to characterize tissue specific expression of semaphorin as well as changes of expression over time, particularly during organismal development or cellular differentiation.

The semaphorin encoding nucleic acids can be subject to alternative purification, synthesis, modification, sequencing, expression, transfection, administration or other use by methods disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art. For example, the nucleic acids can be modified to alter stability, solubility, binding affinity and specificity, etc. semaphorin-encoding sequences can be selectively methylated, etc. The nucleic acid sequences of the present invention may also be modified with a label capable of providing a detectable signal, either directly or indirectly. Exemplary labels include radioisotopes, fluorescers, biotinylation, etc.

The invention also provides vectors comprising nucleic acids encoding semaphorin peptides, polypeptides or analogs. A large number of vectors, including plasmid and viral vectors, have been described for expression in a variety of eukaryotic and prokaryotic hosts. Advantageously, vectors may also include a promotor operably linked to the semaphorin-encoding portion. Vectors will often include one or more replication systems for cloning or expression, one or more markers for selection in the host, e.g. antibiotic resistance. The inserted semaphorin coding sequences may be synthesized, isolated from natural sources, prepared as hybrids, etc. Suitable host cells may be transformed/transfected/infected by any suitable method including electroporation, $CaCl_2$ mediated DNA uptake, viral infection, microinjection, microprojectile, or other methods.

Appropriate host cells include bacteria, archebacteria, fungi, especially yeast, and plant and animal cells, especially mammalian cells. Of particular interest are *E. coli, B. subtilis, Saccharomyces cerevisiae*, SP9 cells, C129 cells, 293 cells, Neurospora, and CHO, COS, HeLa cells, immortalized mammalian myeloid and lymphoid cell lines, and pluripotent cells, especially mammalian ES cells and zygotes. Preferred replication systems include M13, ColE1, SV40, baculovirus, lambda, adenovirus, AAV, BPV, etc. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced semaphorins or analogs.

For the production of stably transformed cells and transgenic animals, nucleic acids encoding the disclosed semaphorins may be integrated into a host genome by recombination events. For example, such a sequence can be microinjected into a cell, and thereby effect homologous recombination at the site of an endogenous gene, an analog or pseudogene thereof, or a sequence with substantial identity to an semaphorin-encoding gene. Other recombination-based methods such as nonhomologous recombinations, deletion of endogenous gene by homologous recombination, especially in pluripotent cells, etc., provide additional applications. Preferred transgenics and stable transformants over-express the disclosed receptor gene and find use in drug development and as a disease model. Alternatively, knock-out cells and animals find use in development and functional studies. Methods for making transgenic animals, usually rodents, from ES cells or zygotes are known to those skilled in the art.

The compositions and methods disclosed herein may be used to effect gene therapy. See, e.g. Zhu et al. (1993) Science 261, 209–211; Gutierrez et al. (1992) Lancet 339, 715–721. For example, cells are transfected with semaphorin sequences operably linked to gene regulatory sequences capable of effecting altered semaphorin expression or regulation. To modulate semaphorin translation, cells may be transfected with complementary antisense polynucleotides. For gene therapy involving the transfusion of semaphorin transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The following examples are offered by way of illustration and not by way of limitation.

EXAMPLES

I. Isolation and characterization of Grasshopper Semaphorin I (SEQ ID NOS:57 and 58) (previously referred to as Fasciclin IV)

In order to identify cell surface molecules that function in selective fasciculation, a series of monoclonal antibody (MAb) screens was conducted. The immunogen used for most of these screens was membranes from the longitudinal connectives (the collection of longitudinal axons) between adjacent segmental ganglia of the nervous system of the larval grasshopper. From these screens, MAb 3B11 and 8C6 were used to purify and characterize two surface glycoproteins, fasciclin I and fasciclin II, see, Bastiani et al., 1987; the genes encoding both were subsequently cloned, see, Snow et al. 1989, Zinn et al. 1988, and Harrelson and Goodman, 1988.

Another MAb isolated during these screens, MAb 6F8, was chosen for the present study because, just as with fasciclin I and fasciclin II, the antigen recognized by this MAb is expressed on a different but overlapping subset of axon pathways in the developing CNS. The 6F8 antigen appears to be localized on the outside of cell surfaces, as indicated by MAb binding when incubated both in live preparations, and in fixed preparations in which no detergents have been added. Because the 6F8 antigen is a surface glycoprotein expressed on a subset of axon fascicles (see below), we call it fasciclin IV.

Fasciclin IV expression begins early in embryonic development before axonogenesis. At 29% of development, expression is seen on the surface of the midline mesectodermal cells and around 5–7 neuroblasts and associated ectodermal cells per hemisegment. This expression is reminiscent of the mesectodermal and neuroblast-associated expression observed with both fasciclin I and fasciclin II; however, in each case, the pattern resolves into a different subset of neuroblasts and associated ectodermal cells.

At 32% of development, shortly after the onset of axonogenesis in the CNS, fasciclin IV expression is seen on the surface of the axons and cell bodies of the three pairs of MP4, MP5, and MP6 midline progeny, the three U motoneurons, and on several unidentified neurons in close proximity to the U's. This is in contrast to fasciclin II, which at this stage is expressed on the MP1 and dMP2 neurons, and fasciclin I, which is expressed on the U neurons but not on any midline precursor progeny.

The expression of fasciclin IV on a subset of axon pathways is best observed around 40% of development, after the establishment of the first longitudinal and commissural axon pathways. At this stage, the protein is expressed on two longitudinal axon fascicles, a subset of commissural axon fascicles, a tract extending anteriorly along the midline, and a subset of fascicles in the segmental nerve (SN) and intersegmental nerve (ISN) roots.

Specifically, fasciclin IV is expressed on the U fascicle, a longitudinal pathway (between adjacent segmental neuromeres) pioneered in part by the U neurons, and on the A/P longitudinal fascicle (in part an extension of the U fascicle within each segmental neuromere). In addition, fasciclin IV is also expressed on a second narrower, medial, and more ventral longitudinal pathway. The U axons turn and exit the CNS as they pioneer the ISN; the U's and many other axons within the ISN express fasciclin IV. The continuation of the U fascicle posterior to the ISN junction is also fasciclin IV-positive. The specificity of fasciclin IV for distinct subsets of longitudinal pathways can be seen by comparing fasciclin IV and fasciclin II expression in the same embryo; fasciclin IV is expressed on the U and A/P pathways whereas fasciclin II is expressed on the MP1 pathway.

The axons in the median fiber tract (MFT) also express fasciclin IV. The MFT is pioneered by the three pairs of progeny of the midline precursors MP4, MP5, and MP6. The MFT actually contains three separate fascicles. The axons of the two MP4 progeny pioneer the dorsal MFT fascicle and then bifurcate at the posterior end of the anterior commissure; whereas the axons of the two MP6 progeny pioneer the ventral MFT fascicle and then bifurcate at the anterior end of the posterior commissure. Fasciclin IV is expressed on the cell bodies of the six MP4, MP5, and MP6 neurons, and on their growth cones and axons as they extend anteriorly in the MFT and bifurcate in one of the two commissures. However, this expression is regional in that once these axons bifurcate and begin to extend laterally across the longitudinal pathways and towards the peripheral nerve roots, their expression of fasciclin IV greatly decreases. Thus, fasciclin IV is a label for the axons in the MFT and their initial bifurcations in both the anterior and posterior commissures. It appears to be expressed on other commissural fascicles as well. However, the commissural expression of fasciclin IV is distinct from the transient expression of fasciclin II along the posterior edge of the posterior commissure, or the expression of fasciclin I on several different commissural axon fascicles in both the anterior and posterior commissure (Bastiani et al., 1987; Harrelson and Goodman, 1988).

Fasciclin IV is also expressed on a subset of motor axons exiting the CNS in the SN. The SN splits into two major branches, one anterior and the other posterior, as it exits the CNS. Two large bundles of motoneuron axons in the anterior branch express fasciclin. IV at high levels; one narrow bundle of motoneuron axons in the posterior branch expresses the protein at much lower levels. Fasciclin IV is also expressed on many of the axons in the ISN.

The CNS and nerve root expression patterns of fasciclin IV, fasciclin I, and fasciclin II at around 40% of embryonic development are summarized in. Although there is some overlap in their patterns (e.g., both fasciclin IV and fasciclin I label the U axons), these three surface glycoproteins label distinct subsets of axon pathways in the developing CNS.

Fasciclin IV is expressed on epithelial bands in the developing limb bud

Fasciclin IV is expressed on the developing limb bud epithelium in circumferential bands; at 34.5% of development these bands can be localized with respect to constrictions in the epithelium that mark presumptive segment boundaries. In addition to a band just distal to the trochanter/coxa segment boundary, bands are also found in the tibia, femur, coxa, and later in development a fifth band is found in the tarsus. Fasciclin IV is also expressed in the nascent chordotonal organ in the dorsal aspect of the femur. The bands in the tibia, trochanter, and coxa completely encircle the limb. However, the femoral band is incomplete, containing a gap on the anterior epithelia of this segment.

The position of the Ti1 axon pathway with respect to these bands of fasciclin IV-positive epithelia suggests a potential role for fasciclin IV in guiding the Ti1 growth cones. First, the band of fasciclin IV expression in the trochanter, which is approximately three epithelial cell diameters in width when encountered by the Ti1 growth cones, is the axial location where the growth cones reorient from proximal migration to circumferential branch extension. The Tr1 cell, which marks the location of the turn, lies within this band, usually over the central or the proximal cell tier. Secondly, although there is a more distal fasciclin IV expressing band in the femur, where a change in Ti1 growth is not observed, there exists a gap in this band such that fasciclin IV expressing cells are not traversed by the Ti1 growth cones. The Ti1 axons also may encounter a fasciclin IV expressing region within the coxa, where interactions between the growth cones, the epithelial cells, and the Cx1 guidepost cells have not yet been investigated.

In addition to its expression over the surface of bands of epithelial cells, fasciclin IV protein, as visualized with MAb 6F8, is also found on the basal surface of these cells in a punctate pattern. This punctate staining is not an artifact of the HRP immunocytochemistry since fluorescent visualization of MAb 6F8 is also punctate. The non-neuronal expression of fasciclin IV is not restricted to limb buds. Circumferential epithelial bands of fasciclin IV expression are also seen on subesophageal mandibular structures and on the developing antennae.

MAb directed against fasciclin IV can alter the formation of the Ti1 axon pathway in the limb bud The expression of fasciclin IV on an epithelial band at a key choice point in the formation of the Ti1 axon pathway led us to ask whether this protein is involved in growth cone guidance at this location. To answer this question, we cultured embryos, or epithelial fillets (e. g., O'Connor et al., 1990), during the 5% of development necessary for normal pathway formation, either in the presence or absence of MAb 6F8 or 6F8 Fab fragments. Under the culture conditions used for these experiments, defective Ti1 pathways are observed in 14% of limbs (Chang et al., 1992); this defines the baseline of abnormalities observed using these conditions. For controls we used other MAbs and their Fab fragments that either bind to the surfaces of these neurons and epithelial cells (MAb 3B11 against the surface protein fasciclin I) or do not (MAb 4D9 against the nuclear protein engrailed; Patel et al., 1989). To assess the impact of MAb 6F8 on Ti1 pathway formation, we compared the percentage of aberrant pathways observed following treatment with MAb 6F8 to that observed with MAbs 3B11 and 4D9. Our cultures began at 32% of development when the Ti1 growth cones have not yet reached the epithelium just distal to the trochanter/coxa boundary and therefore have not encountered epithelial cells expressing fasciclin IV. Following approximately 30 hours in culture (~4% of development), embryos were fixed and immunostained with antibodies to HRP in order to visualize the Ti1 axons and other neurons in the limb bud. Criteria for scoring the Ti1 pathway, and the definition of "aberrant", are described in detail in the Experimental Procedures.

Although MAb 6F8 does not arrest pathway formation, several types of distinctive, abnormal pathways are observed. These defects generally begin where growth cones first contact the fasciclin IV expressing cells in the trochanter. Normally, the Ti1 neurons each have a single axon, and the axons of the two cells are fasciculated in that portion of the pathway within the trochanter. Following treatment with MAb 6F8, multiple long axon branches are observed within, and proximal to, the trochanter. Two major classes of pathways are taken by these branches; in 36% of aberrant limbs, multiple, long axon branches extend ventrally in the region distal to the Cx1 cells which contains the band of fasciclin IV expressing epithelial cells. In the ventral region of the trochanter, these branches often independently turn proximally to contact the Cx1 cells, and thus complete the pathway in this region.

In the second major class of pathway defect, seen in 47% of aberrant limbs, axon branches leave the trochanter at abnormal, dorsal locations, and extend proximally across the trochanter/coxa boundary. These axons then veer ventrally, often contacting the Cx1 neurons. The remaining 17% of defects include defasciculation distal to the trochanter, axon branches that fail to turn proximally in the ventral trochanter and continue into the posterior compartment of the limb, and axon branches which cross the trochanter/coxa boundary and continue to extend proximally without a ventral turn.

When cultured in the presence of MAb 6F8, 43% of limbs exhibited malformed Ti1 pathways (n=381) as compared to 11% with MAb 3B11 (n=230) and 5% with MAb 4D9 (n=20). These percentages are pooled from treatments with MAbs concentrated from hybridoma supernatant, IgGs isolated from these supernatants, and Fab fragments isolated from these IgG preparations (see Experimental Procedures). The frequency of malformed Ti1 pathways and the types of defects observed showed no significant variation regardless of the method of antibody preparation or type of antibody used. Since Fabs show similar results as IgGs, the effects of MAb 6F8 are not due to cross linking by the bivalent IgG.

In summary, following treatment with MAb 6F8, the Ti1 pathway typically exhibits abnormal morphology beginning just distal to the trochanter and at the site of fasciclin IV expression. The two most common types of Ti1 pathway defects described above occur in 36% of experimental limbs (treated with MAb 6F8), but are seen in only 4% of control limbs (treated with MAbs 3 B11 and 4D9).

Fasciclin IV cDNAs encode a novel integral membrane protein

Grasshopper fasciclin IV was purified by passing crude embryonic grasshopper lysates over a MAb 6F8 column. After affinity purification, the protein was eluted, precipitated, denatured, modified at cysteines, and digested with either trypsin or Lys-C. Individual peptides were resolved by reverse phase HPLC and microsequenced using standard methods.

The amino acid sequences derived from these proteolytic fragments were used to generate oligonucleotide probes for PCR experiments, resulting in products that were used to isolate cDNA clones from the Zinn embryonic grasshopper cDNA library (Snow et al., 1988). Sequence analysis of these cDNAs reveals a single open reading frame (ORF) encoding a protein with two potential hydrophobic stretches of amino acids: an amino-terminal signal sequence of 20 residues and (beginning at amino acid 627) a potential transmembrane domain of 25 amino acids. Thus, the deduced protein has an extracellular domain of 605 amino acids, a transmembrane domain, and a cytoplasmic domain of 78 amino acids. The calculated molecular mass of the mature fasciclin IV protein is 80 kd and is confirmed by Western blot analysis of the affinity purified and endogenous protein as described below. The extracellular domain of the protein includes 16 cysteine residues that fall into three loose clusters but do not constitute a repeated domain and are not similar to other known motifs with cysteine repeats. There are also six potential sites for N-linked glycosylation in the extracellular domain. Treatment of affinity purified fasciclin IV with N-Glycanase demonstrates that fasciclin IV does indeed contain N-linked oligosaccharides. Fasciclin IV shows no sequence similarity when compared with other proteins in the PIR data base using BLASTP (Altschul et al., 1990), and is therefore a novel type I integral membrane protein.

A polyclonal antiserum directed against the cytoplasmic domain of the protein encoded by the fasciclin IV cDNA was used to stain grasshopper embryos at 40% of development. The observed staining pattern was identical to that seen with MAb 6F8. On Western blots, this antiserum recognizes the protein we affinity purified using MAb 6F8 and then subjected to microsequence analysis. Additionally, the polyclonal serum recognizes a protein of similar molecular mass from grasshopper embryonic membranes. Taken together these data indicate that the sequence we have obtained is indeed fasciclin IV.

Four other cell surface proteins that label subsets of axon pathways in the insect nervous system (fasciclin I, fasciclin II, fasciclin m, and neuroglian) are capable of mediating homophilic cell adhesion when transfected into S2 cells in vitro (Snow et al., 1989; Elkins et al., 1990b; Grenningloh et al., 1990). To ask whether fasciclin IV can function as a homophilic cell adhesion molecule, the fasciclin IV cDNA with the complete ORF was placed under the control of the inducible metallothionein promoter (Bunch et al., 1988), transfected into S2 cells, and assayed for its ability to promote adhesion in normally non-adhesive S2 cells. Following induction with copper, fasciclin IV was synthesized in these S2 cells as shown by Western blot analysis and cell surface staining of induced S2 cells with the polyclonal antiserum described above.

We observed no evidence for aggregation upon induction of fasciclin IV expression, thus suggesting that, in contrast to the other four proteins, fasciclin IV does not function as a homophilic cell adhesion molecule. Alternatively, fasciclin IV-mediated aggregation might require some further post-translational modification, or co-factor, not supplied by the S2 cells, but clearly this protein acts differently in the S2 cell assay than the other four axonal glycoproteins previously tested. This is consistent with the pattern of fasciclin IV expression in the embryonic limb since only the epithelial cells and not the Ti1 growth cones express fasciclin IV, and yet antibody blocking experiments indicate that fasciclin IV functions in the epithelial guidance of these growth cones. Such results suggest that fasciclin IV functions in a heterophilic adhesion or signaling system.

Discussion

Fasciclin IV is expressed on groups of axons that fasciculate in the CNS, suggesting that, much like other insect axonal glycoproteins, it functions as a homophilic cell adhesion molecule binding these axons together. Yet, in the limb bud, fasciclin IV is expressed on a band of epithelium but not on the growth cones that reorient along this band, suggesting a heterophilic function. That fasciclin IV functions in a heterophilic rather than homophilic fashion is supported by the lack of homophilic adhesion in S2 cell aggregation assays. In contrast, fasciclin I, fasciclin II, fasciclin III, and neuroglian all can function as homophilic cell adhesion molecules (Snow et al., 1989; Elkins et al., 1990b; Grenningloh et al., 1990).

cDNA sequence analysis indicates that fasciclin IV is an integral membrane protein with a novel sequence not related to any protein in the present data base. Thus, fasciclin IV represents a new type of protein that functions in the epithelial guidance of pioneer growth cones in the developing limb bud. Given its expression on a subset of axon pathways in the developing CNS, fasciclin IV functions in the guidance of CNS growth cones as well.

The results from the MAb blocking experiments illuminate several issues in Ti1 growth cone guidance and axon morphogenesis in the limb. First, the most striking change in growth cone behavior in the limb is the cessation of proximal growth and initiation of circumferential extension of processes upon encountering the trochanter/coxa boundary region (Bentley and Caudy, 1983; Caudy and Bentley, 1987). This could be because the band of epithelial cells within the trochanter promotes circumferential growth, or because the cells comprising the trochanter/coxa boundary and the region just proximal to it are non-permissive or aversive for growth cone migration, or both. The extension of many axon branches across the trochanter/coxa boundary following treatment with MAb 6F8 suggests that the trochanter/coxa boundary cells, which do not express fasciclin IV, are not aversive or non-permissive. Thus the change in behavior at the boundary appears to be due to the ability of fasciclin IV expressing epithelial cells to promote circumferential extension of processes from the Ti1 growth cones.

Secondly, treatment with MAb 6F8 results in frequent defasciculation of the axons of the two Ti1 neurons, and also formation of abnormal multiple axon branches, within the trochanter over fasciclin IV-expressing epithelial cells. Previous studies have shown that treatment with antibodies against ligands expressed on non-neural substrates (Landmesser et al., 1988), or putative competitive inhibitors of substrate ligands (Wang and Denburg, 1992) can promote defasciculation and increased axonal branching. Our results suggest that Ti1 axon:axon fasciculation and axon branching also are strongly influenced by interactions with substrate ligands, and that fasciclin IV appears to be a component of this interaction within the trochanter.

Thirdly, despite the effects of MAb 6F8 on axon branching, and on crossing the trochanter/coxa boundary, there remains a pronounced tendency for branches to grow ventrally both within the trochanter and within the distal region of the coxa. Consequently, all signals which can promote ventral migration of the growth cones have not been blocked by MAb 6F8 treatment. Antibody treatment may have a threshold effect in which ventral growth directing properties of fasciclin IV are more robust, and less incapacitated by treatment, than other features; alternatively, guidance information promoting ventral migration may be independent of fasciclin IV. Time lapse video experiments to determine how the abnormal pathways we observe actually form can resolve these issues.

These results demonstrate that fasciclin IV functions as a guidance cue for the Ti1 growth cones just distal to the trochanter/coxa boundary, is required for these growth cones to stop proximal growth and spread circumferentially, and that the function of fasciclin IV in Ti1 pathway formation result from interactions between a receptor/ligand on the Ti1 growth cones and fasciclin IV on the surface of the band of epithelial cells results in changes in growth cone morphology and subsequent reorientation. Fasciclin IV appears to elicit this change in growth cone morphology and orientation via regulation of adhesion, a signal transduction function, or a combination of the two.

Experimental Procedures

Enmunocytochemistry

Grasshopper embryos were obtained from a colony maintained at the U. C. Berkeley and staged by percentage of total embryonic development (Bentley et al., 1979). Embryos were dissected in PBS, fixed for 40 min in PEM-FA [0.1M PIPES (pH6.95), 2.0 mM EGTA, 1.0 mM $MgSO_4$, 3.7% formaldehyde], washed for 1 hr with three changes in PBT (1×PBS, 0.5% Triton X-100, 0.2% BSA), blocked for 30 min in PBT with 5% normal goat serum, and incubated overnight at 4° C. in primary antibody. PBSap (1×PBS, 0.1% Saponin, o.2% BSA) was used in place of PBT with MAb 8G7. Antibody dilutions were as follows: MAb 6F8 1:1, polyclonal antisera directed against a fasciclin IV bacterial fusion protein (#98-3) 1:400; MAb 8G7 1:4; MAb 8C6 1:1. The embryos were washed for one hour in PBT with three changes, blocked for 30 min, and incubated in secondary antibody for at least 2 hr at room temperature. The secondary antibodies were HRP-conjugated goat anti-mouse and anti-rat IgG (Jackson Immunoresearch Lab), and were diluted 1:300. Embryos were washed in PBT for one hour with three changes and then reacted in 0.5% diaminobenzidine (DAB) in PBT. The reaction was so with several washes in PBS and the embryos were cleared in a glycerol series (50%, 70%, 90%), mounted and viewed under Nomarski or bright field optics. For double-labelled preparations the first HRP reaction was done in PBT containing 0.06% NiCl, followed by washing, blocking, and incubation overnight in the second primary antibody. The second antibody was visualized with a DAB reaction as described above. Embryos cultured in the presence of monoclonal antibodies were fixed and incubated overnight in goat anti-HRP (Jackson Immunoresearch Labs) conjugated to RITC (Molecular Probes), washed for one hour in PBT with three changes, mounted in 90% glycerol, 2.5% DABCO (Polysciences), and viewed under epifluorescence. S2 cells were stained with polyclonal sera #98-3 diluted 1:400 and processed as described previously (Snow et al., 1989).

Monoclonal Antibody Blocking Experiments

In order to test for functional blocking, monoclonal antibody reagents were prepared as follows. Hybridoma supernatant was brought to 20% with $H_2O$-saturated $(NH_4)_2$, incubated in ice 1 hr, and spun at 15,000 g at 4° C. for 20 min. The supernatant was brought to 56% with $H_2O$-saturated $(NH_4)_2$, incubated overnight at 4° C., spun as above. The pellet was resuspended in PBS using approximately 1/40 volume of the original hybridoma supernatant (often remaining a slurry) and dialyzed against 1×PBS overnight at 4° C. with two changes. This reagent is referred to as "concentrated hybridoma supernatant." Purified IgG was obtained by using Immunopure Plus Immobilized Protein A IgG Purification Kit (Pierce) to isolate IgG from the concentrated hybridoma supernatant. Fab fragments were obtained using the ImmunoPure Fab Preparation Kit (Pierce) from the previously isolated IgGs. For blocking experiments each reagent was diluted into freshly made supplemented RPMI culture media (O'Connor et al., 1990) and dialyzed overnight at 4° C against 10 volumes of the same culture media. Dilutions were as follows: concentrated hybridoma supernatant 1:4; purified IgG 150 mg/ml; Fab 75 mg/ml.

Embryos for culture experiments were carefully staged to between 31 and 32% of development. As embryos in each clutch typically differ by less that 1% of embryonic development from each other, the growth cones of the Ti1 neurons at the beginning of the culture period were located approximately in the mid-femur, well distal to the trochanter/coxa segment boundary. From each clutch at least two limbs were filleted and the Ti1 neurons labelled with the lipophillic dye Di I (Molecular Probes) as described (O'Connor et al., 1990) in order to confirm the precise location of the Ti1 growth cones. Prior to culturing, embryos were sterilized and dissected (Chang et al., 1992). The entire amnion and dorsal membrane was removed from the embryo to insure access of the reagents during culturing. Embryos were randomly divided into groups and cultured in one of the blocking reagents described above. Cultures were incubated with occasional agitation at 30° C. for 30 hrs. At the end of the culture period embryos were fixed and processed for analysis as described above in immunocytochemistry.

For each culture experiment, the scoring of the Ti1 pathway in each limb was confirmed independently by a second observer. There was no statistically significant variation between the two observers. Limbs from MAb cultured embryos were compared to representative normal limbs from non-MAb cultured embryos and were scored as abnormal if any major deviation from the normal Ti1 pathway was observed. The Ti1 pathway was scored as abnormal for one or more of the following observed characteristics: (1) defasciculation for a minimum distance of approximately 25 mm anywhere along the pathway, (2) multiple axon branches that extended ventrally within the trochanter, (3) presence of one or more axon branches that crossed the trochanter/coxa boundary dorsal to the Cx1 cells, but then turned ventrally in the coxa and contacted the Cx1 cells, (4) the presence of axon branches that crossed the trochanter/coxa segment boundary, did not turn ventrally, but continued proximally toward the CNS, and (5) failure of ventrally extended axons within the trochanter to contact and reorient proximally to the Cx1 cells. For each MAb tested, the data are presented as a percentage of the abnormal Ti1 pathways observed.

Protein Affinity Purification and Microsequencing

Grasshopper fasciclin IV was purified by passing crude embryonic grasshopper lysate (Bastiani et al., 1987) over an Affi-Gel 15 column (Rio Rad) conjugated with the monoclonal antibody 6F8. Protein was eluted with 50 mM DEA (H 11.5), 0.1% Lauryldimethylamine oxide (Cal Bio Chem), and 1 mM EDTA. Protein was then precipitated, denatured, modified at cysteines, and digest with either trypsin or Lys-C (Boehringer-Mannheim). Individual peptides were resolved by RP-HPLC and microsequenced (Applied Biosystems 4771 Microsequencer) using standard chemistry.

PCR Methods

DNA complementary to poly(A)+ RNA from 45%–50% grasshopper embryos was prepared (Sambrook et al., 1989). PCR was performed using Perkin Elmer Taq polymerase (Saiki et al., 1988), and partially degenerate (based on grasshopper codon bias) oligonucleotides in both orientations corresponding to a portion of the protein sequence of several fasciclin IV peptides as determined by microsequencing. These oligonucleotides were designed so as not to include all of the peptide-derived DNA sequence, leaving a remaining 9–12 base pairs that could be used to confirm the correct identity of amplified products. All possible combinations of these sequences were tried. 40 cycles were performed, the parameters of each cycle as follows: 96° for one min; a sequentially decreasing annealing temperature (2° C./cycle, starting at 65° C. and ending at 55° C. for remaining 35 cycles) for 1 min; and at 72° C. for one min. Reaction products were cloned into the Sma site of M13 mp10 and sequenced. Two products, 1074 bp and 288 bp in length, contained DNA 3' to the oligonucleotide sequences encoded the additional amino acid sequence of the fasciclin IV peptide from which the oligonuceotides were derived. These two fragments have one end in common, and the oligonucleotides used to amplify them correspond to the amino acid sequences -Met-Tyr-Val-Gln-Phe-Gly-Glu-Glu-, and -Met-Asp-Glu-Ala-Val-Pro-Ala-Phe- (fasciclin IV residue 29-386), and -His-Thr-Leu-Met-Asp-Glu-Ala-, and -Lys-Asn-Tyr-Val-Val-Arg-Met-Asp-Glu (fasciclin IV residue 376-472).

cDNA Isolation and Sequence Analysis

Both PCR products were used to screen $1\times10^6$ clones from a grasshopper embryonic cDNA library (Snow et al., 1988). 21 clones that hybridized to both fragments were recovered, and one 2600 bp clone was sequenced using the dideoxy chain termination method (Sanger et al., 1977) and Sequenase (US Biochemical Corp.). Templates were made from M13 mp10 vectors containing inserts generated by sonication of plasmid clones. One cDNA was completely sequenced on both strands using Oligonucleotides and double strand sequencing of plasmid DNA (Sambrook et al., 1989) to fill gaps. Two additional cDNAs were analyzed by double strand sequencing to obtain the 3' 402 bp of the transcript. All three cDNAs were used to construct a plasmid containing the entire transcript. The complete transcript sequence is 2860 bp in length with 452 bp of 5' and 217 bp of 3' untranslated sequences containing stop codons in all reading frames. The predicted protein sequence was analyzed using the FASTDB and BLASTP programs (Intelligenetics). The fasciclin IV ORF unambiguously contains 10 of the 11 peptide sequences determined by microsequencing the fasciclin IV trypsin and Lys-C peptides.

Generation of Polyclonal Antibodies From Bacterial Fusion Proteins

Bacterial trpE fusion proteins were constructed using pATH (Koerner et al., 1991) vectors, three restriction fragments encoding extracellular sequences, and one fragment (770 bp HindII/Eco R1, which includes amino acids 476-730) encoding both extracellular and intracellular sequences (designed #98-3). Fusion proteins were isolated by making an extract of purified inclusion bodies (Spindler et al., 1984), and rats were immunized with ~70 mg of protein emulsified in RIBI adjuvant (Immunochem Reserch). Rats were injected at two week intervals and serum was collected 7 days following each injection. Sera were tested histologically on grasshopper embryos at 45% of development. Construct #98-3 showed a strong response and exhibited a staining pattern identical to that of MAb 6F8. Two of the extracellular constructs responded weakly but also showed the fasciclin IV staining pattern. All pre-immune sera failed to stain grasshopper embryos.

S2 Cell Transfections, Aggregation Assays, and Western Analysis

A restriction fragment containing the full length fasciclin IV cDNA was cloned into pRmHa-3 (Bunch et al, 1988) and co-transformed into Drosophila S2 cells (Schneider, 1972) with the plasmid pPC4 (Jokerst et al., 1989), which confers a-amanitin resistance. S2 cells were transformed using the Lipofectin Reagent and recommended protocol (BRL) with nor modifications. All other S2 cell manipulations are essentially as described (Snow et al., 1989), including adhesion assays. Fasciclin IV expression in transformed cell lines was induced for adhesion assays and histology by adding $CuSo_4$ to 0.7 mM and incubating for at least 48 hrs. Northern analysis confirmed transcription of fasciclin TV and surface-associated staining of the S2 cells with polyclonal serum #98-3 strongly suggests fasciclin IV is being transported to the cell surface. Preparation of membranes from S2 cells and from grasshopper embryos, PAGE, and Western blot were performed as previously described (Elkins et al., 1990b) except that signal was detected using the enhanced chemi-luminescence immunodetection system kit (Amersham). Amount of protein per lane in each sample loaded: fasciclin IV protein, ~5 ng; S2 cell membranes, 40 mg; grasshopper membranes 80 mg. Amounts of protein loaded were verified by Ponceau S staining of the blot prior to incubation with the antibody.

References cited in Example I

Altschul, S. F., Gish, W., Miller, W., Myers, E. W., and Lipman, D. J. (1990). Basic local alignment search tool. J. Mol. Biol. 215, 403–410.

Bastiani, M. J., de Couet, H. G., Quinn, J. M. A., Karlstrom, R. O., Kotrla, K., Goodman, C. S., and Ball, E. E. (1992). Position-specific expression of the annulin protein during grasshopper embryogenesis. Dev. Biol., in press.

Bastiani, M. J., du Lac, S., and Goodman, C. S. (1986). Guidance of neuronal growth cones in the grasshopper embryo. I. Recognition of a specific axonal pathway by the pCC neuron. J. Neurosci. 6, 3518–3531.

Bastiani, M. J., and Goodman, C. S. (1986). Guidance of neuronal growth cones in the grasshopper embryo: III. Recognition of specific glial pathways. J. Neurosci. 6, 3542–3551.

Bastiani, M. J., Harrelson, A. L., Snow, P. M., and Goodman, C. S. (1987). Expression of fasciclin I and II glycoproteins on subsets of axon pathways during neuronal development in the grasshopper. Cell 48, 745–755.

Bastiani, M. J., Raper, J. A., and Goodman, C. S. (1984). Pathfinding by neuronal growth cones in grasshopper embryos. III. Selective affinity of the G growth cone for the P cells within the A/P fascicle. J. Neurosci. 4, 2311–2328.

Bentley, D., and Caudy, M. (1983). Pioneer axons lose directed growth after selective killing of guidepost cells. Nature. 304, 62–65.

Bentley, D., Keshishian, H., Shankland, M., and Toroian-Raymond, A. (1979). Quantitative staging of embryonic development of the grasshopper, Schistocerca nitens. J. Embryol. Exp. Morph. 54, 47–74.

Bentley, D., and O'Connor, T. P. (1992). Guidance and steering of peripheral pioneer growth cones in grasshopper embryos. In The Nerve Growth Cone, P. C. Letourneau, S. B. Kater, and E. R. Macagno eds. (New York: Raven Press, Ltd.), pp. 265–282.

Bunch, T. A., Grinblat, Y., and Goldstein, L. S. B. (1988). Characterization and use of the Drosophila metallothionein promoter in cultured Drosophila melanogaster cells. Nucleic Acids Res. 16, 1043–1061.

Chang, W. S., Serikawa, K., Allen, K., and Bentley, D. (1992). Disruption of pioneer growth cone guidance in vivo by removal of glycosyl-phosphatidylinositol-anchored cell surface proteins. Development. 114, 507–519.

Caudy, M., and Bentley, D. (1987). Pioneer growth cone behavior at a differentiating limb segment boundary in the grasshopper embryo. Dev. Biol. 119, 454–465.

Chou, P. Y., and Fasman, G. D. (1974). Prediction of protein conformation. Biochemistry. 13, 222–245.

Elkins, T., Zinn, K., McAllister, L., Hoffmann, F. M., and Goodman, C. S. (1990a). Genetic analysis of a Drosophila neural cell adhesion molecule: Interaction of fasciclin I and abelson tyrosine kinase mutations. Cell. 60, 565–575.

Elkins, T., Hortsch, M., Bieber, A. J., Snow, P. M., and Goodman, C. S. (1990b). Drosophila fasciclin I is a novel homophilic adhesion molecule that along with fasciclin III can mediate cell sorting. J. Cell Biol. 110, 1825–1832.

Goodman, C. S., Bate, C. M., and Spitzer, N. C. (1981). Embryonic development of identified neurons: Origin and transformation of the H cell. J. Neurosci. 1, 94–102.

Grenningloh, G., Bieber, A., Rehm, J., Snow, P. M., Traquina, Z., Hortsch, M., Patel, N. H., and Goodman, C. S. (1990). Molecular genetics of neuronal recognition in Drosophila: Evolution and function of immunoglobulin superfamily cell adhesion molecules. Cold Spring Harbor Symp. Quant. Biol. 55, 327–340.

Grenningloh, G., Rehm, E. J., and Goodman, C. S. (1991). Genetic analysis of growth cone guidance in Drosophila: Fasciclin II functions as a neuronal recognition molecule. Cell. 67, 45–57.

Harrelson, A. L., and Goodman, C. S. (1988). Growth cone guidance in insects: Fasciclin II is a member of the immunoglobulin superfamily. Science. 242, 700–708.

Jacobs, J. R., and Goodman, C. S. (1989). Embryonic development of axon pathways in the Drosophila CNS. I. A glial scaffold appears before the first growth cones. J. Neurosci. 7, 2402–2411.

Jay, D. J., and Keshishian, H. (1990). Laser inactivation of fasciclin I disrupts axon adhesion of grasshopper pioneer neurons. Nature. 348, 548–551.

Jokerst, R. S., Weeks, J. R. Zehring, W. A., and Greenleaf, A. L. (1989). Analysis of the gene encoding the largest subunit of RNA polymerase II in Drosophila. Mol. Gen. Genet. 215, 266–275.

Koerner, T. J., Hill, J. E., Myers, A. M., and Tzagoloff, A. (1991). High-expression vectors with multiple cloning sites for construction of trpE-fusion genes: pATH vectors. Methods Enzymol. 194, 477–490.

Landmesser, L., Dahm L., Schultz, K., and Rutishauser, U. (1988). Distinct roles for adhesion molecules during innervation of embryonic chick muscle. Dev. Biol. 130, 645–670.

Lefcort, F., and Bentley, D. (1987). Pathfinding by pioneer neurons in isolated, opened and mesoderm-free limb buds of embryonic grasshoppers. Dev. Biol. 119, 466–480.

Lefcort, F., and Bentley, D. (1989). Organization of cytoskeletal elements and organelles preceding growth cone emergence from an identified neuron in situ. J. Cell. Biol. 108, 1737–1749.

O'Connor, T. P., Duerr, J. S., and Bentley, D. (1990). Pioneer growth cone steering decisions mediated by single filopodial contacts in situ. J. Neurosci. 10, 3935–3946.

Patel. N. H., Martin-Blanco, E., Coleman, K. G., Poole, S. J., Ellis, M. C., Kornberg, T. B., and Goodman, C. S. (1989). Expression of engrailed proteins in arthropods, annelids, and chordates. Cell. 58, 955–968.

Patel, N. H., Snow, P. M., and Goodman, C. S. (1987). Characterization and cloning of fasciclin III: A glycoprotein expressed on a subset of neurons and axon pathways in Drosophila. Cell. 48, 975–988.

Raper, J. A., Bastiani, M. J., and Goodman, C. S. (1984). Pathfinding by neuronal growth cones in grasshopper embryos. IV. The effects of ablating the A and P axons upon the behavior of the G growth cone. J. Neurosci. 4, 2329–2345.

Saiki, R. K., Gelfand, D. H., Stoffel, S., Scharf, S. J., Higuchi, R., Horn, G. T., Mullis, K. B., and Ehrlich, H. A. (1988). Primer-directed enzymatic amplification of DNA with a thermostable DNA polymerase. Science 239, 487–494.

Sambrook, J., Fritsch, E. F., and Maniatis, T. (1989). Molecular Cloning: A Laboratory Manual (Cold Spring Harbor, New York: Cold Spring Harbor Laboratory).

Sanger, F., Nicklen, S., and Coulson, A. R. (1977). DNA sequencing with chain-terminating inhibitors. Proc. Natl. Acad. Sci. USA. 74, 5463–5467.

Schneider, I. (1972). Cell lines derived from late embryonic stages of *Drosophila melanogaster*. J. Embryol. Exp. Morphol. 27, 353–365.

Snow, P. M., Bieber, A. J., and Goodman, C. S. (1989). Fasciclin III: a novel homophilic adhesion molecule in Drosophila. Cell. 59, 313–323.

Snow, P. M., Zinn, K., Harrelson, A. L., McAllister, L., Schilling, J., Bastiani, M. J., Makk, G., and Goodman, C. S. (1988). Characterization and cloning of fasciclin I and fasciclin II glycoproteins in the grasshopper. Proc. Natl. Acad. Sci. USA 85, 5291–5295.

Spindler, K. R., Rosser, D. S., and Berk, A. J. (1984). Analysis of adenovirus transforming proteins from early regions 1A and 1B with antisera to inducible fusion antigens produced in *Escherichia coli*. J. Virol. 49, 132–141.

Wang, L., and Denburg, J. L. (1992). A role for proteoglycans in the guidance of a subset of pioneer axons in cultured embryos of the cockroach. (1992). Neuron. 8, 701–714.

Wang, L. S., Feng, Y., and Denburg, J. L. (1992). A multifunctional cell surface developmental stage-specific antigen in the cockroach embryo: involvement in pathfinding by CNS pioneer axons. J. Cell Biol. 118, 163–176.

Zinn, K., McAllister, L., and Goodman, C. S. (1988). Sequence analysis and neuronal expression of fasciclin I in grasshopper and Drosophila. Cell. 53, 577–587.

Genbank Accession Number

The accession number for the sequence reported in this paper is L00709.

II. Isolation and characterization of Tribolium (SEQ ID NOS:63 and 64) and Drosophila (SEQ ID NOS:59 and 60) Semaphorin I. Drosophila Semaphorin II. (SEQ ID NOS:61 and 62) Human Semaphorin III (SEQ ID NOS:53 and 54) and Vaccinia Virus Semaphorin IV (SEQ ID NOS:55 and 56) and Variola Major (smallpox) Virus Semaphorin V (SEQ ID NOS:67 and 68).

We used our G-Semaphorin I cDNA in standard low stringency screening methods (of both cDNA and genomic libraries) in an attempt to isolate a potential Semaphorin I homologue from Drosophila. We were unsuccessful in these screens. Since the sequence was novel and shared no similarity to anything else in the data base, we then attempted to see if we could identify a Semaphorin I homologue in other, more closely related insects. If possible, we would then compare these sequences to find the most conserved regions, and then to use probes (i.e., oligonucleotide primers for PCR) based on these conserved regions to find a Drosophila homologue.

In the process, we used the G-Semaphorin I cDNA in low stringency screens to clone Semaphorin I cDNAs from libraries made from locust *Locusta migratoria* embryonic RNA and from a cDNA embryonic library from the cricket *Acheta domestica*. We used PCR to clone genomic fragments from genomic DNA in the beetle Tribolium, and from the moth Manduca. We then used the Tribolium genomic DNA fragment to isolate cDNA clones and ultimately sequenced the complete ORF for the Tribolium cDNA.

In the meantime, we used the partial Tribolium and Manduca sequences in combination with the complete grasshopper sequence to identify conserved regions that allowed us to design primers for PCR in an attempt to clone a Drosophila Semaphorin I homologue. Several pairs of primers generated several different bands, which were subcloned and sequenced and several of the bands gave partial sequences of the Drosophila Semaphorin homologue. One of the bands gave a partial sequence of what was clearly a different, more divergent gene, which we call D-Semaphorin II.

Based on the sequence of PCR products, we knew we had identified two different Drosophila genes, one of which appeared to be the Semaphorin I homologue, and the other a second related gene. The complete ORF sequence of the D-Semaphorin I homologue revealed an overall structure identical to G-Semaphorin I: a signal sequence, an extracellular domain of around 550 amino acids containing 16 cysteines, a transmembrane domain of 25 amino acids, and a cytoplasmic domain of 117 amino acids. When we had finished the sequence for D-Semaphorin II, we were able to begin to run homology searches in the data base, which revealed some of its structural features further described herein. The Semaphorin II sequence revealed a different structure: a signal sequence of 16 amino acids, a ~525 amino acid domain containing 16 cysteines, with a single immunoglobulin (Ig) domain of 66 amino acids, followed by a short unique region of 73 amino acids. There is no evidence for either a transmembrane domain or a potential phospholipid linkage in the C-terminus of this protein. Thus, it appears that the D-Semaphorin II protein is secreted from the cells that produce it. The grasshopper, Tribolium, and Drosophila Semaphorin I cDNA sequences, as well as the sequence of the D-Semaphorin II cDNA, are shown herein. In addition, we used this same technique to identify Semaphorin I genes in a moth, Manduca sexta, a locust, *Locusta migratoria*, and a cricket, *Acheta domestica*.

With this large family of insect Semaphorin genes, we identified a number of good stretches of the right amino acids (with the least degeneracy based on their codons) with strong homology for designing primers for PCR to look for human genes. We designed a set of oligonucleotide primers, and plated out several human cDNA libraries: a fetal brain library (Stratagene), and an adult hippocampus library. We ultimately obtained a human cDNA PCR bands of the right size that did not autoprime and thus were good candidates to be bonafide Semaphorin-like cDNAs from humans. These bands were purified, subcloned, and sequenced.

Whole-mount in situ hybridization experiments showed that D-Semaphorin I and II are expressed by different subsets of neurons in the embryonic CNS. D-Semaphorin I is expressed by certain cells along the midline as well as by other neurons, whereas D-Semaphorin II is not expressed at the midline, but is expressed by a different subset of neurons. In addition, D-Semaphorin II is expressed by a subset of muscles prior to and during the period of innervation by specific motoneuron. On the polytene chromosomes, the D-Semaphorin I gene maps to (gene-band-chromosome)

29E1-22L and that of D-Semaphorin II to 53C9-102R. We have identified loss of function mutations in the D-Semaphorin I gene and a pair of P-element transposon insertions in the D-Semaphorin II gene which appear to cause severe phenotypes.

When we lined up the G-Semaphorin I, T-Semaphorin I, D-Semaphorin I, and D-Semaphorin II sequences and ran the sequences through a sequence data base in search of other sequences with significant similarity, we discovered a curious finding: these Semaphorins share sequence similarity with the A39R open reading frame (ORF) from Vaccinia virus and the A43R ORF from Variola Major (smallpox) virus and we discovered that the amino acids shared with the virus ORF were in the same regions where the insect proteins shared their greatest similarity. The viral ORF began with a putative signal sequence, continued for several hundred amino acids with sequence similarity to the Semaphorin genes, and then ended without any membrane linkage signal (suggesting that the protein as made by the infected cell would likely be secreted).

We reasoned that the virus semaphorins were appropriated host proteins advantageously exploited by the viruses, which would have host counterparts that most likely function in the immune system to inhibit or decrease an immune response, just as in the nervous system they appear to function by inhibiting growth cone extension. Analogous to situations where viruses are thought to encode a secreted form of a host cellular receptor, here the virus may cause the infected cell to make a lot of the secreted ligand to mimic an inhibitory signal and thus help decrease the immune response.

III. Isolation and characterization of Murine CNS Semaphorin III Receptor using Epitope Tagged Human Semaphorin III (hsIII)

mRNA was isolated from murine fetal brain tissue and used to construct a cDNA library in a mammalian expression vector, pCMX, essentially as in Davis et al. (1991) Science 253, 59.

The transfection and screening procedure is modified from Lin et al (1992) Cell 68, 775. COS cells grown on glass slide flaskettes are transfected with pools of the cDNA clones, allowed to bind radioiodinated hSIII truncated at the C-terminus end of the semaphorin domain. In parallel, similarly treated COS cells are allowed to bind unlabelled human semaphorin III truncated at the C-terminus end of the semaphorin domain and there joined to a 10-amino acid extension derived from the human c-myc proto-oncogene product. This modified hSIII allows the identification of hSIII receptors with the use of the tagged ligand as a bridge between the receptor and a murine monoclonal antibody which is specific for an epitope in the c-myc tag. Accordingly, after binding unlabelled hSIII the cells are exposed to the monoclonal which may be labeled directly or subsequently decorated with a secondary anti-mouse labeled antibody for enhanced signal amplification.

Cells are then fixed and screened using dark-field microscopy essentially as in Lin et al. (supra). Positive clones are identified and sequence analysis of murine CNS Semphorin III receptor cDNA clones by the dideoxy chain termination method is used to construct full-length receptor coding sequences.

It is evident from the above results that one can use the methods and compositions disclosed herein for making and identifying diagnostic probes and therapeutic drugs. It will also be clear to one skilled in the art from a reading of this disclosure that advantage can be taken to effect alterations of semaphorin responsiveness in a host.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

Deduced amino-acid sequence of semaphorin gene family.
Approximate position of enumerated peptide classes are indicated by parenthetical (a) through (o); semaphorin domains are bounded by arrows; G: grasshopper semaphorin I (SEQ ID NO:58), T: Tribolium semaphorin I (SEQ ID NO:64), D1: Drosophila semaphorin I (SEQ ID NO:60), D2: Drosophila semaphorin II (SEQ ID NO:62), H3: Human semaphorin I (SEQ ID NO:54), V4: Vaccinia virus semaphorin IV (SEQ ID NO:56), V5: Variola virus (human small pox) semaphorin IV (SEQ ID NO:66); small case residues: conserved residues; underline: signal sequence; solid bar: transmembrane domain; double dashes: immunoglobulin domain.

```
G                              MR AAL VAV AAL L WV V AL HAAA WV N D V S P KMY VQF GE E R VQR
T                                 MV VKI L VWS I CLI AL CHA WMP DS S S KLI NHF KS VE S KS
D1
D2  MS L LQL S P LL AL L L L L CS S VS E T A A D Y E N T WNF Y Y E R P CCT GNDQGNNNY GKHGADH VRE
H3                         MG WL T RI VCL F WG V L L T AR AN YQNGKNN VP RL KL S Y KE ML E S NN VI T
V4                                    MMVL L HAV YS I VF V D VI I I KV QR YI NDI

↓
G   f - L g - - n E S HKDHf KLLe KDHNS l Lv g a - - r NI - - - VYn I S LRDLTE F TE QRi E wGS s GAHREL c Y
T   f T - g - - n AT F P DHf I VLNQDE TS I Lv g G - - r NR - - - VYn LS I F DLS E RKGGRi DwP S s DAHGOL c I
D1
D2  f NCg KLY - - - YRTf HMNe DRDT - l Yv g a MDr VF - - - RVn LQNI S S S NCNRDAi NLE P TRDDVVS c V
H3  f N - g LAn S S S YHTf LLDe ERS R - l Yv g a KDHI F S F DL Vn I - - - - - - - KDF QKi VwP Vs YTRRDE c K
V4  LTLDI F YL F KKMI P LL F I L F YF ANGI E WHKF E TS E EI I S TYLLDDV - - - - - - L YT G VNGAVYTF S N
```

TABLE 1-continued

Deduced amino-acid sequence of semaphorin gene family.
Approximate position of enumerated peptide classes are indicated by parenthetical (a) through (o); semaphorin domains are bounded by arrows; G: grasshopper semaphorin I (SEQ ID NO:58), T: Tribolium semaphorin I (SEQ ID NO:64), D1: Drosophila semaphorin I (SEQ ID NO:60), D2: Drosophila semaphorin II (SEQ ID NO:62), H3: Human semaphorin I (SEQ ID NO:54), V4: Vaccinia virus semaphorin IV (SEQ ID NO:56), V5: Variola virus (human small pox) semaphorin IV (SEQ ID NO:66); small case residues: conserved residues; underline: signal sequence; solid bar: transmembrane domain; double dashes: immunoglobulin domain.

```
                                                  A
            F                                     V
        DDCQN- YI R(a)                   I C G T N(b)
G   L k g k S - E d d c q n - y i r - - Vl AKI DDDr VLI c g t n a YKp Lc RHy ALKd - - - - - GDy VVe KE YEg Rg - - - -
T   L k g k T - Dd d c q n - y i r - - i l YS S E P GKl VI c g t n S YKp Lc RTy AF KE - - - - - GKy LVe KE VEg I g - - - -
D1          E d d c q n - y i r - - i  MVVP S P Gr l Fv c g t n S FRp Mc NTy I I Sd - - - - - S Ny TLe a TKNg QA - - - -
D2  S k g k S QI F d c Kn HVi Q - - S MDQGD - - r l Yv c g t n a HNp KDYVi YANL - - - - - THLP R S E YVI g Vg LGI A
H3  WAg k DI LKEc An - Fi K - - Vl KAYNQTHl YAc g t Ga FHp I c TYi EI GHP E DNI F KLE NS HF E Ng Rg - - - -
V4  Nk LNKTGLTNNn - y i TTS i KVE DADKDT Lv c g t n NGNp Kc WKi DGS d - - - - - - - - - - - - - - - - - - - -

S F                                         A
        CP YDP(c)                            T V A D F S G(d)
G   L c p F d p Dh - - - - - - - - - n s t AI YS Eg Q - - - - - - - l y s At v a d f s g Td p Li y r Gp l - - - - - - - - - - - - -
T   L c p y Np Eh - - - - - - - - - n s t s VS YNg Q - - - - - - - l F s At v a d f s g Gd p Li y r Ep Q - - - - - - - - - - - - -
D1  Vc p y d p Rh - - - - - - - - - n s t s VLADNE - - - - - - - l y s g t v a d f s g Sd p I i y r Ep l - - - - - - - - - - - - -
D2  Kc p y d p LD - - - - - - - - - n s t AI YVENGNP GGLP Gl y s g t Na Ef TKAd TVi Fr TDl YNTS AKRLE YKF
H3  KS p y d p KL - - - - - - - - - LTAs LLI Dg E - - - - - - - l y s Aa d f Mg Rd FAi Fr T - l GHHHP I RTE QHD
V4  - - - - d p Kh RGRGYAF YQn s KVTI I S HNGc YLS DI NI s KE GI KRWRRF DGP c GYDl - - - - - - - - - - - - -
V5                                                                         MI Yl - - - - - - - - - - -

N
        LNAP NF V(e)            (f)F F F RETA E YI NCGK(g)               (h) DKGG
G   - r t e RS d LkQ - l n a p n f v - NTME y Nd FI F f f f r e t a v e y i n c g k a i y s r v a r v c k Hd k g g
T   - r t e LS d LkQ - l n a p n f v - Ns VAy g d YI F f f Yr e t a v e y Mn c g k Vi y s r v a r v c k Dd k g g
D1  - Qt e QYd S LS - l n a p n f v - S s Ft Qg d Fv y f f f r e t a v e Fi n c g k a i y s r v a r v c k Wd k g g
D2  Kr t LKYd S k W- l DKp n f v - Gs FDI g E Yv y f f f r e t a v e y i n c g k a v y s r i a r v c k Kd Vg g
H3  - S RWLNd p k F - I Sa HLI S E S d NP E Dd k v y f f f r e Na I DGEHS g k a THAr i GQI c k n d F g g
V4  YT ADNVI p k DGl RGA - f v DKd Gt y - d k v y I Lf TDt I G - S KRI Vk I Py - - i a QMc L n d E g g
V5  YT ADNVI p k DGl QGA - f v DKd Gt y - d k v y I Lf TVt I G - S KRI Vk I Py - - i a QMc L n d E Cg

S S Y(i)             V
        P H      WI T F LKAR   NCS I P G(j)
G   p h QF - GDr wt s f l k S r l n c s Vp g Dy p f y f - - - n e i q s - - - t s d I I e g Ny GGQVE kl i y g v
T   p h Q- S RDr wt s f l k a r l n c s i p g E y p f y f - - - De i g s - - - t s d I v e g Ry Ns DDs kl i y g I
D1  p h RF - RNr wt s f l k S r l n c s i p g Dy p f y f - - - n e i q s - - - As NLv e g Qy Gs MS s kl i y g v
D2  KNL l - a h Nw At Yl k a r l n c s i S g E F p f y f - - - n e i q s - - - VYQL - - - - - P s DKs RF - FAT
H3  - h RS LVNKwt t f l k a r l I c s Vp g P NGI DTHf - De Lq - - - - - - d VF LMNF KDP KNP VVy g v
V4  p S S l S S h r wSt f l k VE l E c Di Dg RS YRQI I HS RTi KTDNDt I LYv F - - FDs P Ys k - - - - -
V5  p S S l S S h r wSt Ll k VE l E c Di Dg RS TS QI NHS KTi KQI MI RYYMYS LI Vl F QVTI MYLF Y

V
        GS AVC(k)                         NS NWLP V(l)           P RP GT CVND(m)
G   f t t p Vn S i Gg s a v c a f s mKS i LE S f Dg P f k e q E TMn s n wl Av P S LKv p e p r p g Qc v n d s r
T   L t t p Vn Ai Gg s a l c a y QmAd i Lr Vf E g S f k Hq E TI n s n wl p v P QNLv p e p r p g q c v Rd s r
D1  f Nt p S n S i P g s a v c a f ALQd i ADTf E g Qf k e q TGI n s n wl p v NNAKv p Dp r p g S c Hn d s r
D2  f t t S Tn GLI g s a v c S f HI NEi QAAf Ng Kf k e q S S S n s Awl p v LNS Rv p e p r p g Tc v n d TS
H3  f t t S S n I F Kg s a v c My s mS d VRRVf Lg p YAHRDGP n YQwVp - YQGRv p Yp r p g Tc - - P s K
V4  - - - - - - - - - s a Lc Ty s mNTi KQS f S TS KLe g - - - - - - - - - - YT KQLp S p Ap g I c LP AGK
V5  E YH

G   - - - - - - - - - Tl p d VS Vn f V- k S h Tl md E Av p a Ff TRp i l I r I s l Qy r f t Ki Av d Qq v Rt P Dg KAYd v Lf
T   - - - - - - - - I l p d KNVn f i - k Th S l mE D - v p a Lf GKp Vl Vr Va l Qy r f t Ai Tv d P q v Kt I NNQYLd v LY
D1  - - - - - - - - - Al p d P TLn f i - k Th S l md E Nv p a Ff S Qp i l Vr Ts TI y r f t Qi Av d Aq I Kt P Gg KTYd v I f
D2  - - - - - - - - - Nl p d TVLn f i - RS h P l md KAv NHE Hn Np VYYKRDl VP TK - LVVDKI RI DI LNQE YI - v YY
H3  TF GGF DS TKDl p d DVI Tf A - r s h P AmYNP v F P MNn Rp i VI KTDVNy Qf t Qi Vv d - Rv DAE Dg QY - d v Mf
V4  - - - - - - - - - VVp HTTF E Vi E KYNVl Dd I I Kp - LS n Qp i F E GP S GVKWF DI KE KE NE HRE YRI YFI KE NS

G   i g t d d g k v I k ALn S As F DS S DTv DS v VI e e LQv LP P GVp VKn l YVv r - - - - - - - Md g - - d
T   i g t d d g k v Lk Av n I P KRHAKALL YRKYRTS VHP HGA - - p VKQl KI AP - - - - - - - - - - - - G
D1  Vg t d Hg k I I k S v n AE s ADS ADKv TS v VI e e I Dv LTKS E p I Rn l EI v r TMQYDQP Kd g S Yd
D2  Vg t NLg RI Yk I v n GE s LS KLLDI F E v AP Ne AI QVMEI S QTR - - - - - - - - - - - - - - - - - -
H3  i g t d Vg Tv Lk Vv S I P KE TWY- DLE Ev LLe e MTv F RE P TAI S A - - - - - - - - - - - - MELS TK
V4  i YS F d Tk S KQTRS S QVDAE LF S v MVTS KP KFI ADI GI GVGMP QMKKI LKM*
```

TABLE 1-continued

Deduced amino-acid sequence of semaphorin gene family.
Approximate position of enumerated peptide classes are indicated by parenthetical (a) through (o); semaphorin domains are bounded by arrows; G: grasshopper semaphorin I (SEQ ID NO:58), T: Tribolium semaphorin I (SEQ ID NO:64), D1: Drosophila semaphorin I (SEQ ID NO:60), D2: Drosophila semaphorin II (SEQ ID NO:62), H3: Human semaphorin I (SEQ ID NO:54), V4: Vaccinia virus semaphorin IV (SEQ ID NO:56), V5: Variola virus (human small pox) semaphorin IV (SEQ ID NO:66); small case residues: conserved residues; underline: signal sequence; solid bar: transmembrane domain; double dashes: immunoglobulin domain.

```
                            DP YCAWD(n)
G   d S k l V V v S d D E i L A i K l  h r c GS d k I t  Nc Re c v S l  q d p y c a wd  NVE L Kc TAVg S p DwS AG
T   YGk V V V v GKDE i R L AN l  NHc AS - k - t  Rc KDc v E l  q d p Hc a wd  AKQNL c V S I  DT V T S Y - -
D1  d Gk l I i v Td S QVVA i Q l  h r c HNd k I t  Sc S e c v A l  q d p y c a wd  KI AGKc RS Hg Ap Rw- LE
D2  - KS l Yi GTd HR i KQ i D l  AMc - NRRYDNc F Rc v - - Rd p y c Gwd  KE ANTc RP Y - - - - - - - -
H3  QQQ l Yi GS T AG VAQLP l  h r c DI YG- KAc Ae c CLARd p y c a wd - - GS Ac S - - - RYFPTAK

↓

G   Kr RF I q N I S Lg EH- KAc GGRP QTE I  VAS P VP TQP T TKS S GDP VHS I  HQAE F Ep e i DNE i V I
T   - r F L I q d v VRg DD- NKc Ws P QTDKk T V I  KNKP S E VENE I  TNS I  DEKDLs  S d p L i  KTGLd D
D   ENYF Yq Nv ATg QH- AAc P s GK I NS k DANAGE GKGF RNDMDL LDS RRQ - - s Kd Qe i I DN i d K
D2  E LDLLg d v ANE T S - D I c Ds S VLKKk
H3  Rr T RRq d I RNg DP LTHc S DL HDNHH

G   GVd d S NV I P NT LAE I NHAGS KLP S S QEK l Pi y t a e t l Ti a I v TS CLGA l Vv g f I s g F LFS
T   DS d c DP VS ENS I GGc AV - - - - - - - - RQQ l V i y t a Gt l H i Vv v VVs i VG l  F SWLYs g LS VF
D   NFEd D - - - - - - - - - - - - - - - - - I I NAQy t Ve t l VMa v LAGs i F S l Lv g f F Tg YFCG

G   r r c RGE DY TDMp F p d QRHQL NRLTE AG l NADs P YLP P CANn k AA I n l v LNv - - - - - P p k N
T   AKF HS d - - - - S Qy p EAP F I EQHNHLE R l s ANQTGYLTP RAn k - AVn l v v Kv S S S TP Rp k K
D   r r c HKd EDDNL p y p d TE YE YF EQRQNV Ns F P s S CR I QQEP KLLP QVEE v T YAEP VLLp QP

KKTYI (o)
G   An GKNANs S AE NKP - - - - I Qk k t y i *
T   Dn LDVS KDLN I  AS DGTLQK I k k t y i *
D   P P P NKMHs P KNTL R KP P MHQMHQGP NS E RLF QF HV T AT T P S S R I  V VAT T S E HCV P T R *

D2                       - - - - - I V V T y g - - - Qs VH l Gc F Vk I P E V l  KNE Qv TwYHHS KDKG
H3                       GHS P E ER I I y g VENS s T F l Ec S P k S QRA l - - - - v YwQF QRRNE E
    ==============================

D2  r Ye I RYS P T KYi E T t E Rg l V V V s VNE Ad Gg Ry Dc h LGGS LL c S YN I  T VDAHRc TP P NKS N
H3  r Ke E - I RVDDH i I Rt DQg l LL Rs LQQKd S g Ny L c h AVEHGF I QT LLKV T LE V I  DT E HLE E
    =======================================

D2  DYQK I YS DWc HE F E KYKT AMKS WE KKQGQc S T RQNF S c NQHP NE I  F RKP NV *
H3  LLHKDDDGDS KT KE MS NS MT P S QKVWYRDF MQL I NHP NL NT MDE F c E QVWKRDRKQRRQ

H3  RP GHTP GNS NKHL QE NKKGRNRRT HE F E RAP RS V *
```

---

What is claimed is:

1. A method of modulating a nerve, immune, virally-infected or transformed cell function, said method comprising the step of:

contacting a nerve immunevirally-infected or transformed cell with an effective amount of a composition comprising an isolated semaphorin polypeptide comprising the amino acid sequence of SEQ ID NO:54, 56, 58, 60, 62 or 64, or a portion of said amino acid sequence, said portion sufficient to provide a semaphorin binding specificity and comprising a peptide sequence selected from the group consisting of SEQ ID NOS:1–52 and 67–100, with the proviso that said polypeptide is other than a natural vaccinia or variola major virus open reading frame translation product, whereby said polypeptide modulates a function of said cell.

2. A method according to claim 1, wherein said peptide sequence is selected from the group consisting of:

(a) [AspGlu]Cys[GlnLysArgAlaAsn]Asn[TyrPheVal]Ile (SEQ ID NO:1)

Cys[GlnLysArgAlaAsn]Asn[TyrPheVal]Ile[ArgLysGlnThr] (SEQ ID NO:2)

(b) CysGlyThr[AsnGly][AlaSerAsn][TyrPheHisGly][LysArgHisAsnGln] (SEQ ID NO:3)

CysGlyThr[AsnGly][AlaSerAsn]XaaXaaPro (SEQ ID NO:4)

CysGlyThr[AsnGly]XaaXaaXaaProXaa[CysAsp] (SEQ ID NO:5)

CysGlyThrXaaXaaXaaXaaProXaa[CysAsp]XaaXaa[TyrIle] (SEQ ID NO:6)

(c) [ArgIleGlnVal][GlyAla][LeuValLys][CysSer]Pro[PheTyr][AspAsn] (SEQ ID NO:7)

[CysSer]Pro[PheTyr][AspAsn]Pro[AspGluArgLys][HisLeuAsp] (SEQ ID NO:8)

GlyXaa[GlyAla]Xaa[CysSer]ProTyr[AspAsn]Pro (SEQ ID NO:9)

(d) Leu[PheTyr]Ser[GlyAla]Thr[ValAsnAla]Ala (SEQ ID NO:10)

Leu[PheTyr]SerXaaThrXaaAla[AspGlu][PheTyr] (SEQ ID NO:11)

[PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14)

PhePhe[PheTyr]ArgGlu[ThrAsn] (SEQ ID NO:15)

PhePheArgGlu[ThrAsn]Ala (SEQ ID NO:16)

Phe[PheTyr]ArgGlu[ThrAsn]Ala (SEQ ID NO:17)

TyrPhePhe[PheTyr]ArgGlu (SEQ ID NO:18)

[PheTyr]PhePhe[PheTyr]ArgGlu (SEQ ID NO:19)

[PheTyr][PheTyr][PheTyr]ArgGlu[ThrAsn]Ala (SEQ ID NO:20)

136

[IleVal][PheTyr]Phe[PheTyr][PheTyr]ArgGlu (SEQ ID NO:21)

Asp[LysPheTyr]Val[PheTyr][PheTyrIleLeu][PheTyrIleLeu][PheTyr] (SEQ ID NO:22)

[ValIle][PheTyr][PheTyrIleLeu][PheTyrIleLeu]Phe[ArgThr]Xaa[ThrAsn](SEQ ID NO:23)

[ValIle][PheTyr][PheTyrIleLeu][PheTyrIleLeu][PheTyr][ArgThr][GluAspVal][ThrAsn] (SEQ ID NO:24)

(g) Glu[PheTyr]IleAsn[CysSer]GlyLys (SEQ ID NO:25)

[PheTyr]IleAsnCysGlyLys[AlaValIle] (SEQ ID NO:26)

(h) Arg[ValIle][AlaGly][ArgGln][ValIle]CysLys (SEQ ID NO:27)

Arg[ValIle]Xaa[ArgGln][ValIle]CysXaaXaaAsp (SEQ ID NO:28)

GlyLys[ValAlaIle]XaaXaaXaaArg[ValAlaIle]XaaXaaXaaCysLys (SEQ ID NO:29)

(i) [ArgLysAsn]Trp[ThrAlaSer][ThrAlaSer][PheTyrLeu]Leu[LysArg] (SEQ ID NO:30)

[PheTyr]Leu[LysArg][AlaSer]ArgLeu[AsnIle]Cys (SEQ ID NO:31)

[AsnIle]CysSer[IleVal][ProSer]Gly (SEQ ID NO:32)

Trp[ThrAlaSer][ThrAlaSer][PheTyrLeu]LeuLys[AlaSerValIleLeu]XaaLeu (SEQ ID NO:33)

Trp[ThrAlaSer][ThrAlaSer]XaaLeuLysXaaXaaLeuXaaCys (SEQ ID NO:34)

TrpXaa[ThrSer]XaaLeuLysXaaXaaLeuXaaCys (SEQ ID NO:35)

(j) [PheTyr][PheTyr][AsnAsp]GluIleGlnSer (SEQ ID NO:36)

[PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38)

SerAla[ValIleLeu]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41)

[ValLeuIle]ProXaaPro[ArgAla]ProGlyXaaCys (SEQ ID NO:42)

Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44)

Pro[HisPheTyr]Cys[AlaGly]TrpAsp (SEQ ID NO:45)

AspProXaaCys[AlaGly]TrpAsp (SEQ ID NO:46)

CysXaaXaaXaaXaaAspProXaaCysXaaTrpAsp (SEQ ID NO:47)

CysXaaXaaXaaAspProXaaCysXaaTrpAsp (SEQ ID NO:48)

CysXaaXaaAspProXaaCysXaaTrpAsp (SEQ ID NO:49)

CysXaaXaaCysXaaXaaXaaXaaAspXaaXaaCysXaaTrpAsp (SEQ ID NO:50)

CysXaaXaaCysXaaXaaXaaAspXaaXaaCysXaaTrpAsp (SEQ ID NO: 51), and

CysXaaXaaCysXaaXaaAspXaaXaaCysXaaTrpAsp (SEQ ID NO:52).

3. A method according to claim 1, wherein said peptide sequence is selected from the group consisting of:
(a) AspCysGlnAsnTyrIle (SEQ ID NO:67)
(b) CysGlyThr[AsnGly][AlaSer]XaaXaaPro (SEQ ID NO:68)
(c) GlyXaa[SerCys]ProTyrAspPro (SEQ ID NO:69)
(d) LeuTyrSerGlyThr[ValAsnAla]Ala (SEQ ID NO:70)
(e) LeuAsnAlaProAsnPheVal (SEQ ID NO:71)
(f) [PheTyr]PhePhe[PheTyr]ArgGlu (SEQ ID NO:19)
(g) Glu[PheTyr]IleAsn[CysSer]GlyLys (SEQ ID NO:25)
(h) Arg[ValIle]AlaArgValCysLys (SEQ ID NO:72)
(i) Trp[ThrAla][ThrSer][PheTyr]LeuLys[AlaSer]ArgLeu (SEQ ID NO:73)
(j) ProPheTyrPhe[AsnAsp]GluIleGlnSer (SEQ ID NO:74)
(k) GlySerAlaValCysXaa[PheTyr] (SEQ ID NO:75)
(l) AsnSerAsnTrpLeu[ProAla]Val (SEQ ID NO:76)
(m) Pro[GluAsp]ProArgProGly[ThrGlnSer]Cys (SEQ ID NO:77), and
(n) AspProTyrCys[AlaGly]TrpAsp (SEQ ID NO:78).

4. A method according to claim 1, wherein said peptide sequence is selected from the group consisting of:
(a) [AspGlu]Cys[GlnLysArgAlaAsn]Asn[TyrPheVal]Ile (SEQ ID NO:01)
Cys[GlnLysArgAlaAsn]Asn[TyrPheVal]Ile[ArgLysGlnThr] (SEQ ID NO:02)
(b) CysGlyThr[AsnGly][AlaSer][TyrPheHisGly][LysArgHisAsnGln] (SEQ ID NO:79)
CysGlyThr[AsnGly][AlaSerAsn][TyrPheHis][LysArgHisAsnGln] (SEQ ID NO:80)
CysGlyThr[AsnGly][AlaSer]XaaXaaPro (SEQ ID NO:81)
(c) [ArgIleGlnVal][GlyAla][LeuValLys][CysSer]Pro[PheTyr][AspAsn] (SEQ ID NO:07)
[CysSer]Pro[PheTyr][AspAsn]Pro[AspGluArgLys][HisLeuAsp] (SEQ ID NO:08)
GlyXaa[GlyAla]Xaa[CysSer]ProTyr[AspAsn]Pro (SEQ ID NO:09)
(d) Leu[PheTyr]Ser[GlyAla]Thr[ValAsnAla]Ala (SEQ ID NO:10)
Leu[PheTyr]SerXaaThrXaaAla[AspGlu][PheTyr] (SEQ ID NO:11)
[PheTyr]Ser[GlyAla]Thr[ValAsnAla]Ala[AspGlu][PheTyr] (SEQ ID NO:12)
(e) Leu[AsnAsp][AlaLys]ProAsnPheVal (SEQ ID NO:13)
(f) PhePhePheArgGlu (SEQ ID NO:14)
PhePhe[PheTyr]ArgGlu[ThrAsn] (SEQ ID NO:15)
PhePheArgGlu[ThrAsn]Ala (SEQ ID NO:16)
Phe[PheTyr]ArgGlu[ThrAsn]Ala (SEQ ID NO:17)
TyrPhePhe[PheTyr]ArgGlu (SEQ ID NO:18)
[PheTyr]PhePhe[PheTyr]ArgGlu (SEQ ID NO:19)
[PheTyr][PheTyr][PheTyr]ArgGlu[ThrAsn]Ala (SEQ ID NO:20)
[IleVal][PheTyr]Phe[PheTyr][PheTyr]ArgGlu (SEQ ID NO:21)
Asp[LysPheTyr]Val[PheTyr][PheTyrLeu][PheTyrIleLeu][PheTyr] (SEQ ID NO:22)
Asp[LysPheTyr]Val[PheTyr][PheTyrIleLeu][PheTyrIle][PheTyr] (SEQ ID NO:82)
[ValIle][PheTyr][PheTyrLeu][PheTyrIleLeu]Phe[ArgThr]Xaa[ThrAsn] (SEQ ID NO:83)

[ValIle][PheTyr][PheTyrIleLeu][PheTyrIle]Phe[ArgThr]Xaa[ThrAsn] (SEQ ID NO:84)
[ValIle][PheTyr][PheTyrIleLeu][PheTyrIleLeu]PheArgXaa[ThrAsn] (SEQ ID NO:85)
[ValIle][PheTyr][PheTyrLeu][PheTyrIleLeu][PheTyr][ArgThr][GluAspVal][ThrAsn] (SEQ ID NO:86)
(g) Glu[PheTyr]IleAsn[CysSer]GlyLys (SEQ ID NO:25)
[PheTyr]IleAsnCysGlyLys[AlaValIle] (SEQ ID NO:26)
(h) Arg[ValIle][AlaGly][ArgGln][ValIle]CysLys (SEQ ID NO:27)
Arg[ValIle]Xaa[ArgGln][ValIle]CysXaaXaaAsp (SEQ ID NO:28)
GlyLys[ValAlaIle]XaaXaaXaaArg[ValAlaIle]XaaXaaXaaCysLys (SEQ ID NO:29)
(i) [ArgLysAsn]Trp[ThrAla][ThrAlaSer][PheTyrLeu]Leu[LysArg] (SEQ ID NO:87)
[PheTyr]Leu[LysArg][AlaSer]ArgLeu[AsnIle]Cys (SEQ ID NO:31)
[AsnIle]CysSer[IleVal][ProSer]Gly (SEQ ID NO:32)
Trp[ThrAla][ThrAlaSer][PheTyrLeu]LeuLys[AlaSerValIleLeu]XaaLeu (SEQ ID NO:88)
Trp[ThrAlaSer][ThrAlaSer][PheTyrLeu]LeuLys[AlaSerIleLeu]XaaLeu (SEQ ID NO:89)
Trp[ThrAla][ThrAlaSer]XaaLeuLysXaaXaaLeuXaaCys (SEQ ID NO:90)
(j) [PheTyr][PheTyr][AsnAsp]GluIleGlnSer (SEQ ID NO:36)
[PheTyr]Pro[PheTyr][PheTyr][PheTyr][AsnAsp]Glu (SEQ ID NO:37)
(k) GlySerAla[ValIleLeu]CysXaa[PheTyr] (SEQ ID NO:38)
SerAla[ValIle]CysXaa[PheTyr]XaaMet (SEQ ID NO:39)
(l) AsnSer[AsnAla]TrpLeu[ProAla]Val (SEQ ID NO:40)
(m) [ValLeuIle]Pro[GluAspTyrSerPhe]ProArgProGly (SEQ ID NO:41)
[ValLeuIle]ProXaaProArgProGlyXaaCys (SEQ ID NO:91)
Pro[GluAspTyrSerPhe]ProArgProGly[ThrGlnSer]Cys (SEQ ID NO:43)
(n) AspPro[HisPheTyr]Cys[AlaGly]Trp (SEQ ID NO:44)
Pro[HisPheTyr]Cys[AlaGly]TrpAsp (SEQ ID NO:45)
AspProXaaCys[AlaGly]TrpAsp (SEQ ID NO:46)
CysXaaXaaXaaXaaAspProXaaCysXaaTrpAsp (SEQ ID NO:47)
CysXaaXaaXaaAspProXaaCysXaaTrpAsp (SEQ ID NO:48)
CysXaaXaaAspProXaaCysXaaTrpAsp (SEQ ID NO:49)
CysXaaXaaCysXaaXaaXaaXaaAspXaaXaaCysXaaTrpAsp (SEQ ID NO:50)
CysXaaXaaCysXaaXaaXaaAspXaaXaaCysXaaTrpAsp (SEQ ID NO:51), and
CysXaaXaaCysXaaXaaAspXaaXaaCysXaaTrpAsp (SEQ ID NO:52).

5. A method according to claim 1, wherein said peptide sequence is selected from the group consisting of:
(f) TyrPhePhe[PheTyr]ArgGlu (SEQ ID NO:18)
Asp[LysTyr]Val[PheTyr][PheTyrLeu][PheTyrIleLeu][PheTyr] (SEQ ID NO:92)
Asp[LysTyr]Val[PheTyr][PheTyrIleLeu][PheTyrIle][PheTyr] (SEQ ID NO:93)
[ValIle]Tyr[PheTyrLeu][PheTyrIleLeu]Phe[ArgThr]Xaa[ThrAsn] (SEQ ID NO:94)
[ValIle]Tyr[PheTyrIleLeu][PheTyrIle]Phe[ArgThr]Xaa[ThrAsn] (SEQ ID NO:95)

[ValIle]Tyr[PheTyrIleLeu][PheTyrIleLeu]PheArgXaa [ThrAsn] (SEQ ID NO:96)

Val[PheTyr][PheTyrLeu][PheTyrIleLeu][PheTyr] [ArgThr][GluAspVal][ThrAsn] (SEQ ID NO:97)

Val[PheTyr][PheTyrIleLeu][PheTyrIle][PheTyr][ArgThr] [GluAspVal][ThrAsn] (SEQ ID NO:98)

Val[PheTyr][PheTyrIleLeu][PheTyrIleLeu][PheTyr]Arg [GluAspVal][ThrAsn] (SEQ ID NO:99)

(n) CysXaaXaaXaaAspProXaaCysXaaTrpAsp (SEQ ID NO:48)

CysXaaXaaAspProXaaCysXaaTrpAsp (SEQ ID NO:49)

CysXaaXaaCysXaaXaaXaaAspXaaXaaCysXaaTrpAsp (SEQ ID NO:51), and

CysXaaXaaCysXaaXaaAspXaaXaaCysXaaTrpAsp (SEQ ID NO:52).

6. A method according to claim 1, wherein said peptide sequence is selected from the group consisting of:

(b) CysGlyThr[AsnGly][AlaSerAsn][TyrPheHisGly][LysArgHisAsnGln] (SEQ ID NO:03)

CysGlyThr[AsnGly][AlaSerAsn]XaaXaaPro (SEQ ID NO:04)

CysGlyThr[AsnGly]XaaXaaXaaProXaa[CysAsp] (SEQ ID NO:05)

CysGlyThrXaaXaaXaaXaaProXaa[CysAsp]XaaXaa [TyrIle] (SEQ ID NO:06)

(f) Asp[LysPheTyr]Val[PheTyr][PheTyrIleLeu] [PheTyrIleLeu][PheTyr] (SEQ ID NO:22)

[ValIle][PheTyr][PheTyrIleLeu][PheTyrIleLeu]Phe [ArgThr]Xaa[ThrAsn] (SEQ ID NO:23)

Val[PheTyr][PheTyrIleLeu][PheTyrIleLeu][PheTyr] [ArgThr][GluAspVal][ThrAsn] (SEQ ID NO:100)

(i) [ArgLysAsn]Trp[ThrAlaSer][ThrAlaSer][PheTyrLeu] Leu[LysArg] (SEQ ID NO:30)

Trp[ThrAlaSer][ThrAlaSer][PheTyrLeu]LeuLys [AlaSerValIleLeu]XaaLeu (SEQ ID NO:33)

Trp[ThrAlaSer][ThrAlaSer] XaaLeuLysXaaXaaLeuXaaCys (SEQ ID NO:34)

TrpXaa[ThrSer]XaaLeuLysXaaXaaLeuXaaCys (SEQ ID NO:35)

(k) SerAla[ValIleLeu]CysXaa[PheTyr]XaaMet (SEQ ID NO:39), and (m) [ValLeuIle]ProXaaPro[ArgAla]ProGlyXaaCys (SEQ ID NO:42).

7. A method of modulating a nerve, immune, virally-infected or transformed cell function, said method comprising the step of:

contacting a nerve immune, virally-infected or transformed cell with an effective amount of a composition comprising an isolated polypeptide comprising the amino acid sequence of SEQ ID NO:54, 58, 60, 62, or 64; or a portion of said amino acid sequence, said portion sufficient to provide a semaphorin binding specificity and comprising a peptide sequence selected from the group consisting of SEQ ID NOS:1–52 and 67–100, and with the proviso that said peptide sequence is contained within neither SEQ ID NO:56 nor 66, whereby said polypeptide modulates a function of said cell.

8. A method according to claim 7, wherein said peptide sequence is selected from the group consisting of:

(a) [AspGlu]Cys[GlnLysArgAlaAsn]Asn[TyrPheVal]Ile (SEQ ID NO:1)

Cys[GlnLysArgAlaAsn]Asn[TyrPheVal]Ile [ArgLysGlnThr] (SEQ ID NO:2)

(b) CysGlyThr[AsnGly][AlaSerAsn][TyrPheHisGly] [LysArgHisAsnGln] (SEQ ID NO:3)

CysGlyThr[AsnGly][AlaSerAsn]XaaXaaPro (SEQ ID NO:4)

CysGlyThr[AsnGly]XaaXaaXaaProXaa[CysAsp] (SEQ ID NO:5)

CysGlyThrXaaXaaXaaXaaProXaa[CysAsp]XaaXaa [TyrIle] (SEQ ID NO:6)

(c) [ArgIleGlnVal][GlyAla][LeuValLys][CysSer]Pro [PheTyr][AspAsn] (SEQ ID NO:7)

[CysSer]Pro[PheTyr][AspAsn]Pro[AspGluArgLys] [HisLeuAsp] (SEQ ID NO:8)

GlyXaa[GlyAla]Xaa[CysSer]ProTyr[AspAsn]Pro (SEQ ID NO:9)

(d) Leu[PheTyr]Ser[GlyAla]Thr[ValAsnAla]Ala (SEQ ID NO:10)

Leu[PheTyr]SerXaaThrXaaAla[AspGlu][PheTyr] (SEQ ID NO:11)

[PheTyr]Ser[GlyAla]Thr[ValAsnAla]Ala[AspGlu] [PheTyr] (SEQ ID NO:12)

(e) Leu[AsnAsp][AlaLys]ProAsnPheVal (SEQ ID NO:13)

(f) PhePhePheArgGlu (SEQ ID NO:14)

PhePhe[PheTyr]ArgGlu[ThrAsn] (SEQ ID NO:15)

PhePheArgGlu[ThrAsn]Ala (SEQ ID NO:16)

Phe[PheTyr]ArgGlu[ThrAsn]Ala (SEQ ID NO:17)

TyrPhePhe[PheTyr]ArgGlu (SEQ ID NO:18)

[PheTyr]PhePhe[PheTyr]ArgGlu (SEQ ID NO:19)

[PheTyr][PheTyr][PheTyr]ArgGlu[ThrAsn]Ala (SEQ ID NO:20)

[IleVal][PheTyr]Phe[PheTyr][PheTyr]ArgGlu (SEQ ID NO:21)

Asp[LysPheTyr]Val[PheTyr][PheTyrIleLeu] [PheTyrIleLeu][PheTyr] (SEQ ID NO:22)

[ValIle][PheTyr][PheTyrIleLeu][PheTyrIleLeu]Phe [ArgThr]Xaa[ThrAsn](SEQ ID NO:23)

[ValIle][PheTyr][PheTyrIleLeu][PheTyrIleLeu][PheTyr] [ArgThr][GluAspVal][ThrAsn] (SEQ ID NO:24)

(g) Glu[PheTyr]IleAsn[CysSer]GlyLys (SEQ ID NO:25)

[PheTyr]IleAsnCysGlyLys[AlaValIle] (SEQ ID NO:26)

(h) Arg[ValIle][AlaGly][ArgGln][ValIle]CysLys (SEQ ID NO:27)

Arg[ValIle]Xaa[ArgGln][ValIle]CysXaaXaaAsp (SEQ ID NO:28)

GlyLys[ValAlaIle]XaaXaaXaaArg[ValAlaIle] XaaXaaXaaCysLys (SEQ ID NO:29)

(i) [ArgLysAsn]Trp[ThrAlaSer][ThrAlaSer][PheTyrLeu] Leu[LysArg] (SEQ ID NO:30)

[PheTyr]Leu[LysArg][AlaSer]ArgLeu[AsnIle]Cys (SEQ ID NO:31)

[AsnIle]CysSer[IleVal][ProSer]Gly (SEQ ID NO:32)

Trp[ThrAlaSer][ThrAlaSer][PheTyrLeu]LeuLys [AlaSerValIleLeu]XaaLeu (SEQ ID NO:33)

Trp[ThrAlaSer][ThrAlaSer] XaaLeuLysXaaXaaLeuXaaCys (SEQ ID NO:34)

TrpXaa[ThrSer]XaaLeuLysXaaXaaLeuXaaCys (SEQ ID NO:35)

(j) [PheTyr][PheTyr][AsnAsp]GluIleGlnSer (SEQ ID NO:36)

[PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38)

SerAla[ValIleLeu]CysXaa[PheTyr]XaaMet (SEQ ID NO:39)

(l) AsnSer[AsnAla]TrpLeu[ProAla]Val (SEQ ID NO:40)
(m) [ValLeuIle]Pro[GluAspTyrSerPhe]ProArgProGly (SEQ ID NO:41)
[ValLeuIle]ProXaaPro[ArgAla]ProGlyXaaCys (SEQ ID NO:42)
Pro[GluAspTyrSerPhe]ProArgProGly[ThrGlnSer]Cys (SEQ ID NO:43)
(n) AspPro[HisPheTyr]Cys[AlaGly]Trp (SEQ ID NO:44)
Pro[HisPheTyr]Cys[AlaGly]TrpAsp (SEQ ID NO:45)
AspProXaaCys[AlaGly]TrpAsp (SEQ ID NO:46)
CysXaaXaaXaaXaaAspProXaaCysXaaTrpAsp (SEQ ID NO:47)
CysXaaXaaXaaAspProXaaCysXaaTrpAsp (SEQ ID NO:48)
CysXaaXaaAspProXaaCysXaaTrpAsp (SEQ ID NO:49)
CysXaaXaaCysXaaXaaXaaXaaAspXaaXaaCysXaaTrpAsp (SEQ ID NO:50)
CysXaaXaaCysXaaXaaXaaAspXaaXaaCysXaaTrpAsp (SEQ ID NO:51), and
CysXaaXaaCysXaaXaaAspXaaXaaCysXaaTrpAsp (SEQ ID NO:52).

9. A method according to claim 7, wherein said peptide sequence is selected from the group consisting of:
(a) AspCysGlnAsnTyrIle (SEQ ID NO:67)
(b) CysGlyThr[AsnGly][AlaSer]XaaXaaPro (SEQ ID NO:68)
(c) GlyXaa[SerCys]ProTyrAspPro (SEQ ID NO:69)
(d) LeuTyrSerGlyThr[ValAsnAla]Ala (SEQ ID NO:70)
(e) LeuAsnAlaProAsnPheVal (SEQ ID NO:71)
(f) [PheTyr]PhePhe[PheTyr]ArgGlu (SEQ ID NO:19)
(g) Glu[PheTyr]IleAsn[CysSer]GlyLys (SEQ ID NO:25)
(h) Arg[ValIle]AlaArgValCysLys (SEQ ID NO:72)
(i) Trp[ThrAla][ThrSer][PheTyr]LeuLys[AlaSer]ArgLeu (SEQ ID NO:73)
(j) ProPheTyrPhe[AsnAsp]GluIleGlnSer (SEQ ID NO:74)
(k) GlySerAlaValCysXaa[PheTyr] (SEQ ID NO:75)
(l) AsnSerAsnTrpLeu[ProAla]Val (SEQ ID NO:76)
(m) Pro[GluAsp]ProArgProGly[ThrGlnSer]Cys (SEQ ID NO:77), and
(n) AspProTyrCys[AlaGly]TrpAsp (SEQ ID NO:78).

10. A method according to claim 7, wherein said peptide sequence is selected from the group consisting of:
(a) [AspGlu]Cys[GlnLysArgAlaAsn]Asn[TyrPheVal]Ile (SEQ ID NO:01)
Cys[GlnLysArgAlaAsn]Asn[TyrPheVal]Ile[ArgLysGlnThr] (SEQ ID NO:02)
(b) CysGlyThr[AsnGly][AlaSer][TyrPheHisGly][LysArgHisAsnGln] (SEQ ID NO:79)
CysGlyThr[AsnGly][AlaSerAsn][TyrPheHis][LysArgHisAsnGln] (SEQ ID NO:80)
CysGlyThr[AsnGly][AlaSer]XaaXaaPro (SEQ ID NO:81)
(c) [ArgIleGlnVal][GlyAla][LeuValLys][CysSer]Pro[PheTyr][AspAsn] (SEQ ID NO:07)
[CysSer]Pro[PheTyr][AspAsn]Pro[AspGluArgLys][HisLeuAsp] (SEQ ID NO:08)
GlyXaa[GlyAla]Xaa[CysSer]ProTyr[AspAsn]Pro (SEQ ID NO:09)
(d) Leu[PheTyr]Ser[GlyAla]Thr[ValAsnAla]Ala (SEQ ID NO:10)
Leu[PheTyr]SerXaaThrXaaAla[AspGlu][PheTyr] (SEQ ID NO:11)
[PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)
(f) PhePhePheArgGlu (SEQ ID NO:14)
PhePhe[PheTyr]ArgGlu[ThrAsn] (SEQ ID NO:15)
PhePheArgGlu[ThrAsn]Ala (SEQ ID NO:16)
Phe[PheTyr]ArgGlu[ThrAsn]Ala (SEQ ID NO:17)
TyrPhePhe[PheTyr]ArgGlu (SEQ ID NO:18)
[PheTyr]PhePhe[PheTyr]ArgGlu (SEQ ID NO:19)
[PheTyr][PheTyr][PheTyr]ArgGlu[ThrAsn]Ala (SEQ ID NO:20)
[IleVal][PheTyr]Phe[PheTyr][PheTyr]ArgGlu (SEQ ID NO:21)
Asp[LysPheTyr]Val[PheTyr][PheTyrLeu][PheTyrIleLeu][PheTyr] (SEQ ID NO:22)
Asp[LysPheTyr]Val[PheTyr][PheTyrIleLeu][PheTyrIle][PheTyr] (SEQ ID NO:82)
[ValIle][PheTyr][PheTyrLeu][PheTyrIleLeu]Phe[ArgThr]Xaa[ThrAsn] (SEQ ID NO:83)
[ValIle][PheTyr][PheTyrIleLeu][PheTyrIle]Phe[ArgThr]Xaa[ThrAsn] (SEQ ID NO:84)
[ValIle][PheTyr][PheTyrIleLeu][PheTyrIleLeu]PheArgXaa[ThrAsn] (SEQ ID NO:85)
[ValIle][PheTyr][PheTyrLeu][PheTyrIleLeu][PheTyr][ArgThr][GluAspVal][ThrAsn] (SEQ ID NO:86)
(g) Glu[PheTyr]IleAsn[CysSer]GlyLys (SEQ ID NO:25)
[PheTyr]IleAsnCysGlyLys[AlaValIle] (SEQ ID NO:26)
(h) Arg[ValIle][AlaGly][ArgGln][ValIle]CysLys (SEQ ID NO:27)
Arg[ValIle]Xaa[ArgGln][ValIle]CysXaaXaaAsp (SEQ ID NO:28)
GlyLys[ValAlaIle]XaaXaaXaaArg[ValAlaIle]XaaXaaXaaCysLys (SEQ ID NO:29)
(i) [ArgLysAsn]Trp[ThrAla][ThrAlaSer][PheTyrLeu]Leu[LysArg] (SEQ ID NO:87)
[PheTyr]Leu[LysArg][AlaSer]ArgLeu[AsnIle]Cys (SEQ ID NO:31)
[AsnIle]CysSer[IleVal][ProSer]Gly (SEQ ID NO:32)
Trp[ThrAla][ThrAlaSer][PheTyrLeu]LeuLys[AlaSerValIleLeu]XaaLeu (SEQ ID NO:88)
Trp[ThrAlaSer][ThrAlaSer][PheTyrLeu]LeuLys[AlaSerIleLeu]XaaLeu (SEQ ID NO:89)
Trp[ThrAla][ThrAlaSer]XaaLeuLysXaaXaaLeuXaaCys (SEQ ID NO:90)
(j) [PheTyr][PheTyr][AsnAsp]GluIleGlnSer (SEQ ID NO:36)
[PheTyr]Pro[PheTyr][PheTyr][PheTyr][AsnAsp]Glu (SEQ ID NO:37)
(k) GlySerAla[ValIleLeu]CysXaa[PheTyr] (SEQ ID NO:38)
SerAla[ValIle]CysXaa[PheTyr]XaaMet (SEQ ID NO:39)
(l) AsnSer[AsnAla]TrpLeu[ProAla]Val (SEQ ID NO:40)
(m) [ValLeuIle]Pro[GluAspTyrSerPhe]ProArgProGly (SEQ ID NO:41)
[ValLeuIle]ProXaaProArgProGlyXaaCys (SEQ ID NO:91)
Pro[GluAspTyrSerPhe]ProArgProGly[ThrGlnSer]Cys (SEQ ID NO:43)
(n) AspPro[HisPheTyr]Cys[AlaGly]Trp (SEQ ID NO:44)
Pro[HisPheTyr]Cys[AlaGly]TrpAsp (SEQ ID NO:45)
AspProXaaCys[AlaGly]TrpAsp (SEQ ID NO:46)
CysXaaXaaXaaXaaAspProXaaCysXaaTrpAsp (SEQ ID NO:47)
CysXaaXaaXaaAspProXaaCysXaaTrpAsp (SEQ ID NO:48)

CysXaaXaaAspProXaaCysXaaTrpAsp (SEQ ID NO:49)

CysXaaXaaCysXaaXaaXaaXaaAspXaaXaaCysXaaTrpAsp (SEQ ID NO:50)

CysXaaXaaCysXaaXaaXaaAspXaaXaaCysXaaTrpAsp (SEQ ID NO:51), and

CysXaaXaaCysXaaXaaAspXaaXaaCysXaaTrpAsp (SEQ ID NO:52).

11. A method according to claim 7, wherein said peptide sequence is selected from the group consisting of:
(f) TyrPhePhe[PheTyr]ArgGlu (SEQ ID NO:18)

Asp[LysTyr]Val[PheTyr][PheTyrLeu][PheTyrIleLeu][PheTyr] (SEQ ID NO:92)

Asp[LysTyr]Val[PheTyr][PheTyrIleLeu][PheTyrIle][PheTyr] (SEQ ID NO:93)

[ValIle]Tyr[PheTyrLeu][PheTyrIleLeu]Phe[ArgThr]Xaa[ThrAsn] (SEQ ID NO:94)

[ValIle]Tyr[PheTyrIleLeu][PheTyrIle]Phe[ArgThr]Xaa[ThrAsn] (SEQ ID NO:95)

[ValIle]Tyr[PheTyrIleLeu][PheTyrIleLeu]PheArgXaa[ThrAsn] (SEQ ID NO:96)

Val[PheTyr][PheTyrLeu][PheTyrIleLeu][PheTyr][ArgThr][GluAspVal][ThrAsn] (SEQ ID NO:97)

Val[PheTyr][PheTyrIleLeu][PheTyrIle][PheTyr][ArgThr][GluAspVal][ThrAsn] (SEQ ID NO:98)

Val[PheTyr][PheTyrIleLeu][PheTyrIleLeu][PheTyr]Arg[GluAspVal][ThrAsn] (SEQ ID NO:99)

(n) CysXaaXaaXaaAspProXaaCysXaaTrpAsp (SEQ ID NO:48)

CysXaaXaaAspProXaaCysXaaTrpAsp (SEQ ID NO:49)

CysXaaXaaCysXaaXaaXaaAspXaaXaaCysXaaTrpAsp (SEQ ID NO:51), and

CysXaaXaaCysXaaXaaAspXaaXaaCysXaaTrpAsp (SEQ ID NO:52).

12. A method of modulating a nerve, immune, virally-infected or transformed cell function, said method comprising the step of:

contacting a nerve, immune, virally-infected or transformed cell with an effective amount of a composition comprising an isolated semaphorin polypeptide comprising the amino acid sequence of SEQ ID NO:54, 58, 60, 62, or 64; or a portion of said amino acid sequence, said portion sufficient to provide a semaphorin binding specificity and comprising a peptide sequence selected from the group consisting of SEQ ID NOS:1–52 and 67–100, and with the proviso that said peptide sequence is other than a sequence occurring in a natural vaccinia or variola major virus open reading frame translation product, whereby said polypeptide modulates a function of said cell.

13. A method according to claim 12, wherein said peptide sequence is selected from the group consisting of:
(a) [AspGlu]Cys[GlnLysArgAlaAsn]Asn[TyrPheVal]Ile (SEQ ID NO:1)

Cys[GlnLysArgAlaAsn]Asn[TyrPheVal]Ile[ArgLysGlnThr] (SEQ ID NO:2)

(b) CysGlyThr[AsnGly][AlaSerAsn][TyrPheHisGly][LysArgHisAsnGln] (SEQ ID NO:3)

CysGlyThr[AsnGly][AlaSerAsn]XaaXaaPro (SEQ ID NO:4)

CysGlyThr[AsnGly]XaaXaaXaaProXaa[CysAsp] (SEQ ID NO:5)

CysGlyThrXaaXaaXaaXaaProXaa[CysAsp]XaaXaa[TyrIle] (SEQ ID NO:6)

(c) [ArgIleGlnVal][GlyAla][LeuValLys][CysSer]Pro[PheTyr][AspAsn] (SEQ ID NO:7)

[CysSer]Pro[PheTyr][AspAsn]Pro[AspGluArgLys][HisLeuAsp] (SEQ ID NO:8)

GlyXaa[GlyAla]Xaa[CysSer]ProTyr[AspAsn]Pro (SEQ ID NO:9)

(d) Leu[PheTyr]Ser[GlyAla]Thr[ValAsnAla]Ala (SEQ ID NO:10)

Leu[PheTyr]SerXaaThrXaaAla[AspGlu][PheTyr] (SEQ ID NO:11)

[PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14)

PhePhe[PheTyr]ArgGlu[ThrAsn] (SEQ ID NO:15)

PhePheArgGlu[ThrAsn]Ala (SEQ ID NO:16)

Phe[PheTyr]ArgGlu[ThrAsn]Ala (SEQ ID NO:17)

TyrPhePhe[PheTyr]ArgGlu (SEQ ID NO:18)

[PheTyr]PhePhe[PheTyr]ArgGlu (SEQ ID NO:19)

[PheTyr][PheTyr][PheTyr]ArgGlu[ThrAsn]Ala (SEQ ID NO:20)

[IleVal][PheTyr]Phe[PheTyr][PheTyr]ArgGlu (SEQ ID NO:21)

Asp[LysPheTyr]Val[PheTyr][PheTyrIleLeu][PheTyrIleLeu][PheTyr] (SEQ ID NO:22)

[ValIle][PheTyr][PheTyrIleLeu][PheTyrIleLeu]Phe[ArgThr]Xaa[ThrAsn](SEQ ID NO:23)

[ValIle][PheTyr][PheTyrIleLeu][PheTyrIleLeu][PheTyr][ArgThr][GluAspVal][ThrAsn] (SEQ ID NO:24)

(g) Glu[PheTyr]IleAsn[CysSer]GlyLys (SEQ ID NO:25)

[PheTyr]IleAsnCysGlyLys[AlaValIle] (SEQ ID NO:26)

(h) Arg[ValIle][AlaGly][ArgGln][ValIle]CysLys (SEQ ID NO:27)

Arg[ValIle]Xaa[ArgGln][ValIle]CysXaaXaaAsp (SEQ ID NO:28)

GlyLys[ValAlaIle]XaaXaaXaaArg[ValAlaIle]XaaXaaXaaCysLys (SEQ ID NO:29)

(i) [ArgLysAsn]Trp[ThrAlaSer][ThrAlaSer][PheTyrLeu]Leu[LysArg] (SEQ ID NO:30)

[PheTyr]Leu[LysArg][AlaSer]ArgLeu[AsnIle]Cys (SEQ ID NO:31)

[AsnIle]CysSer[IleVal][ProSer]Gly (SEQ ID NO:32)

Trp[ThrAlaSer][ThrAlaSer][PheTyrLeu]LeuLys[AlaSerValIleLeu]XaaLeu (SEQ ID NO:33)

Trp[ThrAlaSer][ThrAlaSer]XaaLeuLysXaaXaaLeuXaaCys (SEQ ID NO:34)

TrpXaa[ThrSer]XaaLeuLysXaaXaaLeuXaaCys (SEQ ID NO:35)

(j) [PheTyr][PheTyr][AsnAsp]GluIleGlnSer (SEQ ID NO:36)

[PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38)

SerAla[ValIleLeu]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41)

[ValLeuIle]ProXaaPro[ArgAla]ProGlyXaaCys (SEQ ID NO:42)

Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44)
Pro[HisPheTyr]Cys[AlaGly]TrpAsp (SEQ ID NO:45)
AspProXaaCys[AlaGly]TrpAsp (SEQ ID NO:46)
CysXaaXaaXaaXaaAspProXaaCysXaaTrpAsp (SEQ ID NO:47)
CysXaaXaaXaaAspProXaaCysXaaTrpAsp (SEQ ID NO:48)
CysXaaXaaAspProXaaCysXaaTrpAsp (SEQ ID NO:49)
CysXaaXaaCysXaaXaaXaaXaaAspXaaXaaCysXaaTrpAsp (SEQ ID NO:50)
CysXaaXaaCysXaaXaaXaaAspXaaXaaCysXaaTrpAsp (SEQ ID NO:51), and
CysXaaXaaCysXaaXaaAspXaaXaaCysXaaTrpAsp (SEQ ID NO:52).

14. A method according to claim 12, wherein said peptide sequence is selected from the group consisting of:
(a) AspCysGlnAsnTyrIle (SEQ ID NO:67)
(b) CysGlyThr[AsnGly][AlaSer]XaaXaaPro (SEQ ID NO:68)
(c) GlyXaa[SerCys]ProTyrAspPro (SEQ ID NO:69)
(d) LeuTyrSerGlyThr[ValAsnAla]Ala (SEQ ID NO:70)
(e) LeuAsnAlaProAsnPheVal (SEQ ID NO:71)
(f) [PheTyr]PhePhe[PheTyr]ArgGlu (SEQ ID NO:19)
(g) Glu[PheTyr]IleAsn[CysSer]GlyLys (SEQ ID NO:25)
(h) Arg[ValIle]AlaArgValCysLys (SEQ ID NO:72)
(i) Trp[ThrAla][ThrSer][PheTyr]LeuLys[AlaSer]ArgLeu (SEQ ID NO:73)
(j) ProPheTyrPhe[AsnAsp]GluIleGlnSer (SEQ ID NO:74)
(k) GlySerAlaValCysXaa[PheTyr] (SEQ ID NO:75)
(l) AsnSerAsnTrpLeu[ProAla]Val (SEQ ID NO:76)
(m) Pro[GluAsp]ProArgProGly[ThrGlnSer]Cys (SEQ ID NO:77), and
(n) AspProTyrCys[AlaGly]TrpAsp (SEQ ID NO:78).

15. A method according to claim 12, wherein said peptide sequence is selected from the group consisting of:
(a) [AspGlu]Cys[GlnLysArgAlaAsn]Asn[TyrPheVal]Ile (SEQ ID NO:01)
Cys[GlnLysArgAlaAsn]Asn[TyrPheVal]Ile[ArgLysGlnThr] (SEQ ID NO:02)
(b) CysGlyThr[AsnGly][AlaSer][TyrPheHisGly][LysArgHisAsnGln] (SEQ ID NO:79)
CysGlyThr[AsnGly][AlaSerAsn][TyrPheHis][LysArgHisAsnGln] (SEQ ID NO:80)
CysGlyThr[AsnGly][AlaSer]XaaXaaPro (SEQ ID NO:81)
(c) [ArgIleGlnVal][GlyAla][LeuValLys][CysSer]Pro[PheTyr][AspAsn] (SEQ ID NO:07)
[CysSer]Pro[PheTyr][AspAsn]Pro[AspGluArgLys][HisLeuAsp] (SEQ ID NO:08)
GlyXaa[GlyAla]Xaa[CysSer]ProTyr[AspAsn]Pro (SEQ ID NO:09)
(d) Leu[PheTyr]Ser[GlyAla]Thr[ValAsnAla]Ala (SEQ ID NO:10)
Leu[PheTyr]SerXaaThrXaaAla[AspGlu][PheTyr] (SEQ ID NO:11)
[PheTyr]Ser[GlyAla]Thr[ValAsnAla]Ala[AspGlu][PheTyr] (SEQ ID NO:12)
(e) Leu[AsnAsp][AlaLys]ProAsnPheVal (SEQ ID NO:13)
(f) PhePhePheArgGlu (SEQ ID NO:14)
PhePhe[PheTyr]ArgGlu[ThrAsn] (SEQ ID NO:15)
PhePheArgGlu[ThrAsn]Ala (SEQ ID NO:16)
Phe[PheTyr]ArgGlu[ThrAsn]Ala (SEQ ID NO:17)
TyrPhePhe[PheTyr]ArgGlu (SEQ ID NO:18)
[PheTyr]PhePhe[PheTyr]ArgGlu (SEQ ID NO:19)
[PheTyr][PheTyr][PheTyr]ArgGlu[ThrAsn]Ala (SEQ ID NO:20)
[IleVal][PheTyr]Phe[PheTyr][PheTyr]ArgGlu (SEQ ID NO:21)
Asp[LysPheTyr]Val[PheTyr][PheTyrLeu][PheTyrIleLeu][PheTyr] (SEQ ID NO:22)
Asp[LysPheTyr]Val[PheTyr][PheTyrIleLeu][PheTyrIle][PheTyr] (SEQ ID NO:82)
[ValIle][PheTyr][PheTyrLeu][PheTyrIleLeu]Phe[ArgThr]Xaa[ThrAsn] (SEQ ID NO:83)
[ValIle][PheTyr][PheTyrIleLeu][PheTyrIle]Phe[ArgThr]Xaa[ThrAsn] (SEQ ID NO:84)
[ValIle][PheTyr][PheTyrIleLeu][PheTyrIleLeu]PheArgXaa[ThrAsn] (SEQ ID NO:85)
[ValIle][PheTyr][PheTyrLeu][PheTyrIleLeu][PheTyr][ArgThr][GluAspVal][ThrAsn] (SEQ ID NO:86)
(g) Glu[PheTyr]IleAsn[CysSer]GlyLys (SEQ ID NO:25)
[PheTyr]IleAsnCysGlyLys[AlaValIle] (SEQ ID NO:26)
(h) Arg[ValIle][AlaGly][ArgGln][ValIle]CysLys (SEQ ID NO:27)
Arg[ValIle]Xaa[ArgGln][ValIle]CysXaaXaaAsp (SEQ ID NO:28)
GlyLys[ValAlaIle]XaaXaaXaaArg[ValAlaIle]XaaXaaXaaCysLys (SEQ ID NO:29)
(i) [ArgLysAsn]Trp[ThrAla][ThrAlaSer][PheTyrLeu]Leu[LysArg] (SEQ ID NO:87)
[PheTyr]Leu[LysArg][AlaSer]ArgLeu[AsnIle]Cys (SEQ ID NO:31)
[AsnIle]CysSer[IleVal][ProSer]Gly (SEQ ID NO:32)
Trp[ThrAla][ThrAlaSer][PheTyrLeu]LeuLys[AlaSerValIleLeu]XaaLeu (SEQ ID NO:88)
Trp[ThrAlaSer][ThrAlaSer][PheTyrLeu]LeuLys[AlaSerIleLeu]XaaLeu (SEQ ID NO:89)
Trp[ThrAla][ThrAlaSer]XaaLeuLysXaaXaaLeuXaaCys (SEQ ID NO:90)
(j) [PheTyr][PheTyr][AsnAsp]GluIleGlnSer (SEQ ID NO:36)
[PheTyr]Pro[PheTyr][PheTyr][PheTyr][AsnAsp]Glu (SEQ ID NO:37)
(k) GlySerAla[ValIleLeu]CysXaa[PheTyr] (SEQ ID NO:38)
SerAla[ValIle]CysXaa[PheTyr]XaaMet (SEQ ID NO:39)
(l) AsnSer[AsnAla]TrpLeu[ProAla]Val (SEQ ID NO:40)
(m) [ValLeuIle]Pro[GluAspTyrSerPhe]ProArgProGly (SEQ ID NO:41)
[ValLeuIle]ProXaaProArgProGlyXaaCys (SEQ ID NO:91)
Pro[GluAspTyrSerPhe]ProArgProGly[ThrGlnSer]Cys (SEQ ID NO:43)
(n) AspPro[HisPheTyr]Cys[AlaGly]Trp (SEQ ID NO:44)
Pro[HisPheTyr]Cys[AlaGly]TrpAsp (SEQ ID NO:45)
AspProXaaCys[AlaGly]TrpAsp (SEQ ID NO:46)
CysXaaXaaXaaXaaAspProXaaCysXaaTrpAsp (SEQ ID NO:47)
CysXaaXaaXaaAspProXaaCysXaaTrpAsp (SEQ ID NO:48)
CysXaaXaaAspProXaaCysXaaTrpAsp (SEQ ID NO:49)
CysXaaXaaCysXaaXaaXaaXaaAspXaaXaaCysXaaTrpAsp (SEQ ID NO:50)
CysXaaXaaCysXaaXaaXaaAspXaaXaaCysXaaTrpAsp (SEQ ID NO:51), and
CysXaaXaaCysXaaXaaAspXaaXaaCysXaaTrpAsp (SEQ ID NO:52).

16. A method according to claim 12, wherein said peptide sequence is selected from the group consisting of:

(f) TyrPhePhe[PheTyr]ArgGlu (SEQ ID NO:18)

Asp[LysTyr]Val[PheTyr][PheTyrLeu][PheTyrIleLeu][PheTyr] (SEQ ID NO:92)

Asp[LysTyr]Val[PheTyr][PheTyrIleLeu][PheTyrIle][PheTyr] (SEQ ID NO:93)

[ValIle]Tyr[PheTyrLeu][PheTyrIleLeu]Phe[ArgThr]Xaa[ThrAsn] (SEQ ID NO:94)

[ValIle]Tyr[PheTyrIleLeu][PheTyrIle]Phe[ArgThr]Xaa[ThrAsn] (SEQ ID NO:95)

[ValIle]Tyr[PheTyrIleLeu][PheTyrIleLeu]PheArgXaa[ThrAsn] (SEQ ID NO:96)

Val[PheTyr][PheTyrLeu][PheTyrIleLeu][PheTyr][ArgThr][GluAspVal][ThrAsn] (SEQ ID NO:97)

Val[PheTyr][PheTyrIleLeu][PheTyrIle][PheTyr][ArgThr][GluAspVal][ThrAsn] (SEQ ID NO:98)

Val[PheTyr][PheTyrIleLeu][PheTyrIleLeu][PheTyr]Arg[GluAspVal][ThrAsn] (SEQ ID NO:99)

(n) CysXaaXaaXaaAspProXaaCysXaaTrpAsp (SEQ ID NO:48)

CysXaaXaaAspProXaaCysXaaTrpAsp (SEQ ID NO:49)

CysXaaXaaCysXaaXaaXaaAspXaaXaaCysXaaTrpAsp (SEQ ID NO:51), and

CysXaaXaaCysXaaXaaAspXaaXaaCysXaaTrpAsp (SEQ ID NO:52).

17. A method according to claim 1, wherein said polypeptide comprises an amino acid sequence selected from SEQ ID NO:54, 56, 58, 60, 62 and 64.

18. A method according to claim 12, wherein said polypeptide comprises SEQ ID NO:54.

19. A method according to claim 1, wherein said polypeptide comprises SEQ ID NO:56.

20. A method according to claim 12, wherein said polypeptide comprises SEQ ID NO:58.

21. A method according to claim 12, wherein said polypeptide comprises SEQ ID NO:60.

22. A method according to claim 12, wherein said polypeptide comprises SEQ ID NO:62.

23. A method according to claim 12, wherein said polypeptide comprises SEQ ID NO:64.

* * * * *